(12) United States Patent
Giuffrida et al.

(10) Patent No.: US 11,040,198 B1
(45) Date of Patent: *Jun. 22, 2021

(54) MOVEMENT DISORDER THERAPY SYSTEM, DEVICES AND METHODS, AND METHODS OF REMOTELY TUNING

(71) Applicants: Joseph P Giuffrida, Hinckley, OH (US); Dustin A Heldman, Shaker Heights, OH (US); Thomas O Mera, Columbus, OH (US)

(72) Inventors: Joseph P Giuffrida, Hinckley, OH (US); Dustin A Heldman, Shaker Heights, OH (US); Thomas O Mera, Columbus, OH (US)

(73) Assignee: Great Lakes NeuroTechnologies Inc., Cleveland, OH (US)

( * ) Notice: Subject to any disclaimer, the term of this patent is extended or adjusted under 35 U.S.C. 154(b) by 1462 days.

This patent is subject to a terminal disclaimer.

(21) Appl. No.: 15/016,928

(22) Filed: Feb. 5, 2016

Related U.S. Application Data

(63) Continuation of application No. 14/022,323, filed on Sep. 10, 2013, now Pat. No. 9,289,603, which is a
(Continued)

(51) Int. Cl.
| | |
|---|---|
| *A61N 1/36* | (2006.01) |
| *G16H 40/60* | (2018.01) |
| *G16H 20/10* | (2018.01) |

(52) U.S. Cl.
CPC ..... *A61N 1/36067* (2013.01); *A61N 1/36128* (2013.01); *G16H 20/10* (2018.01); *G16H 40/60* (2018.01); *A61N 2001/36039* (2013.01)

(58) Field of Classification Search
CPC .......... G06Q 50/22–24; A61N 1/36128; A61N 1/36067
See application file for complete search history.

(56) References Cited

U.S. PATENT DOCUMENTS

| | | |
|---|---|---|
| 5,716,377 A | 2/1998 | Rise et al. |
| 5,833,709 A | 11/1998 | Rise et al. |
| (Continued) | | |

FOREIGN PATENT DOCUMENTS

| | | |
|---|---|---|
| WO | 2006033039 A1 | 3/2006 |
| WO | 2011133583 A1 | 10/2011 |
| WO | 2012166860 A1 | 12/2012 |

OTHER PUBLICATIONS

Thomas Mera, Jerrold L. Vitek, Jay L. Alberts, Joseph P. Giuffrida, "Kinematic optimization of deep brain stimulation across multiple motor symptoms in Parkinson's disease", Journal of Neuroscience Methods, vol. 198, Issue 2, 2011, pp. 280-286, ISSN 0165-0270. (Year: 2011).*

(Continued)

*Primary Examiner* — Robert A Sorey
(74) *Attorney, Agent, or Firm* — Brian Kelkowski

(57) ABSTRACT

The present invention relates to methods for remotely tuning treatment parameters in movement disorder therapy systems where the subject and clinician are located remotely from each other. The present invention still further provides methods of quantifying movement disorders for the treatment of patients who exhibit symptoms of such movement disorders including, but not limited to, Parkinson's disease and Parkinsonism, Dystonia, Chorea, and Huntington's disease, Ataxia, Tremor and Essential Tremor, Tourette syndrome, stroke, and the like. The present invention yet further relates to methods of remotely tuning a therapy device using objective quantified movement disorder symptom data to determine the therapy setting or parameters to be transmitted and provided to the subject via his or her therapy device. The present invention also provides treatment and tuning remotely, allowing for home monitoring of subjects.

20 Claims, 14 Drawing Sheets

Related U.S. Application Data continuation-in-part of application No. 13/861,790, filed on Apr. 12, 2013, now Pat. No. 9,393,418, and a continuation-in-part of application No. 13/918,948, filed on Jun. 15, 2013, now Pat. No. 9,211,417.

(60) Provisional application No. 61/698,890, filed on Sep. 10, 2012.

(56) References Cited

U.S. PATENT DOCUMENTS

| | | | |
|---|---|---|---|
| 6,366,813 B1 | 4/2002 | DiLorenzo | |
| 6,484,059 B2 | 11/2002 | Gielen | |
| 7,010,351 B2 | 3/2006 | Firlik et al. | |
| 7,231,254 B2 | 1/2007 | DiLorenzo | |
| 7,184,837 B2 | 2/2007 | Goetz | |
| 7,209,787 B2 | 4/2007 | DiLorenzo | |
| 7,236,831 B2 | 6/2007 | Firlik et al. | |
| 7,239,926 B2 | 7/2007 | Goetz | |
| 7,242,984 B2 | 7/2007 | DiLorenzo | |
| 7,252,090 B2 | 8/2007 | Goetz | |
| 7,305,268 B2 | 12/2007 | Gliner et al. | |
| 7,313,440 B2 | 12/2007 | Miesel | |
| 8,845,557 B1* | 9/2014 | Giuffrida | A61B 5/0022 600/595 |
| 9,289,603 B1* | 3/2016 | Giuffrida | A61B 5/1101 |
| 9,314,190 B1* | 4/2016 | Giuffrida | A61B 5/11 |
| 10,016,606 B2* | 7/2018 | Afshar | A61B 5/04012 |
| 2004/0249422 A1 | 12/2004 | Gliner et al. | |
| 2005/0021104 A1 | 1/2005 | DiLorenzo | |
| 2005/0212097 A1 | 9/2005 | Shih et al. | |
| 2005/0234309 A1 | 10/2005 | Klapper | |
| 2006/0015153 A1* | 1/2006 | Gliner | A61N 1/3606 607/45 |
| 2007/0032834 A1 | 2/2007 | Gliner et al. | |
| 2007/0055322 A1 | 3/2007 | Forsberg et al. | |
| 2007/0162086 A1* | 7/2007 | DiLorenzo | A61B 5/04001 607/45 |
| 2007/0179534 A1 | 8/2007 | Firlik et al. | |
| 2007/0213783 A1* | 9/2007 | Pless | A61N 1/36071 607/42 |
| 2007/0255118 A1 | 11/2007 | Miesel | |
| 2007/0276441 A1 | 11/2007 | Goetz | |
| 2008/0045775 A1* | 2/2008 | Lozano | A61N 1/36014 600/12 |
| 2008/0058893 A1* | 3/2008 | Naujokat | A61N 1/08 607/45 |
| 2008/0071150 A1 | 3/2008 | Miesel et al. | |
| 2008/0097553 A1 | 4/2008 | John | |
| 2008/0119900 A1 | 5/2008 | DiLorenzo | |
| 2008/0195166 A1* | 8/2008 | Sun | A61B 5/0478 607/18 |
| 2008/0281376 A1* | 11/2008 | Gerber | A61N 1/36082 607/48 |
| 2008/0312513 A1* | 12/2008 | Simon | A61B 5/16 600/300 |
| 2009/0083070 A1 | 3/2009 | Giftakis et al. | |
| 2009/0192556 A1* | 7/2009 | Wu | A61B 5/0031 607/3 |
| 2010/0010432 A1* | 1/2010 | Skelton | A61B 5/103 604/66 |
| 2010/0228314 A1 | 9/2010 | Goetz | |
| 2011/0087309 A1 | 4/2011 | Stypulkowski | |
| 2011/0208012 A1 | 8/2011 | Gerber et al. | |
| 2012/0016435 A1 | 1/2012 | Rom | |
| 2012/0197611 A1 | 8/2012 | Butson et al. | |
| 2014/0074179 A1* | 3/2014 | Heldman | A61B 5/1101 607/45 |
| 2014/0153794 A1* | 6/2014 | Varaklis | G06T 7/0012 382/128 |
| 2014/0276130 A1* | 9/2014 | Mirelman | A61B 5/1104 600/483 |
| 2014/0336539 A1* | 11/2014 | Torres | A61B 5/4076 600/595 |

OTHER PUBLICATIONS

T. Mera, et al., "Kinematic optimization of deep brain stimulation across multiple motor symptoms in Parkinson's disease," Journal of Neuroscience Methods, vol. 198, No. 2, pp. 280-286, Jun. 15, 2011 (Epub Apr. 1, 2011), Netherlands.

Glenn, B. Neurotech company looks to break into deep brain stimulation market for Parkinson's. MedCity News. Mar. 27, 2012. (available online at: http://medcitynews.com/2012/03/neurotech-company-looks-to-break-into-deep-brain-stimulation-market-for-parkinsons-disease/).

Fischer, et al. Epilepsy Treatment Stimulus Package? Deep brain Stimulation in Treatment-Resistant Focal Epilepsy. Epilepsy Currents. vol. 10, No. 6, Nov./Dec. 2010. (available online at: http://www.ncbi.nlm.nih.gov/pmc/articles/PMC3001023/pdf/epc0010-0148.pdf).

T. Mera, et al., "ParkinTune Automated Parkinson's Disease motor symptom assessment for deep brain stimulation programming", Parkinsonism and Related Disorders, Elsevier Science, Oxford, GB, vol. 15, Dec. 1, 2009, p. S101.

Joseph P. Giuffrida et al., "Automated Optimization of Deep Brain Stimulation Settings Across Multiple Parkinson's Disease Motor Symptoms", 2010 American Academy of Neurology Annual Meeting, May 15, 2010.

\* cited by examiner

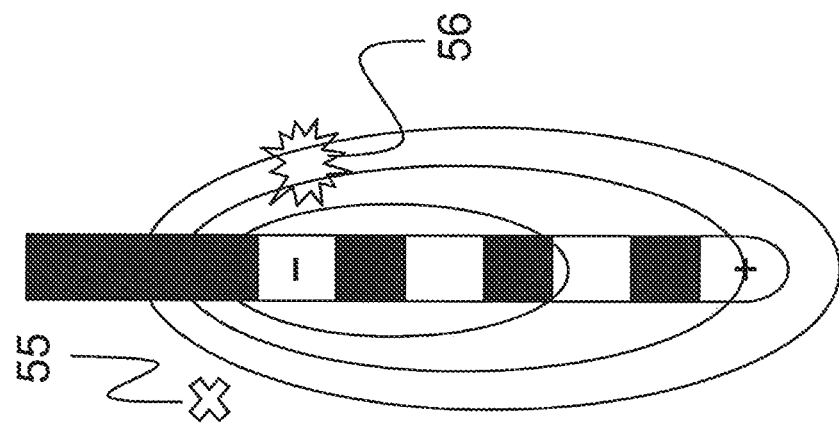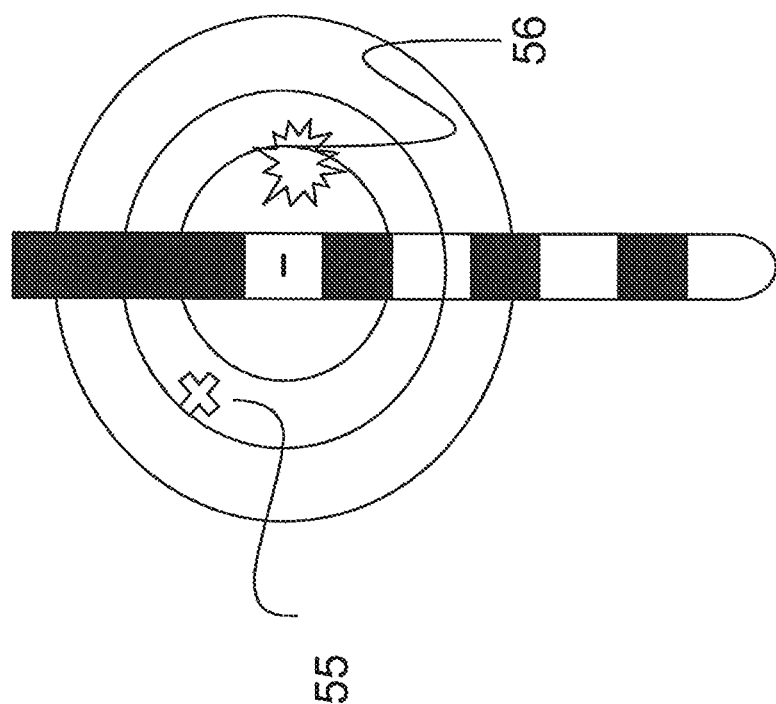
FIG. 9

MOVEMENT DISORDER THERAPY SYSTEM, DEVICES AND METHODS, AND METHODS OF REMOTELY TUNING

CROSS-REFERENCE TO RELATED APPLICATIONS

This application is a continuation of U.S. patent application Ser. No. 14/022,323, which was filed on Sep. 10, 2013, and which claims priority to the following applications and patents: 1) as a non-provisional application of provisional U.S. Patent Application Ser. No. 61/698,890, which was filed on Sep. 10, 2012; 2) as a continuation-in-part of U.S. patent application Ser. No. 13/861,790 which was filed on Apr. 12, 2013; and 3) as a continuation-in-part of U.S. patent application Ser. No. 13/918,948 which was filed on Jun. 15, 2013, and which issued as U.S. Pat. No. 9,211,417 on Mar. 13, 2014.

BACKGROUND OF THE INVENTION

(1) Field of the Invention

The present invention relates to therapeutic medical apparatus systems, delivery systems, devices and/or methods, and to apparatus and methods for using neural stimulation to alleviate the symptoms of movement disorders, such as those associated with Parkinson's disease, essential tremor, dystonia, and Tourette's syndrome, including tremor, bradykinesia, rigidity, gait/balance disturbances, and dyskinesia, and also for treating mental health disorders such as major depression, bipolar disorder, and obsessive compulsive disorder for example. The present invention further relates to the use of a movement disorder diagnostic device for remotely adjusting, or tuning, therapeutic systems, devices, delivery systems, as well as methods thereof.

(2) Technology Review

A current trend in the treatment of diseases identified as being associated with the central nervous system is the stimulation of target areas of the central nervous system to affect therapeutic benefit. Such stimulation has been accomplished with, for example, implanted electrodes that deliver electrical stimulation to target brain regions; one class of electrical neural stimulation devices has been categorized under the name "deep brain stimulation" (DBS). Although the exact neurological mechanisms by which DBS therapies succeed are complex and are not yet fully understood, such therapies have proven effective in treating Parkinson's disease motor symptoms (such as tremor, bradykinesia, rigidity, and gait disturbances), and investigation into the use of DBS for the treatment of this and other neurological and mental health disorders, including major depression, obsessive-compulsive disorder, tinnitus, obesity, criminal tendencies, and antisocial disorders, is ongoing.

Parkinson's disease (PD) affects the motor system and can be characterized by motor symptoms including tremor, bradykinesia, and impaired gait. When diagnosed, dopamine replacement medication is prescribed. However, over time drug effectiveness decreases, requiring increased dosage. Frequent and stronger side effects such as dyskinesias (uncontrolled, irregular movements) and unpredictable "on"/"off" episodes are cause for more invasive intervention. Deep brain stimulation (DBS) surgery is performed when medication no longer adequately treats symptoms. Significant costs are not only associated with the initial implant surgeries (~$40,000), but also subsequent stimulator battery replacements (~$10,000-20,000), outpatient programming sessions (~$1,000), and geographic disparities can put a significant financial and emotional burden on patients over many years, especially if the expected therapeutic improvement is not achieved. Although DBS has become a standard of care for many advanced stage PD patients, post-surgical outcomes are not equal across patients. A University of Florida study followed over 100 DBS patients, primarily PD, seeking referral to their movement disorder specialist after experiencing unsatisfactory improvement. Of those patients, 28% had been misdiagnosed presurgery and 90% had unsatisfactory symptomatic benefit including 40% for tremor, 37% gait, 11% for motor fluctuations and dyskinesias, and 14% for bradykinesia. The study also strongly argues for the need of preoperative education to ensure appropriate referral and selection of DBS candidates.

As a result, there are no set criteria for surgical patient selection. Subjective screening questionnaires have been developed to determine appropriate candidates based on a significant levodopa response (greater than 25%), the presence of motor fluctuations and dyskinesias, and minimal to no cognitive decline. However, methods to accurately evaluate these criteria are severely lacking for several reasons. First, the pattern and severity of motor symptom and dyskinesias vary greatly throughout the day. Therefore, an in-clinic assessment over multiple medication dose cycles is not feasible and is conducted under artificial conditions. Patients are typically asked to come in OFF PD medications from the previous night. Long travel days and pain and stress associated with being in this therapy state may induce fatigue and increased symptom severity. Second, clinical rating scales, most commonly the Unified Parkinson's Disease Rating Scale (UPDRS), are used to evaluate ON and OFF PD symptom states. Under the UPDRS, symptoms are subjectively rated on a 0-4 scale corresponding to normal, slight, mild, moderate, and severe, which can suffer from poor inter- and intra-rater reliability. An alternative, using home diaries, relies entirely on the patient's perception of their medication state and their level of compliance. Patients may also underestimate dyskinesia and motor symptom severity and have difficulty distinguishing between dyskinesia, tremor, and normal voluntary movements, a situation that can make evaluating medication response particularly challenging. Third, limited work has been conducted to directly compare pre-surgery medication response with post-surgery outcome in order to better select DBS candidates.

Access to movement disorder specialists to undergo the subjective screening questionnaires may require many clinical visits and can be financially burdensome for the geographically disparate subset of the PD population or those unable to travel. Movement disorder center locations can limit access to well-trained clinicians and effective symptom management. Rural patients in one study had a significantly worse quality of life score than their urban counterparts. Telehealth technologies such as home monitoring and online patient data management can have a significant impact on the equity, accessibility, and management of PD for patients who live in rural and remote communities or those unable to travel. In particular, one study showed that over a three-year period, telemedicine used for 100 follow-up visits for 34 PD patients left patients and providers satisfied with use of the technology and their savings amounted to approximately 1500 attendant travel hours, 100,000 travel kilometers, and $37,000 in travel and lodging costs. Typically, medication for Parkinson's disease (PD) consists of Levodopa to alleviate symptoms. Over time, however, the medication has reduced efficacy and shows increased occurrence of side effects such as dyskinesias. Once side effects outweigh benefits, patients consider deep brain stimulation (DBS). An electrode/wire lead is implanted in a specific location in the brain which shows hyperactivity in PD patients and is sensitive to electrical stimulation. PD target sites are typically the subthalamic nucleus (STN) or globus pallidus internus (GPi). The tremor-specific target site is generally the ventral intermedius nucleus of the thalamus (VIM). Electrical pulses characterized by amplitude (volts), current (amps), frequency (Hz), and pulse width (microseconds) are regulated by an implantable pulse generator (IPG) placed beneath the skin on the chest. Stimulation affects motor symptoms on the contralateral side, i.e., right side tremor will be treated on the left brain. After a patient has been implanted and recovered, programming sessions will fine tune stimulation settings described above in order to minimize symptom severity, minimize side effects, and maximize IPG battery life span. Although medication is not eliminated, it is typically reduced significantly. DBS efficacy decreases over time as the body adjusts to stimulation and protein buildup around electrode lead attenuates electrical field. Programming sessions are required throughout the patient's lifetime, though the frequency of adjustments is typically greater at first.

A typical implanted DBS stimulation lead consists of a thin insulated needle comprising four platinum/iridium electrodes spaced 0.5 or 1.5 mm apart along the length of the lead. One or multiple leads may be implanted in a target brain region or regions to provide symptom-inhibiting high-frequency stimulation, although some research suggests that excellent results can be achieved even when the lead is implanted distant from a target region. A DBS lead is connected to an implantable pulse generator (IPG), which serves as a controller and power source, via an extension cable tunneled subcutaneously to a subcutaneous pocket in the chest or abdominal cavity. The IPG typically includes a battery and circuitry for telemetered communication with an external programming device used to adjust, or "tune," DBS stimulation parameters, which may include but are not limited to stimulation frequency, amplitude, pulse width (or wavelength), waveform type, and contact configuration (that is, the selection of which electrodes are utilized from among the electrodes available on a lead, and, if two or more electrodes are active, the relative polarity of each), and the like. These parameters are initially set during implantation surgery separately and independently for each DBS lead that is implanted, and are then further fined-tuned in the outpatient clinic or in a doctor's office following surgery to maximize therapeutic benefit and minimize undesirable stimulation-induced side effects. The first such programming session usually takes place several weeks following implantation surgery, after the patient has recovered and inflammation at the lead placement site has subsided.

DBS programming may be performed by movement disorder neurologists, neurosurgeons, fellows, occupational and physical therapists, nurses, or employees of the DBS manufacturer. However, many patients have inadequate access to DBS programming due to physicians and patients relocating as well as implantations occurring at facilities far from a patient's home. Additionally, there is a shortage of health care professionals highly trained in DBS programming. This can partially be explained by a reluctance to participate in DBS management due to a lack of familiarly with electrophysiology or possibly the costs associated with postoperative DBS management. Retrospective studies found that DBS programming sessions take more than twice as long as typical evaluations by movement disorder neurologists. Furthermore, programming sessions must be limited to 1-3 hours since longer sessions result in patient fatigue or lightheadedness. Multiple visits lead to additional travel costs and can be particularly difficult for those traveling from rural areas.

The approaches to programming can vary greatly across institutions. Strict iterative procedures whereby initial subjective test results based on human observation are used to determine the effect the parameters have of the patient and new parameters are determined based on those results by clinician calculation and observation are quite time consuming and therefore rarely followed. Many programmers make educated guesses as to the best settings based on their prior experience; however, this experience can vary across institutions and may not take into account varied lead positioning. Many programmers simply ignore bipolar or tripolar configurations whereby stimulation is provided from two or three contacts on a single DBS lead simultaneously, and do not adjust frequency or pulse width in an attempt to speed the programming process; however, neglecting these options can lead to suboptimal patient outcomes. Many clinician programmers do not fully appreciate the different programming parameters or modes of stimulation. In constant-voltage IPGs, the voltage of each pulse is set, but the current will automatically change based on the electrode impedance. This leads to variable amounts of current being delivered the stimulation target as impedances change. Additionally, since impedances will vary across electrode contacts, applying the same voltage on two different contacts will likely lead to different therapeutic currents being delivered. On the other hand, constant-current IPGs specify the current to be delivered and adjust the voltage accordingly based on the impedance. Since the therapeutic effects of DBS are based on current delivered at a given target, constant-current IPGs are preferable to constant-voltage IPGs.

While the above-described equipment and procedures are typical as of the filing of this application, variations and refinements may become commonplace as neural implant technology advances. Conceivably, uses of a multiplicity of DBS leads or networks of DBS leads may provide greater coverage, enabling the stimulation of larger and more varied target areas, and miniaturization and improved telemetry may obviate the need for the extension cable and/or the IPG altogether as leads become self-powering and/or self-controlling or permit for built-in telemetry. Advances in nanotechnology and materials may also allow DBS leads in the future to become self-repositioning, self-cleaning, or resistant to biological rejection for improved long-term therapeutic operation and more precisely targeted implantation.

The current standard in evaluating the severity of movement disorder symptoms in Parkinson's disease is the manually human scored Unified Parkinson's Disease Rating Scale (UPDRS) used to score motor tests, many of which involve repetitive movement tasks such as touching the nose and drawing the hand away repeatedly, or rapidly tapping the fingers together. A battery of exercises, typically a subset of the upper extremity motor section of the UPDRS, is normally completed during DBS lead placement surgery and subsequent programming sessions to evaluate performance while a clinician qualitatively assesses symptoms. Each test is typically evaluated by a clinician based solely on visual observation and graded on a scale that typically ranges from 0 (minor) to 4 (severe).

During DBS implantation surgery, various lead placement strategies are used, including inversion recovery imaging, reformatted anatomical atlases, and formula coordinates based on known landmarks. Implantation location is verified and adjusted based on electrophysiological mapping using techniques such as microelectrode recording and micro and macro stimulation. Currently, lead placement and stimulation parameters are modified based on subjective motor examinations such as clinical observation such as the UPDRS motor tasks during the implantation procedure. After lead placement, patient motor symptoms are evaluated in response to a set of stimulation parameters. Stimulation parameters are then adjusted, and motor exam repeated. This trial-and-error process of adjusting parameters and monitoring patient response is continued until an optimal electrode position and stimulation set are established. During this programming or "tuning" process, the clinician subjectively assesses motor symptom improvement.

Postoperatively, assessing DBS response and reprogramming stimulation parameters require a significant time commitment. Several stimulation parameters can be modified, including, but not limited to, electrode polarity, amplitude, current, pulse width, waveform type, and frequency. DBS programming and patient assessment may be performed by a variety of healthcare professionals, including movement disorder neurologists, neurosurgeons, fellows, occupational and physical therapists, nurses, and employees of the DBS manufacturer. Stimulation optimization is typically performed based on results of an exam such as the UPDRS, with the patient in four states (off medication/off DBS, off medication/on DBS, on medication/off DBS, and on medication/on DBS). The process of DBS adjustment is iterative and largely involves trial-and-error. Programming and patient assessment from preoperatively to one year after surgery requires approximately 30 hours of nursing time per patient.

Clinicians presently lack tools that combine physiological, electrical, and behavioral data to optimize electrode placement and stimulator programming. Optimizing electrode placement and stimulation parameters improves patient outcome by alleviating motor symptoms and minimizing complications. The present invention addresses this need for improved electrode placement and adjustment of deep brain stimulation parameters by providing a repeatable, automated or semi-automated tool that can assist stimulation parameter tuning during surgical electrode placement and outpatient programming sessions. In particular, the present invention aims to provide methods for the collection and transmission of objective biokinetic data, which data is then processed to output objective movement disorder symptom severity measures on a continuous scale in real-time to guide clinician decision making. The improved resolution and repeatable results of the present invention should reduce time and costs of DBS procedures as well as improve patient outcomes.

It is therefore an object of the present invention to provide a system for screening patients for viability of DBS therapy prior to extensive, repetitive travel and expense, and prior to requiring surgical implantation of DBS leads. It is further an object of the present inventions to provide such a screening system to help minimize healthcare costs and to prevent adverse effects in patient quality of life associated with ineffective or unnecessary surgery, and to help clinicians to better select courses of treatment for patients.

It is further an object of the present invention to couple at-home patient viability screening and automatically-assigned quantitative motor assessments with procedures and practices for DBS implantation and parameter tuning and programming in semi-automatic and automatic ways to provide improved and less costly movement disorder patient therapy.

It is further an object of the present invention to provide automated functional mapping based on objective motor assessments and algorithms for resolving an optimal set of programming parameters out of the thousands of possibilities to provide an expert system to enable programming at a local medical facility. The system is designed for use by any healthcare professional, but is particularly aimed at allowing a general practitioner or nurse with minimal training or experience in DBS programming and disease management to increase access to high-quality postoperative DBS management. The system will minimize the required expertise of the clinician by requiring little or no advanced knowledge of complex neurophysiology or MRI imaging.

Existing systems for quantifying Parkinson's disease motor symptoms are described in this application's parent applications (Provisional U.S. Patent Application Ser. No. 61/698,890 and U.S. patent application Ser. No. 13/861,790), which are herein incorporated by reference, and which describe novel systems for measuring motor dysfunction symptoms and computing measures based on UPDRS scores therefrom. Additionally, the present invention and system may benefit from similar and related systems, methods and devices such as those described in U.S. patent application Ser. No. 13/152,963, U.S. patent application Ser. No. 13/185,287, U.S. patent application Ser. No. 13/185,302, U.S. patent application Ser. No. 12/250,792, U.S. patent application Ser. No. 13/455,423, U.S. patent application Ser. No. 13/784,939, and U.S. patent application Ser. No. 13/785,273, which are hereby incorporated by reference. Preferably, the system and methods described therein are incorporated, in whole or in part, into the present invention as a means of automatic symptom quantification. The resultant scores objectively quantify movement disorder symptoms advantageously using a scale that is familiar to clinicians.

SUMMARY OF THE INVENTION

The present invention relates to methods for semi-automatically and automatically adjusting, or tuning, treatment parameters in movement disorder therapy devices and systems, and more specifically for remotely adjusting or tuning such devices and systems. Semi-automatic adjustment includes providing the clinician, physician or technician with objective, quantitative or semi-quantitative data or measurements related to a subject's movement disorder symptoms, determining desired parameters, and then remotely entering those parameters either semi-automatically or automatically into the subject's therapy device. Semi-automatic or automatic adjustment includes providing data including, but not limited to, objective, quantitative or semi-quantitative data and/or measurements related to a subject's movement disorder symptoms to an algorithm, using the data or measurements for determining desired parameters using the algorithm, and then entering those parameters either semi-automatically (i.e., allowing clinician, physician or technician to review and/or approve/adjust) or to automatically into the subject's therapy device. Alternatively or in addition, semi-automatic or automatic adjustment may not require sensors to provide data and/or measurements related to a subject's movement disorder symptoms, but rather may use qualitative or quantitative information such as, for example, traditional telemedicine techniques or remote observation by a clinician, physician or technician via video connection. In such embodiments, the clinician, physician or technician would perform a more classic scoring of the subject's symptoms rather than using quantified data and/or measurements from sensors attached to the subject's body or device. Remote adjustment or tuning includes the control and or decision regarding the therapy parameters to be programmed into the subject's therapy device being located remotely from the subject. For example, remote adjustment or tuning may be controlled by a clinician, physician or technician or an automated or semi-automated system using data transmitted from the subject and/or his or her therapy device without the subject having to travel to the clinical site to for such data to be obtained or transferred. The present invention further relates to a system for screening patients to determine if they are viable candidates for certain therapy modalities. The present invention still further provides methods of quantifying movement disorders for the treatment of patients who exhibit symptoms of such movement disorders including, but not limited to, Parkinson's disease and parkinsonism, Dystonia, Chorea, and Huntington's disease, Ataxia, Tremor and Essential Tremor, Tourette syndrome, and the like. The present invention yet further relates to methods of automatically and intelligently tuning a therapy device using objective quantified movement disorder symptom data acquired by a movement disorder diagnostic device with the therapy settings or parameters to be provided to the subject via his or her therapy device.

Objective measurement and quantification of a subject's movement disorder symptoms, including tremor, bradykinesia, dyskinesia, gait and/or balance disturbances, and the like requires, as a first step, a measurement of the movement. This measurement can be performed by measuring a single movement metric, different movement metrics, or a combination of a number of movement metrics; and the movement metric or metrics being measured may include linear or rotational displacement, velocity, or acceleration, or any other metric that could give a quantitative indication of motion; and the part of the body being measured for motion may be a limb (as at a wrist, ankle, or finger) or may be the trunk of the body (as at a shoulder or torso), and the head. Sensors used for measuring body movement or motion include gyroscopes and accelerometers, preferably miniaturized, electromagnets, video, a multitude of sensors or system disclosed herein, or other sensors known to those skilled in the art. Additionally, sensors for measuring physiological signals such as electromyogram (EMG), electrooculogram (EOG), electroencephalogram (EEG), electrocardiogram (EKG), or other physiological signals which can directly or indirectly measure movement metrics in the subject may be included if such sensors and signals may be used to sense, detect, measure, and/or quantify the subject's external body motion, or related aspects. Other systems that can be used to detect and measure body motion include motion capture systems, machine vision systems, sonic or laser Doppler velocity transducers, infrared systems, GPS, or any other system known to those skilled in the art. The movement disorder diagnostic device used in the present invention may incorporate one or more of any of the above sensors or systems. Currently used movement data acquisition and diagnostic systems, such as described in U.S. Pat. No. 8,187,209, herein incorporated by reference, may similarly be used. In the present disclosure, "movement data" is construed as including, but not being limited to, any signal or set of signals, analog or digital, corresponding to movement of any part of the body or multiple parts of the body, independently or in conjunction with each other. This includes physiological signals from which movement data or symptoms can be derived. Preferably, this movement data is generated with a movement sensor such as for example a gyroscope and/or an accelerometer, and additionally or optionally a video sensor.

Movement may be continuously measured over long time spans, or may be measured only over a short time span, for example, as during the period of one or more tests taken from or based on the UPDRS motor exam. A measurement time period comprises two separate time periods: (i) a sensing time during which the movement disorder diagnostic device and its included sensors are used to sense and measure the subject's external physical motion; and (ii) a processing or calculation time wherein the measured motion data is used to calculate objective scores and/or other kinematic data that quantify the severity of the subject's movement disorder symptoms and side effects, and wherein the scores. The measurement time required to adequately and accurately sense, measure and quantify the subject's movement can depend on the particular movement test or task being performed, which typically corresponds to a particular symptom of a movement disorder. Generally, however, the system aims to minimize the amount of measurement time required to obtain sufficient movement data and provide quantitative scores and/or kinematic data to continue the evaluative process. Preferably, the measurement time required to provide objective scores and/or kinematic data is less than about 120 minutes. More preferably, the measurement time required to provide objective scores and/or kinematic data is less than about 90 minutes. Still more preferably, the measurement time required to provide objective scores and/or kinematic data is less than about 60 minutes. Yet more preferably, the measurement time required to provide objective scores and/or kinematic data is less than about 45 minutes. Even more preferably, the measurement time required to provide objective scores and/or kinematic data is less than about 30 minutes. Still yet more preferably, the measurement time required to provide objective scores and/or kinematic data is less than about 15 minutes. Still even more preferably, the measurement time required to provide objective scores and/or kinematic data is less than about 10 minutes. Yet still more preferably, the measurement time required to provide objective scores and/or kinematic data is less than about 5 minutes. Yet even more preferably, the measurement time required to provide objective scores and/or kinematic data is less than about 60 seconds. Even still more preferably, the measurement time required to provide objective scores and/or kinematic data is less than about 30 seconds. Even yet more preferably, the measurement time required to provide objective scores and/or kinematic data is less than about 15 seconds. Still even yet more preferably, the measurement time required to provide objective scores and/or kinematic data is less than about 1 second.

In some embodiments, a periodic system may be employed wherein the subject's external body motions are sensed, measured, and quantified repeatedly but at predefined or altering intervals. In such periodic embodiments, the periodic measurements preferably conform to the above described measurement time period standards. Embodiments utilizing periodic measurement may begin when the subject attaches or dons the movement disorder diagnostic device, and may involve a step of instructing the subject to attach or don the device to begin a measurement period. Protocols for periodic measurement may be envisioned wherein a subject follows a particular schedule for measurement and quantification of movement disorder data, and wherein the schedule may change throughout the course of treatment and/or therapy. In still other embodiments, a continuous monitoring system may be employed wherein the movement disorder diagnostic device continuously senses, measures and quantifies the subject's external body movements over extended periods of time, such as hours, days, weeks or months. Preferably, in the continuous measurement embodiments, the diagnostic device senses, measures and/or quantifies the subject's external body movements substantially continuously, with no breaks or stoppages in its operation. However, the limits of continuous operation may be defined by characteristics of the device, such as battery life, form factor and construction (e.g., if it needs to be removed to shower), and other such concerns.

The movement disorder diagnostic device contains at least one electronic component that further may contain internal or onboard memory for storage of the movement data such that the data may be transferred at a later time. More preferably, the movement disorder diagnostic device further may contain communications electronics, which transmit the movement data to an external device for storage and/or analysis. The communication electronics preferably is/are wireless, and most preferably is/are radio frequency wireless. The external device may be a centralized storage database, parallel databases, a cloud-based database, a computer, tablet, cell phone including for example smartphone, personal data assistant (PDA) or similar device, or a combination of database and computer or communication devices. Preferably, such transmission of data occurs substantially in real-time. By real-time, it is meant that preferably, data is transmitted within 30 minutes of being acquired, measured, or calculated. More preferably, data is transmitted within 20 minutes of being acquired, measured, or calculated. Still more preferably, data is transmitted within 10 minutes of being acquired, measured, or calculated. Yet more preferably, data is transmitted within 5 minutes of being acquired, measured, or calculated. Even more preferably, data is transmitted within 5 minutes of being acquired, measured, or calculated. Still yet more preferably, data is transmitted within 3 minutes of being acquired, measured, or calculated. Even yet more preferably, data is transmitted within 60 seconds of being acquired, measured, or calculated. Yet still more preferably, data is transmitted within 45 seconds of being acquired, measured, or calculated. Yet even more preferably, data is transmitted within 30 seconds of being acquired, measured, or calculated. Even still more preferably, data is transmitted within 15 seconds of being acquired, measured, or calculated. Even yet more preferably, data is transmitted within 5 seconds of being acquired, measured, or calculated. Still even yet more preferably, data is transmitted within 1 second of being acquired, measured, or calculated. Yet even still more preferably, data is transmitted substantially simultaneously within milliseconds of being acquired, measured, or calculated.

Following measurement of symptomatic movement, the next step in objective quantification of a subject's movement disorder symptoms is the extraction of statistical kinematic features from the acquired movement data via processing. This processing may take place during or following data acquisition and may occur within a movement data acquisition device or within a different processing device, such as a personal computer, PDA, smart phone, tablet computer, touch screen interface, or the like, with which the acquisition device interfaces, either through a cable connection or by wireless transmission. Useful kinematic features that may be extracted from gyroscopic data may include, for example, peak power angular velocity, peak power angle, RMS angular velocity, frequency, maximum amplitude, maximum peak-to-peak amplitude, mean angular velocity, and wavelet parameters, as well as the covariance or standard deviation over time of any of these metrics. Useful kinematic features that may be extracted from accelerometer data may include, for example, peak power acceleration, peak power velocity, peak power position, RMS acceleration, RMS velocity, RMS position, frequency, maximum amplitude, maximum peak-to-peak amplitude, mean acceleration, and wavelet parameters, as well as the covariance or standard deviation over time of any of these metrics. In a movement data acquisition system, or movement disorder diagnostic measuring apparatus, that combines a three-axis accelerometer and a three-axis gyroscope to produce 6 channels of movement data, one or any combination of the above kinematic features can be extracted from any of the 6 kinematic channels to be used as inputs to a trained scoring algorithm in the next step. The listed kinematic features for the sensors above are intended to be exemplary, and not limiting; other types of sensors will produce different data from which different sets of features may be extracted.

The trained scoring algorithm used to process the kinematic features extracted from the movement data may comprise, for example, one or more of a simple or multiple linear regression, an artificial neural network, a Bayesian network, or a genetic algorithm. The output of the trained scoring algorithm may be a single score or multiple scores of any scale; a single score on the same scale as that of the UPDRS may be preferred in certain applications where simplicity or familiarity is the paramount concern, while more sophisticated scores and scales may be preferred for other advanced applications, such as those that involve recommendations for treatment or closed-loop automated treatment delivery.

In various embodiments, following the step of symptom quantification, a separate tuning algorithm may compute suggested changes to the therapy system parameter settings based on the result of the symptom quantification algorithm and known or predicted current therapy system parameter settings and physiological models.

Depending on the embodiment of the invention, the current therapy system parameter settings changes may be input into the algorithm by a software user interface (integrated tuning), or may be automatically sensed and input from the DBS parameter settings by communicating with a DBS implant or its programmer device or unit (intelligent tuning), or may be known because the DBS parameter settings have been preset to some known baseline settings or restored to a previously saved settings preset. The existing parameter settings might also be predicted or derived based, for example, on observed or measured therapy effectiveness. Suggested therapy system parameter settings changes are then input into the therapy system, and their effectiveness is measured using the above-described method of symptom quantification.

The process of tuning therapy system parameter settings may remain iterative, but the present invention significantly minimizes, or at least greatly reduces the time and expertise required to arrive at optimized stimulation or therapy parameter settings, advantageously allowing clinicians, technicians or physicians with lesser training or experience to adjust parameter settings during patient visits, and to do so in less time than is currently required. Additionally, the present invention increases access to geographically disparate populations by putting the expertise into the system and reducing or eliminating the need for an expert or trained clinician to be present with each subject.

Many embodiments of the present invention utilize a remote tuning or adjustment system. In such embodiments, at least one electronic component for transmitting and receiving signals is required. In such embodiments, data corresponding to the subject's measured and quantified movement and symptom data may be collected by the movement disorder diagnostic device and transmitted using the at least one electronic component for transmitting signals to a remote location or remote locations. The data may be transmitted to a clinical center or location where a clinician, physician or technician can view the data. In such embodiments, the clinician, physician or technician can then make a decision and determination regarding a second level of therapy settings that should be applied to the subject's therapy device. Alternatively or in addition, an algorithm may be used to provide the determination as to the second level of therapy parameters to be applied to the subject's therapy device, and a clinician, physician or technician may optionally review the settings determined by the algorithm. In the remote tuning or adjustment embodiments, once a determination as to a second or next level of therapy parameters is made, this second or next level of parameters is then transmitted back to the subject's therapy device where it is received by at least on electronic component for receiving signals. In still other remote embodiments, a tuning algorithm, as described below, of the movement disorder diagnostic device may provide suggested or determined second or next levels of therapy parameters, and in such embodiments the movement data and/or such suggested or determined parameters may be transmitted to storage or other remote locations as described. Additionally, the movement data and/or second or next level of therapy parameters may additionally be transmitted to a central server, cloud based server, or other such database for storage and backup purposes.

Many embodiments of the present invention include optimization or tuning algorithm(s) which are used to determine or recommend optimum therapy settings or parameters. Such optimization algorithms may include, but are not limited to simplex algorithms, extensions of the simplex algorithm designed for quadratic and/or linear function programming, combinatorial algorithms, and other multi-variant optimization algorithms known to those in the art. In order to determine what a desired or optimal level of therapy parameters might be, the subject's symptoms or side effects must first be measured and quantified. The measurement and quantification preferably take place while the subject is performing at least one movement disorder test as instructed. Once the initial measurement and quantification has been obtained, the system and/or, in some embodiments a clinician, physician or technician, programs a second level of therapy parameters into the subject's therapy device, and the subject repeats the movement disorder test(s) while the symptoms or side effects are again measured and quantified. This process is repeated until the desired result(s), goals or constraints are achieved. These processes and steps are described in greater detail below. Preferably, whether obtaining optimized therapy parameters or settings, or when iteratively testing to determine a second level of therapy parameters, preferably, the subject is instructed to perform, and performs, at least 1 movement disorder test, where the test comprises at least one task related to the subject's external body motion. More preferably, the subject is instructed to perform, and performs, at least 2 movement disorder tests. Still more preferably, the subject is instructed to perform, and performs, at least 3 movement disorder tests. Yet more preferably, the subject is instructed to perform, and performs, at least 4 movement disorder tests. Even more preferably, the subject is instructed to perform, and performs, at least 5 movement disorder tests. Still yet more preferably, the subject is instructed to perform, and performs, at least 6 movement disorder tests. Even still more preferably, the subject is instructed to perform, and performs, at least 7 movement disorder tests.

Optimization of stimulation or therapy parameters or settings can be described in reference to various constraints or desired results. In some embodiments, optimization, or the level of parameters or setting selected based at least in part on movement disorder tests, results and scores refers to a reduction or minimization of symptom occurrence and/or severity. Preferably in such embodiments, an optimized or second level of therapy parameters or settings corresponds to at least a 10% reduction in the occurrence and/or severity of the subject's symptoms while the subject is receiving therapy or is under the effects of recently received therapy. More preferably, an optimized or second level of therapy parameters or settings corresponds to at least a 20% reduction in the occurrence and/or severity of the subject's symptoms while the subject is receiving therapy or is under the effects of recently received therapy. Yet more preferably, an optimized or second level of therapy parameters or settings corresponds to at least a 30% reduction in the occurrence and/or severity of the subject's symptoms while the subject is receiving therapy or is under the effects of recently received therapy. Still more preferably, an optimized or second level of therapy parameters or settings corresponds to at least a 40% reduction in the occurrence and/or severity of the subject's symptoms while the subject is receiving therapy or is under the effects of recently received therapy. Even more preferably, an optimized or second level of therapy parameters or settings corresponds to at least a 50% reduction in the occurrence and/or severity of the subject's symptoms while the subject is receiving therapy or is under the effects of recently received therapy. Still yet more preferably, an optimized or second level of therapy parameters or settings corresponds to at least a 60% reduction in the occurrence and/or severity of the subject's symptoms while the subject is receiving therapy or is under the effects of recently received therapy. Even yet more preferably, an optimized or second level of therapy parameters or settings corresponds to at least a 70% reduction in the occurrence and/or severity of the subject's symptoms while the subject is receiving therapy or is under the effects of recently received therapy. Yet still more preferably, an optimized or second level of therapy parameters or settings corresponds to at least a 75% reduction in the occurrence and/or severity of the subject's symptoms while the subject is receiving therapy or is under the effects of recently received therapy. Even still more preferably, an optimized or second level of therapy parameters or settings corresponds to at least an 80% reduction in the occurrence and/or severity of the subject's symptoms while the subject is receiving therapy or is under the effects of recently received therapy. Yet even more preferably, an optimized or second level of therapy parameters or settings corresponds to at least an 85% reduction in the occurrence and/or severity of the subject's symptoms while the subject is receiving therapy or is under the effects of recently received therapy. Still even more preferably, an optimized or second level of therapy parameters or settings corresponds to at least a 90% reduction in the occurrence and/or severity of the subject's symptoms while the subject is receiving therapy or is under the effects of recently received therapy. Yet still even more preferably, an optimized or second level of therapy parameters or settings corresponds to at least a 95% reduction in the occurrence and/or severity of the subject's symptoms while the subject is receiving therapy or is under the effects of recently received therapy. Most preferably, an optimized or second level of therapy parameters or settings corresponds to substantially eliminating the occurrence and/or severity of the subject's symptoms while the subject is receiving therapy or is under the effects of recently received therapy.

In other embodiments, optimization, or the level of parameters or setting selected based at least in part on movement disorder tests, results and scores refers to a reduction or minimization of side effect occurrence and or severity. Side effects may be a result of pharmaceutical therapy (medication) the subject is receiving to treat his or her movement disorders, or from the stimulation therapy (e.g., DBS). Preferably in such embodiments, an optimized or second level of therapy parameters or settings corresponds to at least a 10% reduction in the occurrence and/or severity of the subject's side effects while the subject is receiving therapy or is under the effects of recently received therapy. More preferably, an optimized or second level of therapy parameters or settings corresponds to at least a 20% reduction in the occurrence and/or severity of the subject's side effects while the subject is receiving therapy or is under the effects of recently received therapy. Yet more preferably, an optimized or second level of therapy parameters or settings corresponds to at least a 30% reduction in the occurrence and/or severity of the subject's side effects while the subject is receiving therapy or is under the effects of recently received therapy. Still more preferably, an optimized or second level of therapy parameters or settings corresponds to at least a 40% reduction in the occurrence and/or severity of the subject's side effects while the subject is receiving therapy or is under the effects of recently received therapy. Even more preferably, an optimized or second level of therapy parameters or settings corresponds to at least a 50% reduction in the occurrence and/or severity of the subject's side effects while the subject is receiving therapy or is under the effects of recently received therapy. Still yet more preferably, an optimized or second level of therapy parameters or settings corresponds to at least a 60% reduction in the occurrence and/or severity of the subject's side effects while the subject is receiving therapy or is under the effects of recently received therapy. Even yet more preferably, an optimized or second level of therapy parameters or settings corresponds to at least a 70% reduction in the occurrence and/or severity of the subject's side effects while the subject is receiving therapy or is under the effects of recently received therapy. Yet still more preferably, an optimized or second level of therapy parameters or settings corresponds to at least a 75% reduction in the occurrence and/or severity of the subject's side effects while the subject is receiving therapy or is under the effects of recently received therapy. Even still more preferably, an optimized or second level of therapy parameters or settings corresponds to at least an 80% reduction in the occurrence and/or severity of the subject's side effects while the subject is receiving therapy or is under the effects of recently received therapy. Yet even more preferably, an optimized or second level of therapy parameters or settings corresponds to at least an 85% reduction in the occurrence and/or severity of the subject's side effects while the subject is receiving therapy or is under the effects of recently received therapy. Still even more preferably, an optimized or second level of therapy parameters or settings corresponds to at least a 90% reduction in the occurrence and/or severity of the subject's side effects while the subject is receiving therapy or is under the effects of recently received therapy. Yet still even more preferably, an optimized or second level of therapy parameters or settings corresponds to at least a 95% reduction in the occurrence and/or severity of the subject's side effects while the subject is receiving therapy or is under the effects of recently received therapy. Most preferably, an optimized or second level of therapy parameters or settings corresponds to substantially eliminating the occurrence and/or severity of the subject's side effects while the subject is receiving therapy or is under the effects of recently received therapy.

Preferably, where the desired result is to reduce or minimize the subject's movement disorder symptoms, the optimized or second level of therapy parameters results in a reduction or minimization of at least 1 movement disorder symptom. More preferably, the optimized or second level of therapy parameters results in a reduction or minimization of at least 2 movement disorder symptoms. Still more preferably, the optimized or second level of therapy parameters results in a reduction or minimization of at least 3 movement disorder symptoms. Yet more preferably, the optimized or second level of therapy parameters results in a reduction or minimization of at least 4 movement disorder symptoms. Even more preferably, the optimized or second level of therapy parameters results in a reduction or minimization of at least 5 movement disorder symptoms.

Preferably, where the desired result is to reduce or minimize the subject's side effects from medication or therapy, the optimized or second level of therapy parameters results in a reduction or minimization of at least 1 side effect. More preferably, the optimized or second level of therapy parameters results in a reduction or minimization of at least 2 side effects. Still more preferably, the optimized or second level of therapy parameters results in a reduction or minimization of at least 3 side effects. Yet more preferably, the optimized or second level of therapy parameters results in a reduction or minimization of at least 4 side effects. Even more preferably, the optimized or second level of therapy parameters results in a reduction or minimization of at least 5 side effects.

Other secondary constraints or desired results may also be considered when optimizing or determining a second level of therapy parameters or settings such as maximizing the battery life of the therapeutic (e.g., DBS) device, maximizing the therapeutic window, and the like. Such constraints or desired results as these are secondary only in that the primary goal of the therapy is to increase the subject's quality of life by reducing or minimizing symptoms or side effects, or balancing both, while also trying to improve the duration and quality of therapy otherwise. For example, maximizing battery life of the therapy device helps to increase the time required between subject's visits to the clinician, physician or technician as well as ensuring that the device has sufficient power and capability to effectively provide the determined levels of therapy. Similarly with maximizing the therapeutic window, which also increases the time between visits, but also maximizes the length of time that the stimulation therapy has a positive effect on the subject and reducing the number of stimulations required to achieve the desired results. Typically, the subject and his or her clinician, physician or technician will agree upon the primary desired result, such as minimizing symptoms, but numerous other such constraints will also be considered, weighed and balanced in determining the optimized or second level of parameters or settings.

Several embodiments may include a general optimization strategy in which combinations of the above desired results or constraints are used to select the appropriate optimized settings. For example, such embodiments may optimize based on reducing or minimizing both symptoms and side effects. Any combination of type and/or number of desired results or constraints may be used to optimize the system. Preferably, at least two different desired results or constraints are considered when determining an optimized group of therapy settings or parameters. More preferably, at least three different desired results or constraints are considered when determining an optimized group of therapy settings or parameters. Still more preferably, at least four different desired results or constraints are considered when determining an optimized group of therapy settings or parameters. Yet more preferably, at least five different desired results or constraints are considered when determining an optimized group of therapy settings or parameters. Even more preferably, at least six different desired results or constraints are considered when determining an optimized group of therapy settings or parameters. Most preferably, more than seven different desired results or constraints are considered when determining an optimized group of therapy settings or parameters.

Numerous embodiments of the present invention are envisioned in this disclosure. These following embodiments are examples of the many embodiments encompassed by the present invention, but do not in any way limit the many other embodiments covered by this disclosure.

One embodiment of the present invention includes a method of tuning a movement disorder therapy system comprising steps of providing a movement disorder diagnostic device to a subject having a deep brain stimulation (DBS) device with a first level of DBS parameters, the movement disorder diagnostic device comprising at least one physiological or movement sensor having a signal, instructing the subject to perform at least one movement disorder test(s) while the subject is undergoing DBS therapy or is under the effects of DBS therapy, measuring and quantifying motor symptoms of the subject based at least in part on the signal from the at least one physiological or movement sensor(s) during the at least one movement disorder test(s), transmitting data corresponding to the subject's measured and quantified motor symptoms to a clinician, physician or technician at a remote location, having the clinician, physician or technician determine, based at least in part on the data, a second level of DBS parameters, transmitting the second level of DBS parameters to the subject's DBS device, and entering the second level of DBS parameters into the subject's DBS device such that the subject's DBS device operates under the second level of DBS parameters.

Another embodiment of the present invention includes a method of tuning a movement disorder therapy system comprising steps of providing a movement disorder diagnostic device to a subject having a deep brain stimulation (DBS) device with a first level of DBS parameters, the movement disorder diagnostic device comprising at least one physiological or movement sensor having a signal, instructing the subject to perform at least one movement disorder test(s) while the subject is undergoing DBS therapy or is under the effects of DBS therapy, measuring and quantifying motor symptoms of the subject based at least in part on the signal from the at least one physiological or movement sensor(s) during the at least one movement disorder test(s), transmitting data corresponding to the subject's measured and quantified motor symptoms to a clinician, physician or technician at a remote location, having the clinician, physician or technician determine, based at least in part on the data, at least two optional groups of DBS parameters, each optional group of parameters corresponding to a different desired outcome or constraint, selecting one of the at least two optional groups of DBS parameters, transmitting the selected optional group of DBS parameters to the subject's DBS device, and entering the selected optional group of DB S parameters into the subject's DBS device such that the subject's DBS device operates under the second level of DBS parameters.

Yet another embodiment of the present invention includes a method of tuning a movement disorder therapy system comprising steps of providing a movement disorder diagnostic device to a subject having a deep brain stimulation (DBS) device with a first level of DBS parameters, the movement disorder diagnostic device comprising at least one physiological or movement sensor having a signal, instructing the subject to perform at least one movement disorder test(s) while the subject is undergoing DBS therapy or is under the effects of DBS therapy, measuring and quantifying motor symptoms of the subject based at least in part on the signal from the at least one physiological or movement sensor(s) during the at least one movement disorder test(s), transmitting data corresponding to the subject's measured and quantified motor symptoms to a clinician, physician or technician at a remote location, having the clinician, physician or technician determine, based at least in part on the data, a second level of DBS parameters, transmitting the second level of DBS parameters to the subject's DBS device, and automatically entering the second level of DBS parameters into the subject's DBS device such that the subject's DBS device operates under the second level of DBS parameters.

Still another embodiment of the present invention includes a method of tuning a movement disorder therapy system comprising steps of providing a movement disorder diagnostic device to a subject having a deep brain stimulation (DBS) device with a first level of DBS parameters, the movement disorder diagnostic device comprising at least one physiological or movement sensor having a signal, and a processor comprising an algorithm, instructing the subject to perform at least one movement disorder test(s) while the subject is undergoing DBS therapy or is under the effects of DBS therapy, measuring and quantifying motor symptoms of the subject based at least in part on the signal from the at least one physiological or movement sensor(s) during the at least one movement disorder test(s), entering data corresponding to the subject's measured and quantified motor symptoms into an algorithm, providing, with the algorithm, a second level of DBS parameters based at least in part on the data entered into the algorithm transmitting data corresponding to the subject's measured and quantified motor symptoms and the second level of DBS parameters to a clinician, physician or technician at a remote location, having the clinician, physician or technician approve or edit the second level of DBS parameters provided by the algorithm, and uploading, substantially simultaneously with transmitting, with at least one electronic component the second level of DBS parameters and/or measured and quantified motor symptoms to a database for storage and/or review by a clinician, technician or physician.

Still yet another embodiment of the present invention includes a method of tuning a movement disorder therapy system comprising steps of providing a movement disorder diagnostic device to a subject having a deep brain stimulation (DBS) device with a first level of DBS parameters, the movement disorder diagnostic device comprising at least one physiological or movement sensor having a signal, and a processor comprising an algorithm, instructing the subject to perform at least one movement disorder test(s) while the subject is undergoing DBS therapy or is under the effects of DBS therapy, measuring and quantifying motor symptoms of the subject based at least in part on the signal from the at least one physiological or movement sensor(s) during the at least one movement disorder test(s), entering the data corresponding to the subject's measured and quantified motor symptoms into an algorithm, determining, with the algorithm, at least two optional groups of DBS parameters, each optional group of parameters corresponding to a different desired outcome or constraint, transmitting data corresponding to the subject's measured and quantified motor symptoms and the at least two optional groups of DBS parameters to a clinician, physician or technician—at a remote location, having the clinician, physician or technician select at least two of the at least two optional groups of DBS parameters, combining the at least two selected optional groups of DBS parameters into one set of combined DBS parameters, transmitting the set of combined DBS parameters to the subject's DBS device, and entering the set of combined DBS parameters into the subject's DBS device such that the subject's DBS device operates under the second level of DBS parameters.

Yet still another embodiment of the present invention includes a method of tuning a movement disorder therapy system comprising steps of providing a movement disorder diagnostic device to a subject having a deep brain stimulation (DBS) device with a first level of DBS parameters, the movement disorder diagnostic device comprising at least one physiological or movement sensor having a signal, and a processor comprising an algorithm, instructing the subject to perform at least one movement disorder test(s) while the subject is undergoing DBS therapy or is under the effects of DBS therapy, measuring and quantifying motor symptoms of the subject based at least in part on the signal from the at least one physiological or movement sensor(s) during the at least one movement disorder test(s), entering data corresponding to the subject's measured and quantified motor symptoms into an algorithm, determining, with the algorithm, at least two optional groups of DBS parameters, each optional group of parameters corresponding to a different desired outcome or constraint, transmitting data corresponding to the subject's measured and quantified motor symptoms and the at least two optional groups of DBS parameters to a clinician, physician or technician at a remote location, having the clinician, physician or technician select one of the at least two optional groups of DBS parameters, and uploading, substantially simultaneously with transmitting, with at least one electronic component the selected optional group of DB S parameters and/or measured and quantified motor symptoms to a database for storage and/or review by a clinician, technician or physician.

Even yet another embodiment of the present invention includes a method of tuning a movement disorder therapy system comprising steps of providing a movement disorder diagnostic device to a subject having a deep brain stimulation (DBS) device with a first level of DBS parameters, the movement disorder diagnostic device comprising at least one physiological or movement sensor having a signal, and a processor comprising an algorithm, instructing the subject to perform at least one movement disorder test(s) while the subject is undergoing DBS therapy or is under the effects of DBS therapy, measuring and quantifying motor symptoms of the subject based at least in part on the signal from the at least one physiological or movement sensor(s) during the at least one movement disorder test(s), entering data corresponding to the subject's measured and quantified motor symptoms into an algorithm, determining, with the algorithm, at least two optional groups of DBS parameters, each optional group of parameters corresponding to a different desired outcome or constraint, transmitting data corresponding to the subject's measured and quantified motor symptoms and the second level of DBS parameters to a clinician, physician or technician at a remote location, having the clinician, physician or technician select at least two of the at least two optional groups of DBS parameters, combining the at least two selected optional groups of DBS parameters into one set of combined DB S parameters, and uploading, substantially simultaneously with transmitting, with at least one electronic component the combined DBS parameters and/or measured and quantified motor symptoms to a database for storage and/or review by a clinician, technician or physician.

Even still another embodiment of the present invention includes a method of tuning a movement disorder therapy system comprising steps of providing a movement disorder diagnostic device to a subject having a deep brain stimulation (DBS) device with a first level of DBS parameters, the movement disorder diagnostic device comprising at least one physiological or movement sensor having a signal, and a processor comprising an algorithm, displaying on a programming device a list of activities, actions or tasks for the subject to select from, having the subject elect at least one activity, action or task from the list on the programming device, selecting with the movement disorder diagnostic device a predetermined set of DBS parameters corresponding to the elected at least one activity, action or task, transmitting data corresponding to the subject's measured and quantified motor symptoms and the selected set of DBS parameters to a clinician, physician or technician at a remote location, having the clinician, physician or technician approve or edit the selected set of DBS parameters provided by the algorithm, transmitting and entering the approved or edited selected set of DBS parameters corresponding to the at least one elected activity, action or task into the subject's DBS device such that the subject's DBS device operates under the selected group of DBS parameters while the subject performs the at least one elected activity, action, or task.

Yet even another embodiment of the present invention includes a method of tuning a movement disorder therapy system comprising steps of providing a movement disorder diagnostic device to a subject having a deep brain stimulation (DBS) device with a first level of DBS parameters, the movement disorder diagnostic device comprising at least one physiological or movement sensor having a signal, and a processor comprising an algorithm, displaying on a programming device a list of activities, actions or tasks for the subject to select from, having the subject elect at least one activity, action or task from the list on the programming device, selecting with the movement disorder diagnostic device a predetermined set of DBS parameters corresponding to the elected at least one activity, action or task, entering with the programming device the group of selected DBS parameters corresponding to the at least one elected activity, action or task into the subject's DBS device such that the subject's DBS device operates under the selected group of DBS parameters, measuring and quantifying motor symptoms of the subject based at least in part on the signal from the at least one physiological or movement sensor(s) while the subject performs the at least one elected activity, action or task, entering data corresponding to the subject's measured and quantified motor symptoms into an algorithm, providing, with the algorithm, a second level of DBS parameters based at least in part on the data entered into the algorithm, the second level of DBS parameters maximizing the subject's ability to perform the at least one elected activity, action or task, transmitting data corresponding to the subject's measured and quantified motor symptoms and the second level of DBS parameters to a clinician, physician or technician at a remote location, having the clinician, physician or technician approve or edit the second level of DBS parameters provided by the algorithm, transmitting the approved or edited second level of DBS parameters to the subject's DBS device, and entering the second level of DBS parameters into the subject's DBS device such that the subject's DBS device operates under the second level of DBS parameters while the subject performs the at least one elected activity, action or task.

Still even another embodiment of the present invention includes a method of tuning a movement disorder therapy system comprising steps of providing a movement disorder diagnostic device to a subject having a deep brain stimulation (DBS) device with a first level of DBS parameters, the movement disorder diagnostic device comprising at least one physiological or movement sensor having a signal, and a processor comprising an algorithm, instructing the subject to perform at least one movement disorder test(s) while the subject is undergoing DBS therapy or is under the effects of DBS therapy, measuring and quantifying motor symptoms of the subject based at least in part on the signal from the at least one physiological or movement sensor(s) during the at least one movement disorder test(s), entering the data corresponding to the subject's measured and quantified motor symptoms into an algorithm, providing, with the algorithm, a second level of DBS parameters based at least in part on the data entered into the algorithm, transmitting data corresponding to the subject's measured and quantified motor symptoms and the second level of DBS parameters to a clinician, physician or technician at a remote location, having the clinician, physician or technician approve or edit the second level of DBS parameters provided by the algorithm, transmitting the approved or edited second level of DBS parameters to the subject's DBS device, and automatically entering the second level of DBS parameters into the subject's DBS device such that the subject's DBS device operates under the second level of DBS parameters.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

BRIEF DESCRIPTION OF THE DRAWINGS

FIG. 9. Illustration depicting the ability of bipolar stimulation to shape the electrical stimulation field to avoid activating a side effect region of the brain as opposed to monopolar stimulation which does not allow shaping of the electrical field.

DETAILED DESCRIPTION OF THE INVENTION

Figure 1:
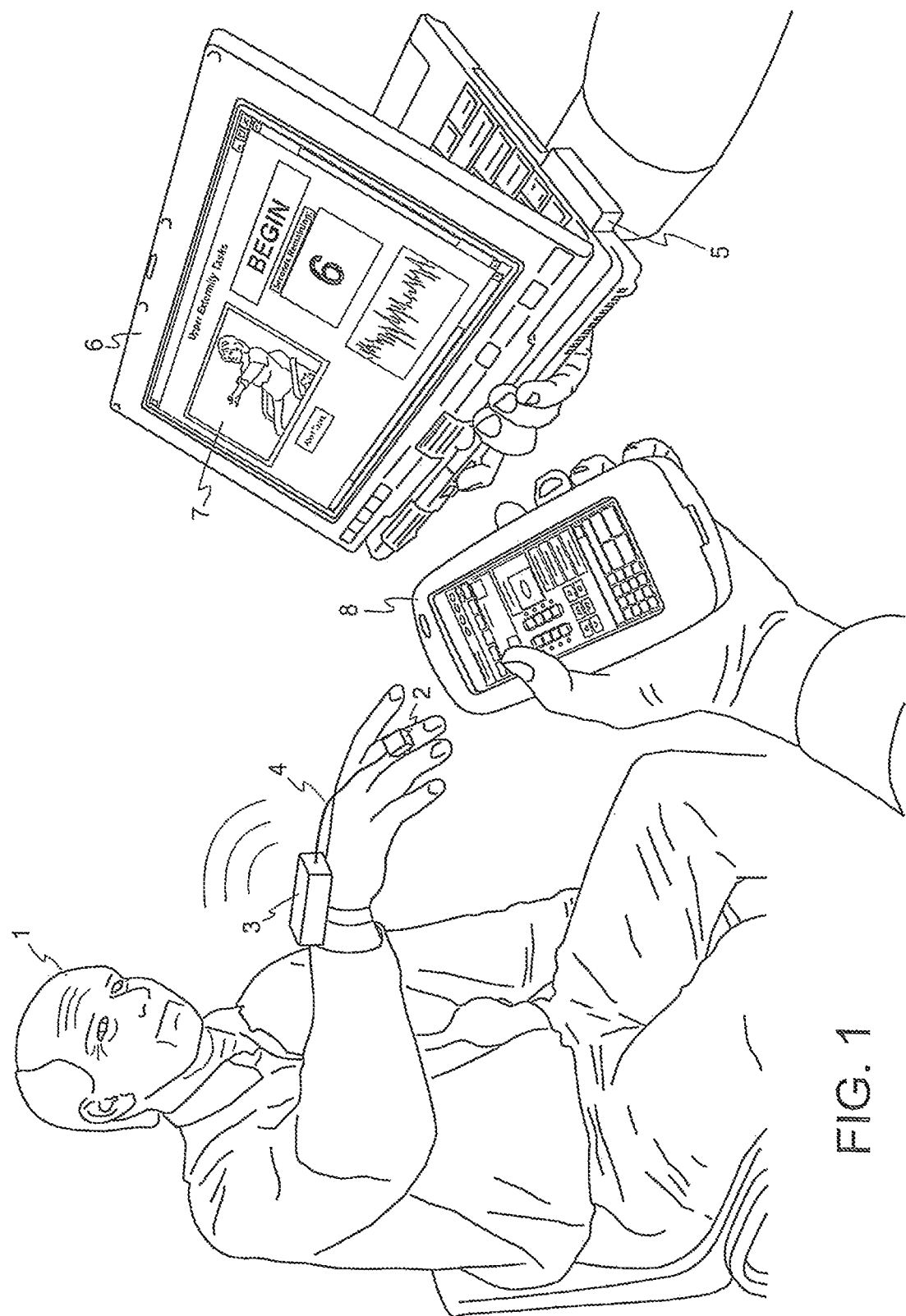
FIG. 1. Schematic view of a subject undergoing post-surgical DBS adjustment with one embodiment of the invention involving automated instruction of the subject and electronic transmission between the system and the subject's DBS device.

The present invention relates to methods for semi-automatically and automatically adjusting, or tuning, treatment parameters in movement disorder therapy systems from a location separate from the patients (remotely). Semi-automatic adjustment includes providing the clinician, physician or technician with objective, quantitative or semi-quantitative data or measurements related to a subject's movement disorder symptoms, determining desired parameters, and then entering those parameters either semi-automatically or automatically into the subject's device. Semi-automatic and automatic adjustment includes providing objective, quantitative or semi-quantitative data or measurements related to a subject's movement disorder symptoms to an algorithm, determining desired parameters using the algorithm, and then entering those parameters either semi-automatically (i.e., allowing clinician, physician or technician to manually adjust the parameters or settings) or automatically (i.e., parameters or settings are approved and automatically transmitted) into the subject's therapy device. The present invention further relates to a system for screening patients to determine if they are viable candidates for certain therapy modalities. The present invention still further provides methods of quantifying movement disorders for the treatment of patients who exhibit symptoms of such movement disorders including, but not limited to, Parkinson's disease and Parkinsonism, Dystonia, Chorea, and Huntington's disease, Ataxia, Tremor and Essential Tremor, Tourette syndrome, stroke, and the like. The present invention yet further relates to methods of automatically and intelligently tuning a therapy device using objective quantified movement disorder symptom data acquired by a movement disorder diagnostic device with the therapy setting or parameters to be provided to the subject via his or her therapy device.

The movement disorder diagnostic device, systems and/or methods of the various embodiments of the present invention are used to screen patients, analyze, score, and treat various disorders, and especially movement disorders and mental health disorders. Movement disorders for purposes of this application include but are not limited to Parkinson's disease and Parkinsonism, Dystonia, Chorea, and Huntington's disease, Ataxia, Tremor and Essential Tremor, Tourette syndrome, stroke, and the like. Mental health disorders include, but are not limited to major depression, bipolar disorder, obsessive compulsive disorder, and antisocial disorders. Some of the treatments used for these disorders involve pharmaceutical interventions, fetal cell transplants, surgery, or deep brain stimulation. The efficacy of an intervention is often judged by the intervention's ability to alleviate subject symptoms and improve subject quality of life. The subject on which the system or method is used is a human or another form of animal.

The movement disorder diagnostic device the various embodiments of the present invention are preferably portable. By portable it is meant among other things that the device is capable of being transported relatively easily. Relative ease in transport means that the device can be carried by a single person, generally in a carrying case to the point of use or application. Additionally, relative ease in transport means that the device is easily worn, carried by or attached to a subject. Furthermore the device preferably should be relatively light-weight. By relatively lightweight, preferably the device weighs less than about 3 lbs., more preferably less than about 2 lbs., even more preferably less than about 1 lb., still more preferably less than about 0.5 lbs., still preferably less than about 2 ounces and most preferably less than 0.5 ounces. By being lightweight and further compact, the device should gain greater acceptance for use by the subject. The system for measuring and calculating the severity of the symptoms including external computers preferably weighs less than about 15 lbs., more preferably less than about 10 lbs., still more preferably less than about 5 lbs., even more preferably less than about 2 lbs., and most preferably less than 0.5 lbs. This system more preferably can fit in a reasonably sized carrying case so the patient or their caregiver can easily transport the system.

Another advantage of the systems and methods of the present invention is the ability to determine or calculate the severity of a subject's symptoms in real time. Throughout this disclosure, by real time it is meant that within 30 minutes of sensing and measurement the severity of a subject's symptoms can be calculated or determined. Real time, more preferably means that the subject's symptoms can be calculated or determined in less than about 30 seconds, more preferably in less than about 1 second, even more preferably in less than about 0.1 seconds, and most preferably in less than about 0.01 seconds.

The devices of the various embodiments of the present invention can form part of a system for use by a physician, veterinarian, technician or clinician for analysis or evaluation of a subject's movement disorder; for pharmaceutical research, for adjustment of neurostimulation therapy such as for example deep brain stimulation (DBS) or spinal cord stimulation (SCS), or for delivery of pharmaceutical compounds. Other elements of this system may include but are not limited to receivers, routers, communication devices, processors, displays, drug delivery devices and the like, some of which are described further in various embodiments described in more detail below.

The movement disorder diagnostic device, described in greater detail below, worn, carried by or attached to the subject, contains various physiological or movement sensor (s) used to measure the subject's external body motion and/or other physiological signals from the subject's body. The movement disorder diagnostic device may temporarily store the subject's movement or physiological data in onboard memory and/or transmit this data to an external device. In some embodiments, the movement disorder diagnostic device may directly transmit the data to a centralized database, to multiple databases at the same or multiple locations, or to a cloud-based database where the data can be stored and accessed essentially immediately by authorized users who can analyze and/or further process the data, use it to diagnose or assess the subject's symptoms or disorders, or the like. Additionally, or alternatively, the movement disorder diagnostic device can transmit the movement or physiological data to an external computer device, or directly to a remote location for access by a clinician, physician or technician. Transmission to a remote location may include transmission directly to such a computer device at said remote location, or may involve a user (such as a clinician, physician or technician) at the remote location accessing the data or information through the database or databases as described. The computer device, though called a tablet herein, is understood to be any type of device known to those skilled in the art usable for the intended purpose(s) or function(s), including, but not limited to, desktop computers, laptop computers, tablet computers, personal digital assistants (PDAs, "smart" cellular telephones, and the like). The computer device, or tablet, may be provided as part of the present invention's system, but in many embodiments the movement disorder diagnostic device is designed to work with and communicate with such devices of any third-party manufacturer or provider who provides such devices for the intended function or purpose of the present invention. In such cases, a software installation providing the user interface, tuning map capabilities, diagnostic and analysis tools, and the like would simply be installed on the third-party computer device or tablet as software or an application (or "app"), or the interaction with the user(s) can be web based through a web portal. The tuning map is one example of a tool that allows the clinician, physician or technician to review and/or determine the next, or preferably best (optimized) therapeutic settings or parameters for the subject's therapy device, such as a DBS device. The tuning maps are described in greater detail in U.S. patent application Ser. Nos. 13/861,790 and 13/153,063, both of which are herein incorporated by reference. Once the next therapy parameters or settings have been determined, a programmer device or unit can be used to communicate directly with the therapy device. Again, the programmer device or unit may be integrated into the subject-worn diagnostic device, a separate unit in and of itself, or may be part of the tablet or computer, and automatically communicates the parameters or settings to the programmer device or unit or directly to the subject's therapy device.

As noted, various embodiments of the present invention may include a sensor for measuring a subject's external body motion. The invention may also include at least one sensor for indirectly measuring movement metrics. Many types of sensors are known by those skilled in the art for measuring external body motion or providing physiological signals through which body movement information may be derived. External body motion sensors include but are not limited to accelerometers, gyroscopes, magnetometers, resistive bend sensors, combinations thereof, and the like. Preferably, a combination using at least an accelerometer and gyroscope is used. Sensors through which body movement information may be derived include, but are not limited to, electromyogram (EMG), electrooculogram (EOG), electroencephalogram (EEG), electrocardiogram (EKG), or other physiological signals which can directly or indirectly measure movement metrics in the subject may be included if such sensors and signals may be used to sense, detect, measure, and/or quantify the subject's external body motion, or related aspects.

In embodiments where a gyroscope is a sensor of the present invention, the gyroscope functions on the principle of the Coriolis Effect and a capacitive-based sensing system. Rotation of the sensor causes a shift in response of an oscillating silicon structure resulting in a change in capacitance. A typical application specific integrated circuit (ASIC), manufactured using a standard complementary metal oxide semiconductor (CMOS) manufacturing process, detects and transforms changes in capacitance into an analog output voltage, which is proportional to angular rate. The sensor element design utilizes differential capacitors and symmetry to significantly reduce errors from acceleration and off-axis rotations.

In embodiments where an accelerometer is a sensor of the present invention, it may optionally be a dual axis acceleration measurement system on a single monolithic integrated circuit (IC). Such embodiments may contain a polysilicon surface-micromachined sensor and signal conditioning circuitry to implement open-loop acceleration measurement architecture. For each axis an output circuit converts the analog signal to a duty cycle modulated (DCM) digital signal that can be decoded with a counter/timer port on a microprocessor. The dual axis accelerometer is capable of measuring both positive and negative accelerations. The sensor may be a surface micromachined polysilicon structure built on top of the silicon wafer. Polysilicon springs suspend the structure over the surface of the wafer and provide a resistance against acceleration forces. Deflection of the structure is measured using a differential capacitor that consists of independent fixed plates and central plates attached to the moving mass. The fixed plates are driven by 180-degree out of phase square waves. Acceleration will deflect the beam and unbalance the differential capacitor, resulting in an output square wave whose amplitude is proportional to acceleration. Phase sensitive demodulation techniques are then used to rectify the signal and determine the direction of the acceleration. The output of the demodulator drives a duty cycle modulator (DCM) stage through a 32 kOhm resistor. At this point a pin is available on each channel to allow the user to set the signal bandwidth of the device by adding a capacitor. This filtering improves measurement resolution and helps prevent aliasing. After being low-pass filtered, the analog signal is converted to a duty cycle modulated signal by the DCM stage. A single resistor sets the period for a complete cycle (T2). A 0 g acceleration produces a nominally 50% duty cycle. The acceleration signal can be determined by measuring the length of the T1 and T2 pulses with a counter/timer or with a polling loop using a low cost microcontroller.

In preferred embodiments, a single sensor unit comprising at least an accelerometer and a gyroscope may be used. More preferably, a single chip containing both a 3-axis accelerometer and a 3-axis gyroscope (e.g., Invensense MPU-6000), may be used. The sensor unit preferably not only comprises at least an accelerometer and a gyroscope, but also allows for integration of other sensors external to the sensor unit. Preferably, the accelerometer and gyroscope are each three-axis sensors capable of measuring their respective movements (acceleration and orientation) in each of the three dimensions of movement (X, Y and Z). Each of the accelerometer and gyroscope may output a separate signal for their respective measurements in each axis, and these signals are all converted from analog to digital by a bank of analog-to-digital converters (ADC). The separate ADCs for each axis of the accelerometer and gyroscope allow for simultaneous sampling of each sensor and eliminate the need for an external multiplexer. Preferably the sensor unit as a whole, and the accelerometer and gyroscope in particular are capable of operation with low power consumption. Preferably, the accelerometer and gyroscope are user-programmable such that the user may define an operating range in which the sensors will work (e.g., the accelerometer may be programmed to operate from as low as ±2 g to as high as ±16 g, and the gyroscope from as low as ±250 degrees/second to as high as ±2000 degrees/second). Some embodiments may include other sensors integrated into the sensor unit as well, for example, a temperature sensor which may be used to monitor the temperature of the sensor unit and ensure it is operating properly and under safe conditions.

The sensor unit further preferably comprises a digital motion processor (DMP) which may perform some preprocessing or processing of the sensor signals using motion-related algorithms. The digital motion processor at least preprocesses and/or processes the accelerometer and gyroscope signals to begin the analysis of the signals and to decrease the processing load on the external processor. Many embodiments may include external or additional sensors that are not housed within the sensor unit, but whose signals are transmitted to the sensor unit for integration with the accelerometer and gyroscope signals for further transmission to external components such as a processor. Such external or additional sensors may include, but are not limited to, force sensors, magnetometers, pressure sensors, bend sensors, combinations thereof, and the like. These external or additional sensors communicate with the sensor unit by means of an auxiliary communications interface. The digital motion processor can integrate the signal(s) from these external or additional sensors along with the accelerometer and gyroscope signals and perform preprocessing or processing of all of the signals together, thus further streamlining the data acquisition process and reducing the workload of the external processor (not shown).

In many embodiments, the movement disorder diagnostic device comprises a kinetic sensor board (or subject worn external sensor). The kinetic sensor board is preferably configured with at least an accelerometer and a gyroscope for quantifying the subject's motion. In some embodiments, the kinetic sensor board comprises at least three gyroscopes and three orthogonal accelerometers, but in more preferable embodiments the three of each sensor are replaced by at least one 3-axis accelerometer and at least one 3-axis gyroscope. The kinetic sensor board also includes a microprocessor and a power interface section.

In many embodiments, the electrical components of the movement disorder diagnostic device further include a power receiver. The power receiver is the component which receives the electrical charge from the external power source (not shown). The external power source can be any device for supplying power to the movement disorder diagnostic device. In some embodiments, the external power source may be a docking station to which the movement disorder diagnostic device can be connected, attached, docked, or placed into whereby a physical connection is made between the docking station and the movement disorder diagnostic device thus allowing power to be transferred via the physical connection. In other embodiments, the external power source may merely involve plugging the movement disorder diagnostic device into a traditional power outlet. In still other embodiments, the external power source may be an inductive charging mat or pad onto which the movement disorder diagnostic device is placed and power may be inductively transferred between induction coils in the charging mat or pad and the inductive coils in the power receiver of the movement disorder diagnostic device, as described herein. As the power receiver, which may be wireless or wired depending on the embodiment, receives power, it transfers said power to a power manager which controls and directs where the incoming power is delivered. If the movement disorder diagnostic device is not being presently used to measure a subject's body movements and is instead being charged, then the power manager directs the incoming power to the device's battery for charging. It might be possible, though not necessarily preferred, for some embodiments to allow charging while the unit is being used to measure a subject's body motions, in which case the power manager would direct the incoming power to either the battery or to the micro-controller for powering the device's operation for testing. However, it is more preferable for the device, during operation for testing, to be untethered and not in charging mode, and thus the battery would provide power to the unit for usage and testing purposes. The micro-controller or microprocessor is the internal processing unit that directs the other components to function. Thus, the micro-controller or microprocessor directs the power manager on where to direct the power it is receiving from either the power receiver or the battery. An electronic clock operates as commonly known in the art to control synchronization and operation of the device to maximize efficiency of power usage. The radio of the device controls and carries out communications between the device components, and between the movement disorder diagnostic device and external devices (not shown). The radio receives power directly from the power manager. As described herein, the radio may be a Bluetooth® communications device to provide wireless communications with external components such as computers or processors, data acquisition circuitry, internet or cloud-based memory banks or databases, and the like, as well as internal components such as the internal movement disorder diagnostic device memory, microprocessor, and the like. Both internal (between electrical components of the subject-worn sensor device) and external (between the subject-worn sensor device and external components or devices) communications may also be transmitted through wireless, wired, or a combination of both methods. The micro-controller comprises algorithms and protocols for coordinating the operation of at least these internal electrical components, and in some embodiments also for preprocessing or processing sensor data.

The movement disorder diagnostic device of the present invention further preferably comprises a transceiver module, or command module. Preferably the sensor unit and transceiver/command module are enclosed in the same housing constituting a single unit, though they may be separate units. The transceiver module includes communications electronics, such as a Bluetooth® radio (e.g., BlueGiga WT12) to provide wireless communications with the patient PC, on board memory, a microprocessor (e.g., Silicon Labs C8051F930), and a battery power supply (e.g., Kokam Lithium Power battery) that supplies power to both the transceiver module and one or more sensor modules. The transceiver module may also include a USB port to provide battery recharging and serial communications with the patient PC. The transceiver module may also include a push button input.

In many embodiments, the transceiver/command module contains one or more electronic components such as a microprocessor for detecting both the signals from the gyroscopes and accelerometers. Optionally, the one or more electronic components also filter the kinetic motion signals, and more preferably convert these signals, which are in an analog form into a digital signal for transmission to a remote receiving unit, computer or other similar device. Though, more preferably, the device uses the herein described 3-axis accelerometer and 3-axis gyroscope chip which comprises ADC circuitry and thus outputs a digital signal. The one or more electronic components are attached to the subject as part of the movement disorder diagnostic device. Further preferably, the one or more electronic components can receive a signal from the remote receiving unit or other remote transmitters. The one or more electronic components may include circuitry for but are not limited to, for example, electrode amplifiers, signal filters, analog to digital converter, Bluetooth® radio or other receiver, transmitter or transceiver components, a DC power source and combinations thereof. The one or more electronic components may comprise one processing chip, multiple chips, single function components or combinations thereof, which can perform all of the necessary functions of detecting a kinetic or physiological signal from the electrode, storing that data to memory, uploading data to a computer through a serial link, transmitting a signal corresponding to a kinetic or physiological signal to a receiving unit and optionally receiving a signal from a remote transmitter. These one or more electronic components can be assembled on a printed circuit board or by any other means known to those skilled in the art including but not limited to an ASIC chip. Preferably, the one or more electronic components can be assembled on a printed circuit board or by other means so its imprint covers an area less than 4 in$^2$, more preferably less than 2 in$^2$, even more preferably less than 1 in$^2$, still even more preferably less than 0.5 in$^2$, and most preferably less than 0.25 in$^2$.

Preferably, the circuitry of the one or more electronic components is appropriately modified so as to function with any suitable miniature DC power source. More preferably, the DC power source is a battery. The most preferred battery of the present invention is lithium powered batteries. Lithium ion batteries offer high specific energy (the number of given hours for a specific weight), which is preferable. Additionally, these commercially available batteries are readily available and inexpensive. Other types of batteries include but are not limited to primary and secondary batteries. Primary batteries are not rechargeable since the chemical reaction that produces the electricity is not reversible. Primary batteries include lithium primary batteries (e.g., lithium/thionyl chloride, lithium/manganese dioxide, lithium/carbon monofluoride, lithium/copper oxide, lithium/iodine, lithium/silver vanadium oxide and others), alkaline primary batteries, zinc-carbon, zinc chloride, magnesium/manganese dioxide, alkaline-manganese dioxide, mercuric oxide, silver oxide as well as zinc/air and others. Rechargeable (secondary) batteries include nickel-cadmium, nickel-zinc, nickel-metal hydride, rechargeable zinc/alkaline/manganese dioxide, lithium/polymer, lithium-ion and others.

In some preferred embodiments, the system is capable of inductive charging whereby an electromagnetic field is used to transfer energy from a charging mat or pad to the device. Preferably in such embodiments, the charging mat or pad comprises and induction coil that is used to create an alternating electromagnetic field. When the device, also comprising an induction coil, is placed on the charging mat or pad, the devices induction coil draws power from the electromagnetic field created by the charging mat's or pad's induction coil. The device's then converts this drawn power from electromagnetic field energy into electrical current and uses this electrical current to charge the device's battery.

Optionally, the data acquisition circuitry is designed with the goal of reducing size, lowering (or filtering) the noise, increasing the DC offset rejection and reducing the system's offset voltages. The data acquisition circuitry may be constrained by the requirements for extremely high input impedance, very low noise and rejection of very large DC offset and common-mode voltages, while measuring a very small signal of interest. Additional constraints arise from the need for a "brick-wall" style input protection against ESD and EMI. The exact parameters of the design, such as input impedance, gain and passband, can be adjusted at the time of manufacture to suit a specific application via a table of component values to achieve a specific full-scale range and passband.

Also optionally, a low-noise, lower power instrumentation amplifier is used. The inputs for this circuitry is guarded with preferably, external ESD/EMI protection, and very high-impedance passive filters to reject DC common-mode and normal-mode voltages. Still more preferably, the instrumentation amplifier gain can be adjusted from unity to approximately 100 to suit the requirements of a specific application. If additional gain is required, it preferably is provided in a second-order anti-bias filter, whose cutoff frequency can be adjusted to suit a specific application, with due regard to the sampling rate. Still yet more preferably, the reference input of the instrumentation amplifier is tightly controlled by a DC cancellation integrator servo that uses closed-loop control to cancel all DC offsets in the components in the analog signal chain to within a few analog-to digital converter (ADC) counts of perfection, to ensure long term stability of the zero reference.

Further optionally, where analog signals are acquired, such signals are converted to a digital form. This can be achieved with an electronic component or processing chip through the use of an ADC. More preferably, the ADC restricts resolution to 16-bits due to the ambient noise environment in such chips. Despite this constraint, the ADC remains the preferable method of choice for size-constrained applications such as with the present invention unless a custom data acquisition chip is used because the integration reduces the total chip count and significantly reduces the number of interconnects required on the printed circuit board.

Preferably, the circuitry of the sensor board comprises a digital section. More preferably, the heart of the digital section of the sensor board is a micro-controller or processor. The microcontroller or processor preferably contains sufficient data and program memory, as well as peripherals which allow the entire digital section to be neatly bundled into a single carefully programmed processing chip. Still more preferably, the onboard counter/timer sections are used to produce the data acquisition timer.

Preferably, the circuitry for the one or more electronic components is designed to provide for communication with external quality control test equipment prior to sale, and more preferably with automated final test equipment. In order to supply such capability without impacting the final size of the finished unit, one embodiment is to design a communications interface on a separate printed circuit board (PCB) using the SPI bus with an external UART and level-conversion circuitry to implement a standard serial interface for connection to a personal computer or some other form of test equipment. The physical connection to such a device requires significant PCB area, so preferably the physical connection is designed to keep the PCB at minimal imprint area. Optionally, the physical connection is designed with a break-off tab with fingers that mate with an edge connector. This allows all required final testing and calibration, including the programming of the processing chip memory, can be carried out through this connector, with test signals being applied to the analog inputs through the normal connections which remain accessible in the final unit. By using edge fingers on the production unit, and an edge connector in the production testing and calibration adapter, the system can be tested and calibrated without leaving any unnecessary electronic components or too large a PCB imprint area on the final unit. More preferably, no break-off tabs are required where a pogo-pin test pad design is used allowing the PCB to be tested without breaking apart.

Preferably, the circuitry for the one or more electronic components comprises nonvolatile, rewriteable memory for storing kinematic data, as well as RAM used to store operational data such as the pending mode (i.e., sleep or test mode), period and number of seconds to record data, daily alarm time, amount of time to collect data, and the like. Preferably, enough nonvolatile memory is included to record at least 8 hours of kinematic data, though preferably more. Alternatively, if the circuitry for the one or more electronic components doesn't comprise nonvolatile, rewriteable memory then an approach should be used to allow for reprogramming of the final parameters such as radio channelization and data acquisition and scaling. Without nonvolatile, rewriteable memory, the program memory can be programmed only once. Therefore one embodiment of the present invention involves selective programming of a specific area of the program memory without programming the entire memory in one operation. Preferably, this is accomplished by setting aside a specific area of program memory large enough to store several copies of the required parameters. Procedurally, this is accomplished by initially programming the circuitry for the one or more electronic components with default parameters appropriate for the testing and calibration. When the final parameters have been determined, the next area is programmed with these parameters. If the final testing and calibration reveals problems, or some other need arises to change the values, additional variations of the parameters may be programmed. The firmware of various embodiments of the present invention scans for the first blank configuration block and then uses the value from the preceding block as the operational parameters. This arrangement allows for reprogramming of the parameters up to several dozen times, with no size penalty for external EEPROM or other nonvolatile RAM. The circuitry for the one or more electronic components has provisions for in-circuit programming and verification of the program memory, and this is supported by the breakoff test connector, as well as the pop-pin test pad. The operational parameters can thus be changed up until the time at which the test connector is broken off just before shipping the final unit. Thus the manufacturability and size of the circuitry for the one or more electronic components is optimized. Most preferably, however, the system is designed to allow for over-the-air programming even once the circuit design has been completed and the circuit has been installed into the movement disorder diagnostic device. In such embodiments, the firmware contains a boot-loading program that, once turned on, looks for programming signals. Thus, such programming signals can be delivered and the device updated, even after manufacture and shipment to a clinic, or even when in the possession of a subject.

Preferably the circuitry of the one or more electronic components includes an RF transmitter and/or an RF receiver, or a RF transceiver. Still more preferably the circuitry of the one or more electronic components includes a Bluetooth® radio system requiring an average of about 42 mA of electrical current to operate. Another feature of the circuitry of the one or more electronic components preferably is an antenna. The antenna, preferably, is integrated in the rest of the circuitry. The antenna can be configured in a number of ways, for example as a single loop, dipole, dipole with termination impedance, logarithmic-periodic, dielectric, strip conduction or reflector antenna. The antenna is designed to include but not be limited to the best combination of usable range, production efficiency and end-system usability. Preferably, the antenna consists of one or more conductive wires or strips, which are arranged in a pattern to maximize surface area. The large surface area will allow for lower transmission outputs for the data transmission. The large surface area will also be helpful in receiving high frequency energy from an external power source for storage. Optionally, the radio transmissions of the present invention may use frequency-selective antennas for separating the transmission and receiving bands, if a RF transmitter and receiver are used on the electrode patch, and polarization-sensitive antennas in connection with directional transmission. Polarization-sensitive antennas consist of, for example, thin metal strips arranged in parallel on an insulating carrier material. Such a structure is insensitive to or permeable to electromagnetic waves with vertical polarization; waves with parallel polarization are reflected or absorbed depending on the design. It is possible to obtain in this way, for example good cross polarization decoupling in connection with linear polarization. It is further possible to integrate the antenna into the frame of a processing chip or into one or more of the other electronic components, whereby the antenna is preferably realized by means of thin film technology. The antenna can serve to just transfer data or for both transferring data to and for receiving control data received from a computer device and/or receiving unit which can include but is not limited to a wireless relay, a computer or a processor system. Optionally, the antenna can also serve to receive high-frequency energy (for energy supply or supplement). In any scenario, only one antenna is required for transmitting data, receiving data and optionally receiving energy. Optionally, directional couples can be arranged on the transmitter outputs of the electrode patch and/or the computer device and/or receiving unit. The couplers being used to measure the radiated or reflected radio wave transmission output. Any damage to the antenna (or also any faulty adaptation) thus can be registered, because it is expressed by increased reflection values.

An additional feature of the present invention is an optional identification unit. By allocating identification codes—a patient code, the computer device and/or receiving unit is capable of receiving and transmitting data to several subjects, and for evaluating the data if the computer device and/or receiving unit is capable of doing so. This is realized in a way such that the identification unit has control logic, as well as a memory for storing the identification codes. The identification unit is preferably programmed by radio transmission of the control characters and of the respective identification code from the programming unit of the computer device and/or receiving unit to the patient worn unit. More preferably, the unit comprises switches as programming lockouts, particularly for preventing unintentional reprogramming.

In any RF link, errors are an unfortunate and unavoidable problem. Analog systems can often tolerate a certain level of error. Digital systems, however, while being inherently much more resistant to errors, also suffer a much greater impact when errors occur. Thus the present invention, when used as a digital system, preferably includes error control sub architecture. Preferably, the RF link of the present invention is digital. RF links can be one-way or two-way. One-way links are used to just transmit data. Two-way links are used for both sending and receiving data.

If the RF link is one-way error control, then this is preferably accomplished at two distinct levels, above and beyond the effort to establish a reliable radio link to minimize errors from the beginning. At the first level, there is the redundancy in the transmitted data. This redundancy is performed by adding extra data that can be used at the computer device and/or receiving unit or at some station to detect and correct any errors that occurred during transit across the airwaves. This mechanism known as Forward Error Correction (FEC) because the errors are corrected actively as the signal continues forward through the chain, rather than by going back to the transmitter and asking for retransmission. FEC systems include but are not limited to Hamming Code, Reed-Solomon and Golay codes. Preferably, a Hamming Code scheme is used. While the Hamming Code scheme is sometimes maligned as being outdated and underpowered, the implementation in certain embodiments of the present invention provides considerable robustness and extremely low computation and power burden for the error correction mechanism. FEC alone is sufficient to ensure that the vast majority of the data is transferred correctly across the radio link. Certain parts of the packet must be received correctly for the receiver to even begin accepting the packet, and the error correction mechanism in the computer device and/or receiving unit reports various signal quality parameters including the number of bit errors which are being corrected, so suspicious data packets can be readily identified and removed from the data stream.

Preferably, at a second, optional level, an additional line of defense is provided by residual error detection through the use of a cyclic redundancy check (CRC). The algorithm for this error detection is similar to that used for many years in disk drives, tape drives, and even deep-space communications, and is implemented by highly optimized firmware within the electrode patch processing circuitry. During transmission, the CRC is first applied to a data packet, and then the FEC data is added covering the data packet and CRC as well. During reception, the FEC data is first used to apply corrections to the data and/or CRC as needed, and the CRC is checked against the message. If no errors occurred, or the FEC mechanism was able to properly correct such errors as did occur, the CRC will check correctly against the message and the data will be accepted. If the data contains residual errors (which can only occur if the FEC mechanism was overwhelmed by the number of errors), the CRC will not match the packet and the data will be rejected. Because the radio link in this implementation is strictly one-way, rejected data is simply lost and there is no possibility of retransmission.

More preferably, the RF link utilizes a two-way (bi-directional) data transmission. By using a two-way data transmission the data safety is significantly increased. By transmitting redundant information in the data emitted by the electrodes, the computer device and/or receiving unit is capable of recognizing errors and request a renewed transmission of the data. In the presence of excessive transmission problems such as, for example transmission over excessively great distances, or due to obstacles absorbing the signals, the computer device and/or receiving unit is capable of controlling the data transmission, or to manipulate on its own the data. With control of data transmission it is also possible to control or re-set the parameters of the system, e.g., changing the transmission channel. This would be applicable for example if the signal transmitted is superimposed by other sources of interference then by changing the channel the computer device and/or receiving unit could secure a flawless and interference free transmission. Another example would be if the signal transmitted is too weak, the computer device and/or receiving unit can transmit a command to increase its transmitting power. Still another example would be the computer device and/or receiving unit to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements. This also reduces the energy requirements, thereby providing longer battery life. Another advantage of a two-way, bi-directional digital data transmission lays in the possibility of transmitting test codes in order to filter out external interferences such as, for example, refraction or scatter from the transmission current. In this way, it is possible to reconstruct falsely transmitted data.

The computer device and/or receiving unit of various embodiments of the present invention can be any device known to receive RF transmissions used by those skilled in the art to receive transmissions of data. The computer device and/or receiving unit, by way of example but not limitation, can include a communications device for relaying the transmission, a communications device for re-processing the transmission, a communications device for re-processing the transmission then relaying it to another computer device and/or receiving unit, a computer with wireless capabilities, a PDA with wireless capabilities, a processor, a processor with display capabilities, a desktop computer, laptop computer, tablet computer, smart phone, and combinations of these or like devices. Optionally, the computer device and/or receiving unit can further transmit data both to another device and/or back. Further optionally, two different computer devices and/or receiving units can be used, one for receiving transmitted data and another for sending data. For example, with the movement disorder diagnostic system of the present invention, the computer device and/or receiving unit of the present invention can be a wireless router, which establishes a broadband Internet connection and transmits the physiological signal to a remote Internet site for analysis, preferably by the subject's physician. Another example is where the computer device and/or receiving unit is a PDA, computer, tablet or cell phone, which receives the physiological data transmission, optionally re-processes the information, and re-transmits the information via cell towers, land phone lines or cable to a remote site for analysis. Another example is where the computer device and/or receiving unit is a computer or processor, which receives the data transmission and displays the data or records it on some recording medium, which can be displayed or transferred for analysis at a later time.

The digitized kinetic or physiological signal is then transmitted wirelessly to a computer device and/or receiving unit. This computer device and/or receiving unit allows the subject wide movement. Preferably, the computer device and/or receiving unit can pick up and transmit signals from distances of greater than about 5 feet from the subject, more preferably greater than about 10 feet from the subject, even more preferably greater than about 20 feet from the subject, still even more preferably greater than about 50 feet from the subject, still even more preferably greater than about 200 feet from the subject, and most preferably greater than about 500 feet from the subject. The computer device and/or receiving unit is used to re-transmit the signal based in part from the movement or physiological signal from the movement disorder diagnostic device wirelessly or via the internet to another monitor, computer or processor system. This allows the clinician or monitoring service to review the subject's movement or physiological signals and if necessary to make a determination, which could include modifying the patients treatment protocols.

Optionally, the system of the present invention includes some form of instruction, which can be in written form on paper or on a computer monitor, on a video, or communicated via teleconference or video conference between the subject and clinician, physician or technician. Optionally, a video is used which instructs the subjects to perform a series of tasks during which their kinetic motion and/or EMG and/or other physiological signals related to their motion can be measured. Since the system of the present invention is preferably used in the subject's home, a video giving directions and/or describing various tasks to be performed by the subject is included with the system. The video may be accessed or viewed for example but not by way of limitation through use of video tape, DVD, podcast as part of computer software provided, through the internet, or the like. The directions could include but are not limited to instructions on how to don the device, how to turn the device on, and the like. The description of various tasks could include but is not limited to exercises which are typically used by a technician, clinician or physician to evaluate a subject with a movement disorder including but not limited to hand grasps, finger tapping exercises, other movements and the like. One embodiment of a video includes the technician, clinician or physician looking into the camera, as they would a patient, and instructing them on device setup, instructing the patients through each of the tasks to be performed, providing verbal encouragement via video after a task, and asking subject's to repeat a task if it was not completed. Preferably, these video clips are edited and converted to MPEG or other similar file types either automatically or using editing software. For movement disorders such as Parkinson's disease preferably the technician, clinician or physician instructs the user through multiple tasks as per the UPDRS, tremor rating scale (TRS), or similar scale guidelines including tasks, movements, motions, activities, and the like designed or intended to analyze symptoms of movement disorders including, but not limited to, rest tremor, postural tremor, and action tremor, bradykinesia, rigidity, gait, dyskinesia, and the like. More preferably, if the video is linked to the user interface software, the software will automatically detect if a subject has performed the requested task and provide feedback through the video to either repeat the task or continue to the next task. Still more preferably, once the user has setup the device, it will continually record the subject's movement data (including before and after any directed video tasks), be able to quantify the severity of the subject's symptoms during activities of daily living, and communicate that information with the clinician and subject through interface software, video, or the like.

Also optionally, the subject may not be required or instructed to perform a specific task or group of tasks, but instead measurement and quantification of the subject's symptom(s) and side effect(s) may be carried out while the subject wears the diagnostic device during activities of daily living, or simply on a continuous basis. In other words, the subject may wear the diagnostic device while cleaning his or her home, doing yard work, cooking, exercising, dancing, or other similar activities that are normally performed naturally during the course of one's day. In such embodiments, measurements may be taken periodically according to a predetermined interval or start time, may be initiated by the subject based on the activity he or she is performing or is about to perform, may be initiated by the clinician, physician or technician either in-clinic or remotely, or the system may detect a change in activity or the onset of a symptom or side effect and may automatically perform the measurement, quantification and subsequent steps in order to adjust the therapy device automatically. Where the clinician, physician or technician initiates the process remotely, he or she may interrogate the system via electronic communication means and begin the process.

The present invention includes various methods of measuring and scoring the severity of a subject's movement disorder. These methods include a number of steps which may include but are not limited to measuring a subject's external body motion; transmitting wirelessly a signal based in part on the subject's measured external body motion; receiving the wirelessly transmitted signal; downloading data from memory; and scoring the severity of a subject's movement disorder based in part on the wirelessly transmitted or downloaded signal. Optionally, an electromyogram of the subject's muscle activity and/or other physiological signals may be obtained and used in part to score the severity of the subject's movement disorder.

Several preferred embodiments of the present invention include a trained scoring algorithm to determine and provide objective scoring from movement data acquired by the movement disorder diagnostic device. The trained scoring algorithm in part comprises a mathematical model or quantitative representation, used to process kinematic features computed from the movement data and may include some of those steps known to those skilled in the art. In some embodiments of the present invention, the scoring may done on a continuously variable scale of 0-4 with scores substantially similar to or predictive of scores that would be given on the Unified Parkinson's Disease Ratings Scale (UPDRS) by an expert clinician. ("Expert clinician" for the purposes of this application is taken to mean a doctor, nurse, researcher, or other medical or scientific professional trained for and sufficiently experienced in the task of interest, e.g., motor function assessment using the UPDRS, or DBS programming.)

The present invention also preferably includes DBS parameter control methods and tuning algorithms for determining and setting the DBS parameters used to deliver DBS therapy to the subject. In many embodiments, the parameter control methods and algorithms utilize a system of tuning maps, or other parameter display or visualization methods or tools, for DBS programming. Although the term 'tuning map' is used throughout this application, it is intended that tuning maps include any such method or tools that may be used for displaying therapy parameters or settings for human review and/or analysis. As noted herein, in the present invention, the tuning maps are preferably only utilized for optional clinician, physician or technician review of the second levels or optimized levels of therapy parameters or settings. The tuning maps utilized by the present invention are a tool used for recording DBS parameters, the subject's response to stimulation at those parameters, and allowing a clinician, physician or technician to optionally or periodically review parameters and settings. Preferably, when utilized, the tuning map is a two-dimensional representation of a three-dimensional graph or display of data.

The subject is first screened and determined to be a viable candidate for DBS therapy, and then has at least one DBS lead surgically implanted into his or her brain. The screening process preferably involves providing the subject with a diagnostic device for monitoring and assessing the subject's movement disorder systems. Generally, a DBS therapy system will include one or more implanted leads with each lead having one or more electrodes. These leads are connected to a pulse generator, which generally is also implanted with the leads. The pulse generator can be implanted in the cranium or in some cases wiring from the leads will be threaded down the subject's neck and the pulse generator will be implanted or embedded in the subject's upper chest or abdomen. The pulse generator will run on a battery, which can in some cases recharged through techniques such as inductive coupling. The DBS therapy system can be adjusted generally through communication between a programming module or unit and the impulse generator. Such a system, as an example, is described in U.S. patent application Ser. No. 12/818,819, filed on Jun. 18, 2010, which is hereby incorporated by reference. Other systems as known or later developed in the art can also be adjusted with the devices, method and systems of the present invention. Thus, because of the highly invasive nature of therapies such as DBS, requiring surgical implantation of the therapy device, the present invention provides the screening capabilities to ensure the subject would benefit from such a therapy before undergoing the costly and onerous surgical procedure.

The subject may utilize this device at home and during other normal life activities as well, or in a clinical setting, and during the performance of motor and cognitive tests, and while taking his or her prescribed medications for treatment and management of the movement disorder symptoms. The device monitors and records the occurrence of these symptoms and then analyzes the data by means of algorithm(s) designed to account for the multitude of variables including demographic information (age, gender, weight, blood pressure, physical activity, medication use, disease duration, Hoehn & Yahr, marital status/caregiver support, patient expectations, and the like), the type of anticipated DBS therapy (DBS target, unilateral/bilateral implant, constant current versus constant voltage, and the like), non-motor response (UPDRS parts I and II scores, cognition and quality of life assessments, neuropsychology tests, and the like), motor response (UPDRS parts III and IV scores), sensor recordings of symptom occurrence and severity, response to medication, and the like. Generally, subjects who respond favorably to typical medications tend to respond well to DBS therapy. The algorithm analyzes all of the data and makes a determination as to whether the patient is likely to be a good candidate for DBS therapy. The algorithm may optionally employ any one, or a combination of, statistical models currently known to those in the art, including, but not limited to linear and non-linear classification methods such as logistic regression, artificial neural networks, k-means clustering, and the like. The algorithm may output the determination in different ways. In some embodiments, particularly where the diagnostic device is used for screening a subject for viability of DBS therapy, the algorithm may provide a binary output indicating that the subject is or is not a good candidate for DBS, in other words a report or display that indicates a Go/No go result on whether the subject would or would not benefit from such therapy. In other embodiments, the algorithm may provide a percent likelihood of favorable DBS outcomes for the subject. Still other embodiments may present the multitude of data described above in a chart or graph format in order to allow a clinician, physician or technician to review the data and results and confirm or deny that the subject would benefit from such therapy. By way of non-limiting example, various embodiment may employ a visual display that depicts a pie chart wherein the pie chart is populated showing the measured and quantified occurrences of a symptom(s) such as tremor throughout the day. Any other method known to those skilled in the art for displaying the test results and optionally the input data, or combinations of both, can be envisioned for presenting the data to a clinician, physician or technician for optional review of the screening viability determination. Additionally, the algorithm may provide suggested DBS lead placements in the subject's brain based at least in part on the symptoms and side effects the subject experiences, their severity, and the like. If the subject is determined to be a favorable candidate, the clinician then initiates the process for DBS therapy, which begins with the surgical implantation of at least one DBS lead into the subject's brain. The main purpose of the screening process is to provide a pre-surgical indication of whether the subject would benefit from DBS therapy. This minimizes the likelihood of needless surgery and risk for the subject, as well as time, cost, and resources utilized.

For initial DBS tuning, it may be preferable to perform a monopolar review, which is using a single DBS contact in the monopolar configuration. However, bipolar, or greater, review may be accomplished as well with the present invention. A single DBS lead has several contact points, or electrodes, which can be used to administer the electrical stimulation. Typically, a DBS lead has at least one ground contact, and at least 3 battery contacts for delivering the electrical stimulation, though fewer or more battery contacts may be included. Once the lead, or leads, is implanted into the subject's brain, the subject then undergoes an initial programming session. During the initial programming session, a clinician enters a set of initial test variables (as described above), and administers the electrical impulse to the subject's brain. Typically, the initial test parameters are set and fixed, and then in later iterations the amplitude (voltage or current), as well as other variables are gradually increased or otherwise changed. The results of the impulse may be recorded in a tuning map for optional review indicating the effect which the given set of parameters had on the subject's symptoms, feelings, and the like, and are simultaneously communicated to the tuning algorithm(s). The subject is generally awake for the programming sessions and gives feedback to the clinician regarding any sensations or effects that the subject experiences. The results may include any sort of measured, observed, or calculated response, or combinations thereof including, but not limited to, sensor recordings (for quantifying symptoms as described above), patient responses and perceptions, clinician observations, and clinician scores (e.g., UPDRS, MDS-UPDRS, and the like). In some embodiments, it is possible that the tuning process may be entirely automated such that the tuning map is populated entirely by sensor recordings of the subject's response to the DBS therapy and no human observation or calculation is required. Based on the results of the initial test parameters, the tuning map is populated and the clinician then changes the parameters to more effectively address the subject's symptoms, and the process is repeated. Typically, the end result of the tuning process is to optimize the effectiveness of the therapy (i.e., decrease the severity and occurrence of symptoms as much as possible) while minimizing the volume of activated brain tissue, but the particular goals and needs of the subject will dictate exactly what the desired result is for each subject.

Generally, the process of generating a tuning map, or otherwise recording the test DBS parameters is done manually in writing or in a software package for record-keeping, and then those parameters are separately programmed into the DBS system to be administered to the subject. However, many embodiments of the present invention include an integrated system programming capability which alleviates the redundant, time-consuming steps of manually recording the parameters and separately programming them into the DBS system. The integrated system programming capability allows the clinician to perform the above tuning map population steps, and to determine the next iteration of parameters to use in the same manner. However, once the tuning map is populated, the clinician then enters the new parameters into the software which records them, and then the software automatically changes the DBS parameters which are administered to the subject. In other words, the integrated system programming capability integrates the DBS software and hardware together. This eliminates the need for two separate steps, minimizes the opportunity for human error either in recording incorrect parameter values, or in entering incorrect parameter values into the DBS system, and drastically decreases the amount of time required for the programming session, which improves the experience for the subject and clinician(s) alike.

Many embodiments of the present invention employ an intelligent system programming capability that greatly decreases the amount of clinician "guess-work" involved in selecting the iterations of DB S parameter values by providing an expert system that efficiently determines appropriate DBS settings. Similar to above, for the first postoperative programming session, the system performs an automated monopolar survey. The subject may wear a motion sensor unit comprising sensors for measuring movement, and performs motor assessments at various DBS settings. Stimulation is incrementally increased from zero at each contact until symptoms stop improving as measured by the motion sensor unit, perceptions, clinician observations or scores, or the like, or until side effects appear as measured by the motion sensor unit, the clinician, or the patient. In many embodiments, adjustments will be based on current rather than voltage since the functional response it often primarily related to the amount of current delivered to a specific target. For constant current IPGs, the current amplitude will be set directly and for constant voltage IPGs, the voltage amplitude may be set based on the required current and impedance measured on the electrode. Preferably, the system is capable of operating in either constant current or constant voltage modes, depending on the clinician's preference and the needs of the particular subject. The monopolar survey helps determine the functional anatomy around the DBS lead site and narrows the search space for determining an optimal set of programming parameters. A therapeutic window will be defined as the region in which a patient exhibits optimal symptomatic benefits without side effects. This therapeutic window will be valuable at the initial postoperative programming session as well as all future adjustment sessions for determining the current amplitude when side effects begin to occur on each contact. This therapeutic window is then used to define a side effect region. The system includes internal electric field modeling to determine how this side effect region can be avoided, possibly by shaping the electric field with a bi- or tripolar configuration or altering the pulse width. Bipolar or tripolar configuration refers to the simultaneous delivery of electrical impulses from two or three, respectively, contacts on the DBS lead to shape the electrical field delivered to the subject's brain. For monopolar stimulation, current falls off proportionally to the distance from the negative electrode contact. For bipolar stimulation, current decreases proportional to the square of the distance to the negative contact, but increases by the square of the distance between the negative and positive contacts. Efficient stimulation algorithms are used to find a set of parameters that optimize for efficacy while minimizing side effects and battery usage. The patient and/or clinician will be able to give higher weight to a given item, parameter, or symptom (e.g., tremor severity) that may be most important to him or her. Many clinicians are ignorant of the battery voltage of the IPG battery and therefore unaware that a slight increase of the stimulation amplitude above the battery voltage will activate voltage doubler or tripler circuits in the IPG, significantly increasing battery drain and shortening battery life by half. The algorithms will automatically avoid increasing voltage above the battery voltage unless necessary for finding a therapeutic window. After the automated monopolar survey is completed and a patient-specific functional map is developed during the initial postoperative programming visit, subsequent programming adjustments will be much simpler and faster.

Basing the algorithm(s) on functional, rather than structural, anatomy has several advantages. First, most DBS programmers are not imaging experts and may not have the wherewithal to correctly interpret complex anatomies. More importantly, the therapeutic mechanisms of DBS are largely unknown. The optimal stimulation location differs across patients and is based on functional rather than structural anatomy. Therefore, the system will be individualized to each subject's response and be far superior to recently developed DBS programming aids, which rely on anatomical assumptions, imaging, and statistical modeling to estimate the electric field at various anatomical targets.

The intelligent system programming capability takes the results of the initial test parameters and automatically populates the tuning map while simultaneously providing these results to an algorithm(s). The system's tuning algorithm(s) analyze these results and provide the next iteration of DBS parameters. These provided parameters or settings may be reviewed and possibly edited by the clinician, physician or technician, or may be automatically entered into the subject's therapy device thus programming the therapy device to operate according to those settings. Effectively, the system provides optimized DBS parameters or settings which either are automatically implemented, or may act as a guide for the clinician in setting the IPG for the next iteration of testing (particularly for the initial programming session). This reduces the clinician's need to perform the analysis and determine which parameters to change and how much to change them. The clinician may have the option to edit or elect any one or combination of the system's suggested parameters for the next iteration. This intelligent programming system may be performed in-clinic during a traditional programming appointment, whereby the system provides the suggested DBS parameters or settings to the clinician and the clinician can review and edit the parameters or settings through the software which in turn adjusts the settings and parameters on the IPG. Alternatively, the intelligent programming may take place remotely whereby the system automatically and intelligently provides optimized parameters or settings and programs them into the subject's therapy device, or communicates any data and suggested DBS parameter settings to the clinician, physician or technician who is located some distance away while the subject remains at home, and the clinician then reviews and elects to approve or edit the suggested settings, which are sent to the IPG to update the parameters of the DBS administered to the subject, or still further the clinician may instruct the diagnostic device to perform another iteration of testing, rather than editing the suggested parameters or settings herself. Where the clinician, physician or technician does perform the option or periodic review, the data (e.g., parameters and settings, test results, and the like) may be displayed for his or her review in a tuning map as described. Because the clinician is not required to be physically present at the time of programming, the system instead may rely on system and user reports, which are sent to the clinician. These reports may be made by the system sending reports to the clinician, video and/or audio conferences between the subject and the clinician, the subject keeping a medication diary to report medication schedules and symptom occurrence and severity, transmitted tuning maps, and the like.

Preferably, for the present invention wherein remote programming is performed with at least clinician, physician or technician review, the system additionally provides the clinician, physician or technician the ability to manually make the determination as to what therapy parameters to use with the subject's therapy device based in part on the tuning map or data corresponding to the subject's measured and quantified motor symptoms or based on other data measured by the movement disorder diagnostic device from the subject. The present invention further optionally allows the clinician, physician or technician the ability to review recommended second level therapy parameters before or after those therapy parameters or settings are entered into the therapy device and to change those recommended settings.

The present invention includes remote programming methods and capabilities utilizing a database, which may be cloud-based in some embodiments, allowing for remote DBS adjustments being possible without the subject even leaving his or her home, and in some intelligent embodiments without clinician involvement. The system may provide manual, semi-automated or automated, objective scoring and tuning remotely, and enable high-quality programming to all DBS recipients, regardless of proximity to expert programmers. Ideally, the subject would not have to travel to the clinic or facility for programming unless a problem was detected requiring personal medical care. Such embodiments necessarily include the integrated system programming capability whereby the software directly communicates with the hardware to set the DBS parameters according to the values entered into the software in order to enable the periodic or optional review by the clinician, physician or technician. For such optional or periodic review, rather than in-clinic programming sessions, the software would communicate with the DBS hardware, which is located remotely, implanted into the subject. In these embodiments, the implanted device may perform an intelligent system analysis, creating a suggested set of DBS parameters for the particular subject, and then securely communicate all the data and suggested parameters to a centralized or cloud-based database, which analyzes all the information and then sends programming commands to the subject's IPG to change the DBS settings. However, in non-intelligent/automated embodiments, the movement disorder diagnostic device would perform the measurements and recordings of movement-related data, and communicate that data without any suggested parameters to a remote location and/or database, and where the clinician, physician or technician then receives or accesses and analyzes the data and makes the determination as to the next parameters or settings to be used. This database remote system allows for continued or repeated DBS tuning without requiring the patient to travel to a clinician. The benefits of such a system go beyond the convenience of minimizing travel time and access to clinicians and include the ability to deliver such reports at virtually any time (the subject and clinician are not tied to a particular appointment time and window, and the clinician can review any data at any time if desired), continuous and repeated monitoring of the subject's and system's statuses, and delayed monitoring whereby results of changed parameters can be monitored later, which is particularly useful for symptoms that may not react to changes rapidly (i.e., during the normal clinical appointment time period).

Further, the system preferably includes the capability to perform hardware diagnostic tests remotely of any and all of the individual units or modules used with the present invention, including the subject's therapy device (e.g., implanted pulse generator), movement disorder diagnostic device, programmer unit, and the like. The hardware in such embodiments is able to monitor and/or periodically interrogate the system to detect changes in system conditions such as battery status, electrode impedance, and the like. The system then sends the results of these diagnostic tests back to the clinician who can monitor them to determine if a problem arises requiring the subject to return to the clinic for adjustments, repairs, or other such purposes. Further still, such embodiments using remote programming and control may include medication delivery systems as well. Such delivery systems include a drug reservoir for holding and storing medication, and infusion pump for delivering said medication from the reservoir to the subject. Such embodiments may determine based on recorded signals that the subject's symptoms are particularly severe or occurring more frequently.

Some embodiments may optionally include a closed-loop or semi-closed loop drug titration system. In such embodiments, when the subject's prescribed medication is initially taken or delivered, the system then monitors the subject's symptoms. The system continues to monitor the symptoms until and after it detects that the subject's symptoms increase, maintain, or only very slightly decrease in severity and rate of occurrence. In a semi-closed loop system, a report, warning, alert, or some other signal would then be sent to the subject or to the subject's clinician. In such case, the subject could take more medication, or the clinician could send a command for an integrated drug delivery pump to administer another dose. In a close-loop system, upon detection of the above indicators, the system would automatically administer an additional dose of medication through an integrated medication delivery pump. In either case, the system is capable of substantially continuous symptom monitoring to determine when the subject is experiencing an increase in symptom activity, ineffective medication delivery, or a wearing off of medication in order to administer additional medication to control the subject's symptoms. Further, such embodiments must also be able to monitor and detect the occurrence of side effects arising from the medication, and to stop administering medication when such side effects begin to manifest.

It will be further noted that use of the device and method of the present invention in combination with treatment directed at stopping or slowing the progression or onset of a movement disorder is intended to optionally include the use of the movement disorder monitoring device with a broad scope of pharmaceutical agents and/or other treatments directed at stopping or slowing the progression or onset of a movement disorder. Neuroprotective drugs provide one specific example of a compound that can be used to stop or slow the progression or onset of a movement disorder. Briefly stated, neuroprotective drugs include a broad set of compounds that serve to eliminate or reduce neuronal death in the central and/or peripheral nervous systems, hence eliminating certain movement disorder symptoms that can follow neuronal death and stopping progression or onset of a movement disorder disease. By way of specific example, in the case of PD certain drugs have been and are being examined and may be found to be effective at eliminating or reducing death of a subject's dopamine producing neurons, and the efficacy of such drugs over extended periods of time could be objectively monitored using the device and method of the present invention as a means to collect and review movement disorder symptom data over extended periods of time. By way of example, neuroprotective drugs that have been and are being examined for their potential in stopping or slowing the progression of movement disorders such as PD include drugs such as selegiline, riluzole and lazabemide. It is to be understood that the scope of the present invention is intended to cover the use, with the device and as part of the method of the present invention, of these drugs as well as other neuroprotective drugs that may yet be discovered or are currently under investigation.

The above systems, devices, and methods are further contemplated for use in treating various mental health disorders, particularly major depression, bipolar disorder, and obsessive compulsive disorder. In particular treatment of mental health disorders would benefit from the patient screening system and method for determining if the patient would benefit from DBS therapy in dealing with his or her disorder, as well as the integrated and intelligent programming systems and methods for both in-clinic and remote programming of the DBS device once implanted.

The Applicants herein incorporate the following U.S. Pat. Application Nos. by reference: Ser. No. 11/082,668 filed Mar. 17, 2005, and Ser. No. 11/432,583 filed May 11, 2006.

FIG. 1 illustrates the therapeutic device programming (or "tuning," or "parameter settings adjustment") process with one embodiment of the invention. A subject 1 has a therapy device (not shown), which in the illustrated case is a therapy device for the treatment of a movement disorder, such as an implanted DBS device. Subject 1 wears a movement disorder diagnostic device comprising a sensor unit 2 and a command module 3. The sensor unit 2 comprises at least one sensor(s), preferably a physiological or movement sensor(s), such as accelerometers and/or gyroscopes (both not shown), or other similar sensors, as well as a transmission system (not shown). In one preferred embodiment, the sensor unit 2 comprises three orthogonal accelerometers and three orthogonal gyroscopes, or more preferably at least one 3-axis accelerometer and at least one 3-axis gyroscope. Preferably, where the at least one sensor is an accelerometer and/or a gyroscope, these are micro-electrical-mechanical (MEMS) accelerometers or gyroscopes. In a preferred embodiment, a single chip containing both a 3-axis accelerometer and a 3-axis gyroscope is used, rather than using separate sensors. An example of such a combined sensor chip is the Invensense MPU-6000. The transmission system may be wired or wireless, and may communicate via any medium and any transmission protocol known to those skilled in the art. In the illustrated embodiment, the sensor unit 2 communicates sensor readings to a command module 3 over a small flexible transmission cable 4, though this transmission could also be conducted wirelessly. In the more preferred embodiment where both the sensor unit 2 and command module 3 are combined in a single housing constituting the entire movement disorder diagnostic device, the two modules may be integrated into the same electronics thus eliminating the need for wired or wireless communication between separate modules. In the illustrated embodiment, the sensor unit 2 is worn on the middle phalange of the middle finger and the command module 3 is worn on the wrist using a wristband, though the placement of the sensor unit 2 and command module 3 may vary depending upon the symptoms of the movement disorder. Alternate placements could include other fingers, the ankle, foot, shoulder, or elsewhere on the trunk of the body or on any part of any extremity. While the illustrated embodiment shows the sensor unit 2 and the command module 3 as having separate enclosures, permitting for a lighter-weight sensor unit 2 that is easily worn on the finger, in alternate embodiments the sensor unit 2 and command module 3 may be integrated into a single enclosure. In such embodiments where the sensor unit and command module are combined into a single enclosure forming the movement disorder diagnostic device, all components of each unit are enclosed or attached to the single enclosure, including, but not limited to the units and modules themselves, any power supply and communication electronics required for operation.

The command module 3 may provide numerous functions including, but not limited to supplying power to the sensor unit 2, storing data in memory, transmitting data. Preferably, it is controlled by firmware in processor, for example an Analog Devices ADuC7020 processor. The data acquisition (DAQ) section samples finger sensor unit data at 128 Hz for each of the six channels. Optional onboard memory preferably provides at least 12 hours of data storage. Some embodiments do not contain internal storage, but rather transmit the data substantially in real-time to a receiver unit 5, a centralized database (not shown) or to a cloud-based database (not shown). Still other embodiments utilize onboard, temporary data storage as well as substantially real-time data transmission to a receiver unit 5, centralized database (not shown) or a cloud-based database (not shown). A lithium-based battery provides at least 12 hours of continuous use and is rechargeable by a computer through a LEMO, or similar connector, to USB connector cable. The command module 3 also integrates a membrane switch label (not shown) with LED indicators for power and charging (not shown). Three membrane switches inside the label (not shown) provide on/off control and two subject diary inputs. The command module 3 may perform rudimentary signal processing, such as filtering and analog-to-digital conversion, on the movement signals received from the sensor unit 2 before transmitting the movement signals to a receiver unit 5. The receiver unit 5 may be of any type known to those skilled in the art, and useful for receiving data from the sensor unit and making it available to a clinician, physician or technician on computer device 6. The computer device 6 will be referred to as a tablet (or tablet computer), but it is meant to be understood that it may be any such similar device, including, but not limited to desktop computers, laptop computers, tablet computers, personal digital assistants (PDAs), "smart" cellular telephones, or the like. This transmission may be wired, but is preferably wireless, advantageously providing the subject the greater comfort and convenience of being untethered as well as endowing the system with enhanced safety and portability. The wireless link frees subject motion, which allows unimpeded and accurate assessment of subject symptoms. In an operating room, a small untethered system has the added benefits of reducing further subject discomfort and not impeding clinical traffic. A wireless system, which is not directly connected to any source of AC power, has the added benefit of reducing or eliminating risk of electrical shock. Preferably, the wireless transmission is robust and operates in a frequency band designated for hospital or clinical-setting use. Preferably, the wireless transmission radio is a Bluetooth radio operating in the 2.4 GHz band. More preferably, radio transmission occurs over the Wireless Medical Telemetry Service (WMTS), dedicated by the FCC to wireless medical equipment used in hospitals, which comprises the frequencies 608 to 614 MHz, 1395 to 1400 MHz and 1429 to 1432 MHz. Preferably, radio communication is accomplished using a mix of traditional heterodyning techniques along with newer software radio techniques. For example, receiver structure consists of a band select function of either 608-614 MHz or 1395-1432 MHz, followed by a heterodyning operation. The lower frequency band undergoes one frequency translation while the upper undergoes two frequency translations. For the low band (608-614 MHz) the signal is translated to 44 MHz where it is then sampled by an A/D converter and demodulated in the "sampled" domain. The high band is translated first to the lower frequency band (608-614 MHz) and processed in the same fashion. The software radio demodulation approach accommodates many different data rates and modulation formats and advantageously allows future radio upgrades to be implemented simply by changing the signal processing program opposed to necessitating an entire analog hardware redesign. The low band transmit signal is a simple frequency source modulated with appropriate information. For the high band transmit signal, the same signal used for the low band transmit signal is mixed with a high frequency signal to produce the desired output. For transmitter operation, the signal processing hardware generates the modulating signal for all different signal formats and data rates. The signal processing hardware outputs a modulating signal input to an oscillator circuit that creates the modulated transmit signal. The modulated signal, for the high band, uses the low band modulator and translates that signal to the proper operating frequency. Since the modulator is the same for both low and high bands it ensures the same signal quality regardless of operation band. Since the radio is a transceiver (two-way link), the design can serve as a master or slave; thus the same design can be employed in the command module 3 as well as in the receiver unit 5.

Data may also be collected in an on-board memory contained within the command module 3. Such onboard or internal memory may be used for temporary storage so that the data may be saved and then downloaded to the tablet computer 6 later, advantageously allowing the subject to wear the movement disorder diagnostic device comprising sensor unit 2 and command module 3 for more prolonged symptom monitoring. Additionally, or in the alternative, the onboard memory may be used to temporarily store the movement data and provide a backup in the event of halted, corrupted, or otherwise incorrect transmission of the data from the movement disorder diagnostic device comprising sensor unit 2 and command unit 3 to the receiving unit 5.

The receiver unit 5 may be, and is preferably integrated into some larger system—for example, it may consist of a wireless receiver, such as a Bluetooth receiver, integrated into a device such as a laptop or tablet computer, a cellular phone, etc.—or it may be a separate device built into an enclosure. However, in the illustrated embodiment, the receiver unit 5 is connected to a tablet computer 6 via one of the USB ports (not shown, in a dongle-style connection that advantageously eliminates a cable), is powered thereby, and comprises a radio frequency transceiver capable of 2-way radio frequency communication with the command module 3. Power regulation and USB-based data transmission protocols may be among any known in the art. The receiver unit 5 may be, in some embodiments, an off-the-shelf Bluetooth USB adapter dongle.

The tablet computer 6 is used to collect data transmitted from the control module 3, allow user inputs to store and track motor performance and therapy device parameter settings, and provide clinicians with real-time symptom quantification feedback. The tablet computer 6 of the illustrated embodiment may be any computing device with a user interface 7, including a smart phone, PDA, laptop computer, desktop computer, iPhone, iPad, or the like. Preferably, the tablet computer 6 is lightweight and portable, allowing for its easy transport within an operating room or other setting where the clinician, physician or technician would utilize the device, and includes a touch screen. In some embodiments, the tablet computer 6 may be equipped with a clip or hanger (not shown) for easy mounting to, for example, an operating room pole. Most preferably, the tablet computer 6 is any mobile device that the clinician, physician or technician can utilize remotely from the subject by receiving any data communicated from the subject's movement disorder diagnostic device, a database, or other sensors or systems used to measure, monitor, or record the subject's movements. The tablet computer 6 allows the clinician, physician or technician to access the data and analyze it wherever he or she may be, and without requiring the subject to be located in the immediate location or vicinity.

The user interface 7 may be visual, preferably comprising a touch screen, or it may be an audio interface that accepts and transmits spoken commands. In addition, or alternatively, the user interface may be used to provide an automated testing protocol to the subject 1 by providing instructions to the subject 1 on which movement disorder test(s) to perform, and how to perform them. In preferred embodiments, the subject 1 may be instructed on which tests to perform and/or how to perform them on a separate display, not on the tablet's user interface. In such embodiments, the subject 1 and clinician, physician or technician preferably have separate devices with user interfaces such that the subject can receive instructions on movement disorder tests to perform while at home or otherwise remote from the healthcare professionals, and the clinician, physician or technician can access the subject's movement data while remote from the subject. The user interface 7 preferably provides several key components and an overall software wrapper. First, it preferably provides a main menu (not shown) to access all software features including a subject database (not shown), the tuning assistant software, which runs the therapy device parameter settings tuning algorithm, and software for automatically generating clinical reports following tuning sessions. Next, it preferably provides a module to view real-time motion data transmitted by the movement disorder diagnostic device comprising sensor unit 2 and command module 3, helping ensure proper setup and communication prior to clinical therapy device programming. The user interface 7 also preferably communicates with the system registry to store system parameters and clinician preferred settings. Finally, a help menu (not shown) with troubleshooting guides and frequently asked questions is preferably included.

Subject data management is an important aspect of clinically-used embodiments of the present invention. Preferably, the format of the software used with the system is designed for a high volume subject database. Any database known in the art may be used but is preferably one which scales well to accommodate thousands or tens of thousands of subjects. Preferably, the database has fields for subject history, including the subject's surgery dates, a running list of the subject's clinical sessions (past and/or future scheduled), the subject's primary physician, neurologist, medication dosage, etc. Preferably, the subject is also programmed with the ability to import e-mails and other documents into the subject history, and to export a standardized patient information sheet (reporting). Preferably, the database is programmed so as to permit all stored subject information to conform HIPAA guidelines for patient privacy and confidentiality.

A separate programmer device 8 is used in some embodiments by the clinician, physician or technician to remotely program the subject's therapy device, that is, to adjust the therapy device's parameter settings. The separate programmer device 8 may be a separate device from the tablet 6, but more preferably the tablet is capable of providing both functions (see FIG. 2). Whether the separate programmer device 8 is separate or integrated, it communicates with the subject's therapy device (e.g., DBS device), and transmits the desired therapy parameters to the subject's therapy device such that the therapy device operates under the transmitted parameters. Where the programmer device or unit is separate from the tablet, preferably communication between them is by wireless methods as described above. In all embodiments, the programmer device or unit preferably communicates wirelessly with the subject's therapy device.

In addition, or alternatively, the movement disorder diagnostic device comprising the sensor unit 2 and command module 3 may transmit to a server or group of servers constituting a centralized database, such as with cloud computing whereby the data resides on such server or group of servers and can be accessed at the point of testing or some remote location for review by a clinician, physician or technician. Further, the tablet and/or programmer device or unit may also communicate with and transmit data to a centralized database or cloud-based database in order to store the preferred therapy parameters for the particular subject, as well as information regarding the testing and tuning protocols used to arrive at the desired parameters. All the data that is transmitted and stored on a centralized database or cloud-based database is intended to be made accessible to the clinician, physician or technician for later review, for reference when the subject requires additional treatment or tuning, and to be readily available to other clinicians, technicians or physicians who the subject may receive treatment of any variety from and who might need to access the data in order to properly and safely attend to the subject. For example, a subject may reside in one state through the summer months and receive tuning of the therapy device and treatment there, but then may travel to another state for winter months and require similar attention there. The database storage of data allows clinicians, technicians or physicians in both states to readily obtain access to the subject's data and to provide the appropriate care to the subject. In all exchange of information that occurs in the above example and in all other embodiments of the present invention, it is important that information be exchanged securely and in ways that do not improperly disclose a subject's identity. Because of this, in certain preferred embodiments, all personal information of a subject is stored securely at a remote database and is accessible only through a secure network connection wherein both the database and connection protocol are compliant with standards required by the health insurance portability and accountability act (HIPAA). Often, this will require encryption of the data to eliminate the possibility that the data can be read by a third party and many preferred embodiments of the present invention include the use of data encryption.

Figure 3:
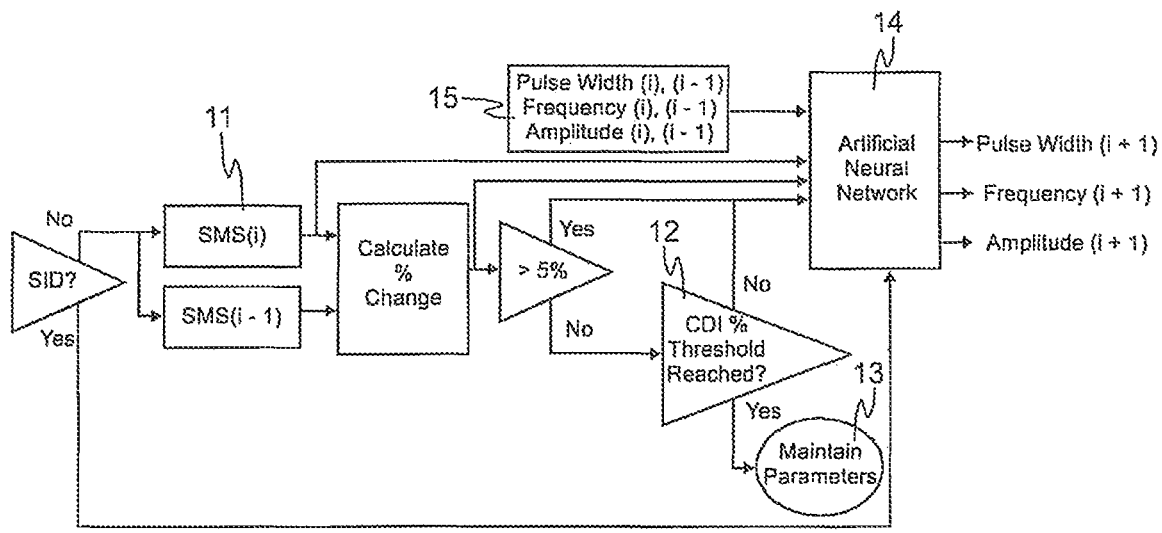
FIG. 3. Flow diagram of a parameter adjustment suggestion algorithm in some embodiments of the present invention.

As indicated in the above example, various embodiments of the present invention involve sending a movement disorder monitoring device home or to another remote location with a subject to be used for movement disorder testing away from a physician's or clinician's place of practice. This step likely occurs after initial programming of the display unit as described above. Once the subject arrives home, the movement disorder monitoring device is placed in the subject's home where it may be powered by either a single or multiple on-board batteries or by another power source in the subject's home such as a standard 120 volt alternating current outlet. Once in the home the display unit may, at intermittent times selected by the programming physician or clinician, alert the subject of the need to perform certain movement disorder evaluation tasks. Alternatively the movement disorder diagnostic device may be worn continuously allowing measurements and recordings to be taken periodically, at scheduled intervals or times, or based on stimulus or measurements that indicate the subject is performing a particular activity, movement or motion, or is experiencing some symptom or side effect of therapy. At these times, the display unit may produce a sound, provide a visual alert on its display screen, or a combination of both as a way to alert the subject. In response to the alert the subject will place at least one sensor on his or her extremity (ies) as instructed by the display unit, if the diagnostic device containing sensors is not already being worn, and will proceed to follow other instructions provided regarding how to properly complete certain tasks used to evaluate the severity of the subject's movement disorder symptoms. Again, alternatively, in some embodiments or circumstances, no particular task may be required, but the device may take measurements and recordings while the subject is performing activities of daily living. In certain embodiments, the subject may be video recorded by the camera of the display unit so that a physician can at a later time verify that the tasks were indeed correctly completed. Preferably, the subject will also answer other questions at this time regarding a subject's self-assessment of his or her symptoms and the subject's adherence to and use of treatments prescribed by the subject's physician or another clinician. Such questions may consist of inquiries related to the subject's perception of the present severity of the subject's symptoms, the subject's most recent dose of pharmaceutically-based treatment, the subject's activity level throughout the day, and other similar pertinent information that is desired to be known by the physician to help better understand a subject's symptoms. As noted above, however, in certain other embodiments, the display unit may not be programmed to alert a subject, but instead may simply be left available for a subject to input data regarding his or her symptoms or to select movement disorder assessment tasks to perform from among various options according to the subject's personal preferences and schedule as well as the subject's own subjective view of the severity of his or her symptoms. The data from the instructed tasks or activities of daily living is then transmitted or communicated to a remote location (e.g., directly to the clinician, physician or technician, or to a database or server) where the clinician, physician or technician can access and analyze the data in order to more accurately provide a next or second level of therapy parameters or setting that more directly addresses the subject's needs In the embodiment illustrated in FIG. 1, the subject 1 performs a movement disorder test according to instructions. Given the preferred embodiments involve remote monitoring, measuring and quantification of the subject's motor symptoms, the subject is preferably at a remote location, such as at home, when performing the movement disorder test(s) (or while performing the activities of daily living in some embodiments). In such embodiments with remote monitoring and measurement, instructions may be provided by an instructional video clip displayed on a user interface 7 of a tablet computer 6 (which is separate from the tablet computer that is in the possession of the clinician, physician or technician), or on a separate display device (such as a home personal computer, smartphone, or other such device, not shown) advantageously providing the subject with a standardized visual aid to mirror while a test is conducted and data is collected. Alternatively, or in conjunction, the clinician, physician or technician may communicate with the subject via teleconference, or more preferably, video conference and thus provide instructions to the subject live. Video conferencing is preferred over teleconferencing to allow the clinician, physician or technician the ability to monitor and observe the subject as her or she performs the test(s) in order to ensure they are performed correctly. Such a system implemented in software and provided through user interface 7 ensures the same clinical examination protocol is used during subsequent test or programming sessions either in-clinic or in a non-clinical setting, advantageously allowing clinicians to more repeatedly and objectively track symptoms and assuring inter-subject data correspondence. In one embodiment, testing includes (or may be limited to) three types of tremor tasks (resting, postural, and kinetic) and three types of bradykinesia tasks (finger tapping, hand grasps, and pronation/supination). Either alternatively or in addition, testing may include various gait/balance tasks, lower extremity bradykinesia tasks, or other similar tasks as well. The movement disorder diagnostic device, or more specifically the sensor unit 2 of the diagnostic device, collects data, which is sent to command module 3 for transmission via radio link to a receiver unit 5. The processor of the tablet computer 6 processes the movement data to extract kinematic features, which are then fed into a trained scoring algorithm implemented as a software algorithm in the tablet computer 6. The trained scoring algorithm may output a score, which may then optionally be displayed on the user interface 7. In some embodiments, the clinician, technician or physician then determines the next or optimal settings or parameters for the subject's therapy. In other embodiments, an algorithm of tablet computer 6 then computes suggested therapy device parameter settings based at least in part upon the current therapy device parameter settings and the collected movement data and/or the quantified score computed therefrom. An exemplary tuning algorithm for computing the suggested therapy device parameter settings is illustrated in FIG. 3. The clinician may input the existing therapy device parameter settings into the user interface 7, or the tablet computer 6 may communicate directly with the programmer device or unit 8, wired or wirelessly, to ascertain preexisting parameter settings.

Once suggested parameter settings adjustments are determined by the clinician, technician or physician, or computed by the tuning algorithm, the adjustments or new settings are displayed on the user interface 7. They may then be manually entered into the programmer device or unit 7 for reprogramming of the therapy device, or the tablet computer 6 may communicate directly with the programmer device or unit 8, wired or wirelessly, to adjust the parameter settings. The therapy device may be reprogrammed wired or wirelessly, and typical implanted therapy devices are enabled with means of wireless transcutaneous reprogramming.

Figure 2:
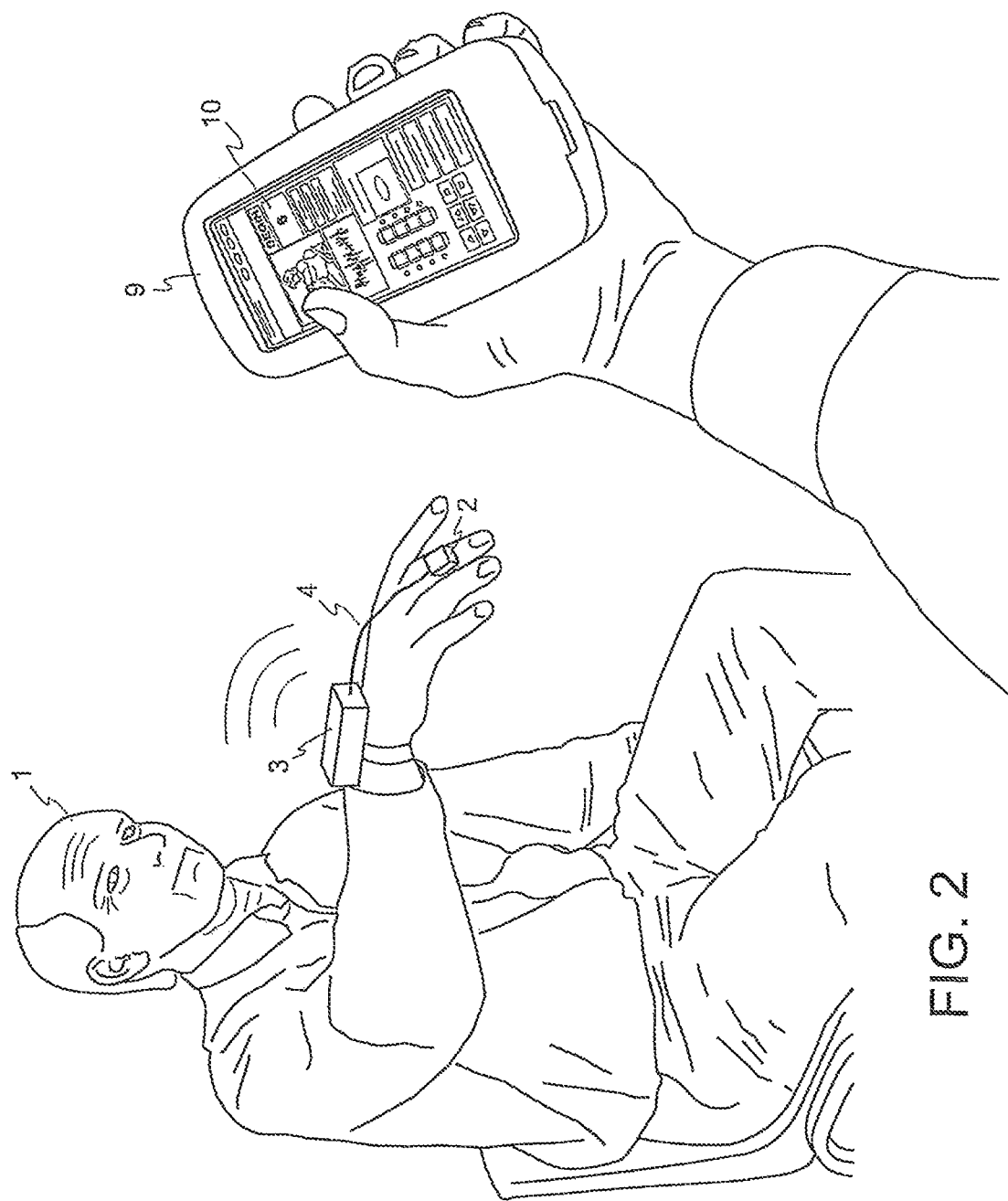
FIG. 2. Schematic view of a subject undergoing post-surgical DBS adjustment with another embodiment of the invention involving electronic transmission between the system and the subject's DBS device.

The alternate embodiment of the invention depicted in FIG. 2 advantageously combines the receiver unit 5, the tablet computer 6, the user interface 7, and the separate programming device 8 into a programmer unit 9 having improved user interface 10, which is preferably a touch-screen interface. Preferably, the subject 1, and the clinician are located remotely from each other. The command module 3 of the movement disorder diagnostic device transmits movement data acquired by the sensor unit 2 of the movement disorder diagnostic device, as described above, to the programmer unit 9, where the movement data is analyzed and parameter settings adjustments are computed. Alternatively, or in conjunction with transmitting the data directly to the programmer unit, the data may be transmitted alternatively or simultaneously to a remote location, which may be a database or server (not shown), from where the clinician, physician or technician may then access the data immediately or at a later time for review and/or analysis. The parameter settings may then automatically updated, with the programmer unit 9 remotely interfacing with the therapy device (not shown) directly to communicate the updated parameters or settings to the therapy device reprogram the therapy device's parameter settings.

Preferably, the touch screens of tablet computer 6 and programmer unit 9 permit a user to interact with the user interface 7 or the improved user interface 10 using a large sterile stylus (not shown), or the user's finger.

In alternate embodiments of the invention, quantification of movement disorder symptoms may be performed using a different form of movement measuring apparatus. In one such example, a webcam built into the tablet computer 6 or programmer unit 9, or a video camera or set of multiple cameras connected thereto, view the subject 1 performing the motion disorder test and feed video data into the tablet computer 6 or programmer unit 9 where, for example, machine vision algorithms measure the motion of the limbs of the subject with respect to time according to any method known in the art. Such a method may consist, for example, in determining marker points along the limb of the subject in order to gauge relative motion, and such a method may be assisted by applying more visible markers (not shown) on various points on the limb of a subject 1, such as is common with motion capture technology. In such case, the need for the movement disorder diagnostic device comprising sensor unit 2, with its accelerometers and gyroscopes, and command module 3, may be obviated.

In one embodiment, an initial programming session will be carried out when the device is first provided to the subject according to a protocol comprising the following steps. The clinician will assess all motor task baseline scores. The clinician can remotely check electrode impedance for wire damage. This can be done be receiving periodic signals corresponding to electrode impedance, though more preferably (either alternatively or inconjunction with periodic signals) allows the clinician to interrogate the device remotely and obtain necessary measurements and signals to determine or relate the electrode impedance to the clinician at his or her remote location. The clinician will record medication dosages, which information preferably includes information relevant to the subject's present level of medication, such as time and dosage of last medication administration. The clinician will select programming motor tasks, and in conjunction with the programmer device or unit 8, 9, the subject will repeat the series of motor tasks for each stimulation setting. The DBS settings or parameters and corresponding scores for each chosen motor task will then be entered remotely either manually by the clinician, physician or technician communicating the updated parameters or settings to the subject's therapy device, or more preferably integratedly where the clinician has the ability to switch between tasks for entering data and selecting which DBS parameters are fixed: frequency, current, pulse width, waveform type, contact setup (mono, bi, tripolar), and the like, and the system communicates those parameters or settings to the therapy device remotely without direct clinician interaction after selection. Finally, the tuning algorithm(s) will assess all motor tasks post-programming, and the clinician will have the option of reviewing, and possibly editing the resultant parameters or settings. Preferably, for the clinician's optional review and editing, the system will provide the ability to enter DBS settings or parameters and scores completely either with a finger or stylus on a touch screen, and/or with a mouse and/or with a keypad or keyboard using the tab key to switch between data input fields. Preferably, the system provides three data input modes for clinician review and editing: (1) enter stimulation and score information, click update, enter next measurement; (2) enter information and display updated tuning map; (3) use stylus/ finger/mouse to click on the tuning map for the appropriate measurement, with a new input box appearing to enter score/side effects/notes. Optionally, the initial programming session may be performed without direct interaction with the tuning map, but rather where the algorithm(s) populate the tuning map, and the clinician, physician, or technician engages the optional review function to view the tuning map and/or the parameters or settings chosen by the algorithm(s) in order to approve or deny them based on the subject's needs and the results from those therapy settings.

It is advantageous in some embodiments for the system to provide, or to permit the clinician performing the programming session to enter a large number of variables in order to provide a complete assessment of the DBS tuning. The following is a representative list of information that may be entered in each programming session: (1) general subject information, including patient ID, whether the subject's DBS implant is unilateral or bilateral, implant electrode site location and side; (2) motor evaluations performed during tuning, including (a) tremor: rest, postural, kinetic, (b) bradykinesia: finger tap, hand grasp, pronate/supinate, (c) rigidity: elbow/knee, head/neck, (d) leg agility: heel tapping, (e) rising from chair: with arms crossed, (f) posture, (g) gait: walking quality, (h) postural stability: pull back; (3) motor scores, in the form of integer scoring from 0 (no severity) to 4 (extremely debilitating); (4) DBS settings or parameters, including, but not limited to (a) contact: cathode/anode, monopolar, bipolar, tripolar, multiple channels with fractionalized control, waveforms, current steering, different waveforms, interleaving multiple waveforms, etc., (b) stimulation parameters including amplitude (in volts), frequency (in Hz), current (in amps), pulse width (in microseconds), the type of waveform of the stimulation impulse, (c) side effects and/or capsule effects, including (i) motor effects, such as worsening of symptoms, dyskinesias, facial pulling, (ii) non-motor effects, such as blurry vision, soft or slurred speech, sweating, headache, tingling (transient/non-transient), fatigue, sense of euphoria, paresthesia, and/or (iii) new or atypical side effects and update list of notable effects.

FIG. 3 shows merely one optional example of a tuning algorithm used for computing suggested parameter settings adjustments in embodiments where such capability is present. This basic tuning algorithm utilizes symptom severity data, detected stimulation induced dyskinesias (SID), and clinical inputs such as clinician defined improvement percentage (CDI %) to compute suggested stimulation parameter settings. Based on the typical clinical description, several constraints reduce the number of degrees of freedom in the tuning algorithm. During DBS programming, the clinician or the algorithm may utilize any subset of the motor task mentioned previously to evaluate motor performance. The average tremor score (ATS) is computed for the set of tremor tasks and the average bradykinesia score (ABS) is computed for the set of bradykinesia tasks utilized for a given iteration. This reduces the number of symptom severity outputs from a maximum of three to one for each symptom. Dyskinesia is either "on" or "off."

Recording symptom severity before the therapeutic device is turned on obtains baseline. In the case of DBS adjustment, the best monopolar electrode contact is determined by finding the contact that provides the largest therapeutic width, i.e., the largest change in supplied voltage from when a clinical benefit is noticed to when side effects occur. This is accomplished by fixing stimulation pulse width to initial settings, for example 60 µs, frequency to 130 Hz, selecting one contact, and then stepping the voltage amplitude in small increments of approximately 0.2 V. The procedure is repeated for each contact. The contact that provides the largest therapeutic width is selected. With the pulse width (60 µs) and frequency (130 Hz) set to typical values, the clinician or the algorithm then sets the amplitude to the lowest voltage that provides a significant decrease in symptoms. If a satisfactory result is not achieved, pulse width or frequency may also be increased. This can be a time consuming iterative process that must be completed several times over the first few months as microlesioning heals and requires a compensatory increase in stimulation amplitude to maintain clinical benefit. In various embodiments, the invention includes a sensitive tool, implemented in software and accessed through user interface 7 or improved user interface 10 to detect the instant of clinical benefit as voltage amplitude is increased and the instant any stimulation induced dyskinesias are detected. Use of the invention as a sensitive measure of clinical benefit onset and side effect occurrence advantageously ensures the contact with the greatest therapeutic width is selected.

Once the contact width is selected, the initial parameter settings adjustment iteration may be completed with literature-defined settings of 60 µs and 130 Hz stimulation. Amplitude is set to 0.2 V initially, and then modified by the clinician or algorithm in subsequent iterations. After each stimulation parameter change, the clinician may use the user interface 7 or the improved user interface 10 to guide the subject through motor tasks, or, in some preferred embodiments, the device will automatedly provide instructions to the subject via a display to provide such guidance. The tuning algorithm output provides a suggested parameter direction output after each motor task evaluation by utilizing the movement disorder quantification algorithm. The invention thereby maximizes clinical benefit by minimizing tremor and bradykinesia, minimizes adverse effects of stimulation-induced dyskinesias, and minimizes current consumption to maximize battery life. Thus, one objective function is to minimize the sum of average tremor score (ATS) and average bradykinesia score (ABS), known as the summed motor score (SMS) 11. This objective is achieved in the tuning algorithm by continuing to increase stimulation in the same direction as long as SMS is decreasing. A higher SMS corresponds to worse motor symptoms. A second constraint is that stimulation induced dyskinesias (SID) should not occur. If they are detected, the direction of the parameter change is reversed. Another system constraint is the minimization current consumption. This is accomplished by allowing a clinician defined improvement percentage (CDI %) 12 and considering any changes of less than 5% in SMS to be insignificant. When these conditions are met, the current parameter level is maintained 13 due to the SMS goal being achieved and with consideration given to diminishing clinical returns, in order to maximize battery life. Once optimized amplitude has been achieved or reaches 3.6 V, the clinician may adjust pulse width or frequency utilizing the same algorithm. The chances of the feedback system settling into local minimums are reduced by ensuring several of the settings are set at clinically accepted levels for the initial iteration and making only moderate adjustments as required.

While DBS programming frequently entails stepping through small incremental changes, this process can be wastefully time-consuming if the motor symptom response of the subject indicates larger changes are required. The implementation of an artificial neural network 14 to output suggested stimulation parameters minimizes programming iterations to reduce surgical and outpatient tuning session time.

Preferably, the artificial neural network 14 used in the tuning algorithm used by some embodiments of the present invention is trained with recorded clinician-made stimulator parameter changes in response to motor symptom severity changes during stimulator programming to minimize required iterations while still utilizing objective symptom severity measures to optimize performance. In this way, the algorithm takes clinician experience into account. Experienced clinicians are generally successful in quickly reducing the number of potentially successful parameter settings for tuning DBS systems. An expert clinician is capable of recognizing severe motor symptoms and modifying a parameter by a larger magnitude, then when the symptom is less and only fine-tuning is required. The present invention is therefore capable of quantitatively detecting motor symptom severity and suggesting a parameter change that approximates or mirrors the parameter change that would be made by an expert clinician.

Artificial neural network 14 may be implemented, for example, with the MATLAB Neural Network Toolbox offline using resilient backpropagation batch training. Inputs to the neural network may include current and previous stimulation settings 15 and motor responses.

Figure 4:
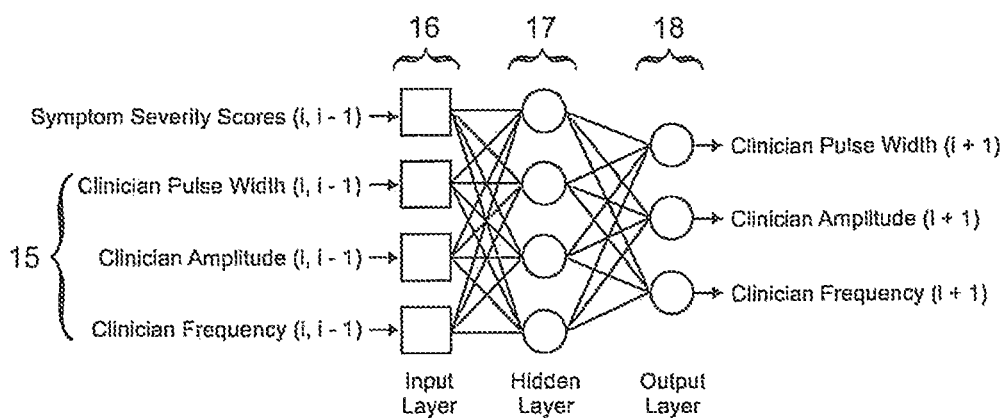
FIG. 4. Flow diagram of an artificial neural network of the parameter adjustment suggestion algorithm in some embodiments of the present invention.

FIG. 4 illustrates a two-layer network structure consisting of one hidden layer 17 with four neurons using "tansig" transfer functions and one output layer 18. As neural networks may fall into local minimums when being trained, each network is preferably trained three times with randomized initial weights and biases and the best training results are selected. Additionally, early stopping improves network generalization. Data is separated into training and generalization sets to ensure trained networks produce accurate results both when the training set is reapplied and also when it is generalized to new data. Preferably, training data is collected from multiple patients. To ensure that the system generalizes to new patients, network generalization can be tested by training the system using a jackknife "one left out" method. Using such a method, the neural network is trained using data from, for example, only nine of ten subjects. Data from the nine subjects in the training set is then reapplied to the trained network to ensure good correlations while data from the "left out" subject is used to test generalization. The method is repeated, leaving out each subject one time. For each training and generalization set, both the mean squared error (MSE) and R-squared values between the clinician-made stimulator parameter changes and those output by the system for each stimulation parameter are calculated. The MSE and R-squared for all training and generalization sets are averaged. Preferably, the system achieves normalized MSE values of less than 10% and R-squared values of greater than 0.8 to show substantial agreement between system-suggested simulation parameter changes and clinician-made stimulation parameter changes.

Preferably, separate data sets and acquired, and separate neural networks are trained, for the surgical and outpatient scenarios. Preferably, the data used to train the algorithm averages the experience of multiple expert clinician programmers.

Preferably, the tuning algorithm comprises a neural network as illustrated in FIG. 3, but it might instead or in addition comprise one or more of adaptive continuous learning algorithms, linear quadratic Gaussian control, Kalman filtering, and model predictive control.

When the tablet computer 6 is connected to the Internet or similar communications network, wired or wirelessly, it may therefore transmit subject data to remote systems, allowing general practitioners to conduct DBS programming remotely, minimizing travel for a subject 1 who lives far from a DBS implantation center or suitable programming clinic, so long as the subject 1 is equipped with the movement disorder diagnostic device comprising sensor unit 2 and command module 3 and means of programming and/or making parameter settings adjustments to his or her therapy device (including DBS implant).

Figure 5:
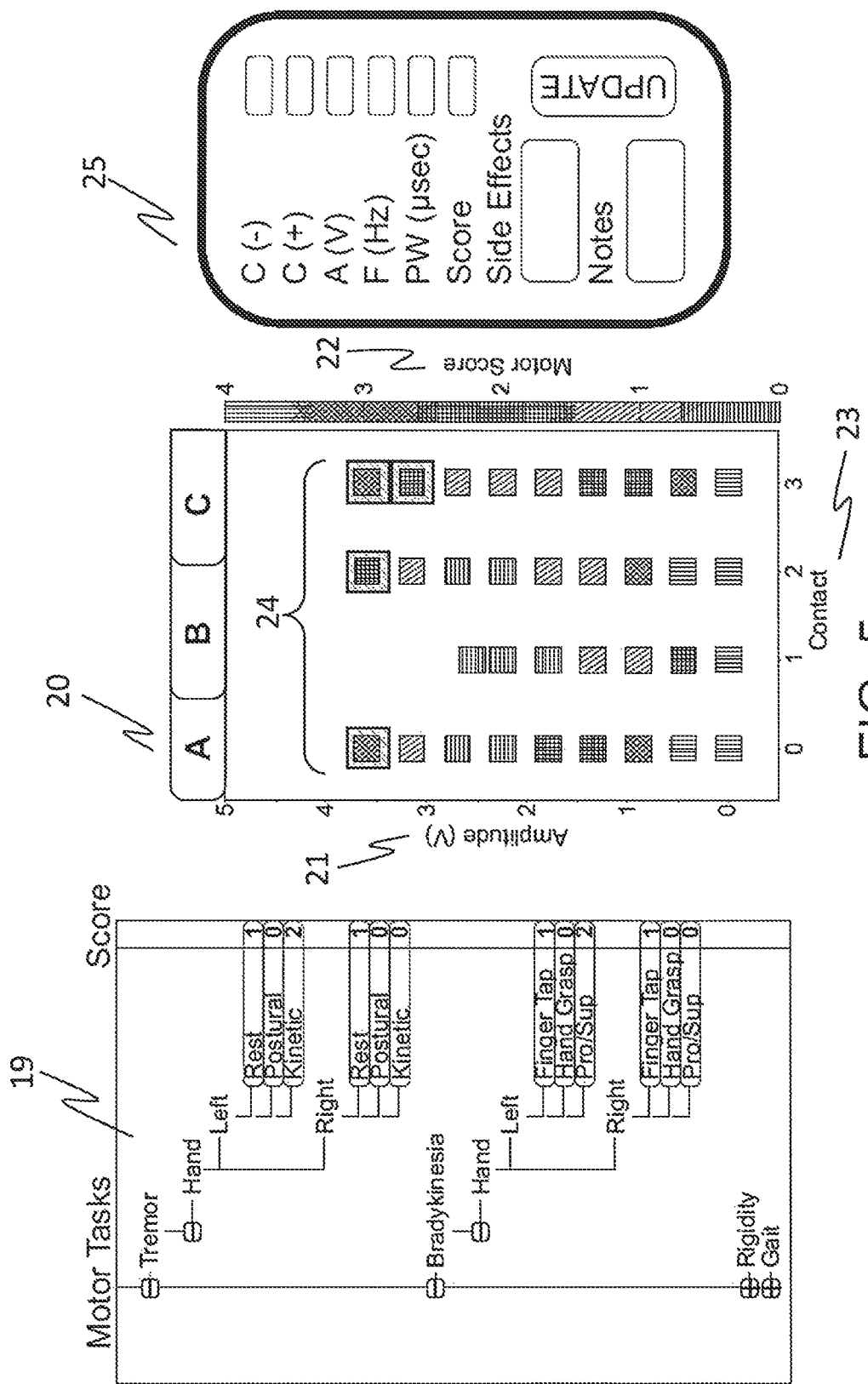
FIG. 5. Graphic depiction of display pages displaying test results and scores, one embodiment of a tuning map, as well as one embodiment of a parameter input screen.

FIG. 5 depicts a series specific display pages corresponding to reporting score provided for optional or periodic review by a clinician, physician or technician in various embodiments of the present invention. These examples of methods of reporting scores with visual displays associated with each display stage of the test process are merely exemplary, and many variations of the display method, as well as the labeling of the display, are envisioned. One example of displaying a score for optional or periodic review is the expandable menu view 19, where the user (i.e., clinician, physician, or subject performing self-testing away from the clinician) is presented with a list of the different types of movement disorders or movement disorder symptoms, which may or may not have been measured in a given test. In the portrayed example of this expandable menu view 19, the movement disorder symptoms that may be selected include tremor, bradykinesia, rigidity, gait and/or balance disturbances, and the like. The user is then given the option of expanding the results for each of those movement disorders or movement disorder symptoms through a series of levels (i.e., hand then to left or right), in order to view the score that was determined for each particular disorder or symptom in the indicated portion of the subject's body. By way of clarification and example, the subject shown in menu view 19 received a score of 1 during rest for the symptom of tremor in the left hand, and a 2 for the pronation/supination task for bradykinesia in the left hand.

Another optional review display method, which may be independent or used in conjunction with the expandable menu view is the tuning map 20. A tuning map 20 is generated for each task that the subject is directed to perform, symptom, or side effect and depicts the severity of the symptoms measured in each sensor that is used for the given task. Each task, symptom or side effect that is performed may be represented on a different tab (i.e., tab A, tab B, tab C, where the lettered tabs in FIG. 5 either correspond to a task, symptom or side effect). Alternatively, the tab letters may be replaced by other labels or indicators, or even the name, or abbreviation thereof, of the task, symptom or side effect. Further alternatively or in addition, the different tabs may represent combinations of tasks, symptoms (e.g., averaged results of multiple symptoms), and/or combinations of side effects. In this particular embodiment, the amplitude 21 at which the test was performed is measured in volts and indicated on one vertical axis of the tuning map 20. Also in this particular embodiment, the contact being used to provide therapy or stimulation is indicated on the horizontal axis 23. However, in many embodiments, the axes may represent any other test parameter or setting used, and in some preferred embodiments, one of the axes (typically the horizontal) may represent different groupings (see FIG. 6) of test therapy settings or parameters. In such embodiments, for example, the axis would provide a representation of a group (e.g., 1 representing group 1), which would comprise a predetermined set of therapy parameters or settings being tested, where the grouping may include variations of any of the above described therapy parameters or settings, such as contact, current, frequency, waveform, polarity, pulse width, and the like, as well as combinations thereof. Some embodiments further allow the condition to use varying or comparative settings within the groupings. For example, it may be decided to combine the settings in such a manner to provide weighted scores where one symptom, task, or side effect is given a greater weight than another, but they are combined to create a single weighted map. Similarly, therapy settings or parameters may be gradually increased or decreased as symptoms are continuously measured, rather than providing measurements or assessments at discrete amplitude levels. This allows a greater degree of freedom and versatility in defining the test settings instead of being limited to one or two test parameters per test. Such groupings decrease the amount of testing time required for tuning, and thus reduce cost to the subject or insurance company, as well as opportunity cost of the clinician's time spent with a single subject. The calculated or estimated score 22 is depicted on a vertical axis of the tuning map 20 as well, and is indicated as various cross-hatch patterns. Alternatively, the score may be represented by colors, shapes, or any other indicator. Each individual box that is shown represents a test performed 24. Preferably, the tuning map 20 is shown on a color display (not shown) for optional review and the severity of the symptom is indicated by color. In this drawing, the colors are represented by different types of shading or cross-hatching rather than by the preferred color. Each column in the tuning map 20 represents a different contact on the DBS probe. Therefore, each individual test box 24 depicts the results of performing a task while administering DBS at a prescribed voltage amplitude 21 and provides both a severity of the symptom that was detected or measured by virtue of the color (represented by the cross-hatching), which also correlates to a given motor score. Additionally, each individual test box 24 may be selected, for example by pressing it on a touchscreen device, as representing by the test boxes 24 which are outlined in black. When a test box 24 is selected, the user is able to see a detailed view (not shown) of the statistics and parameters of the test corresponding to that box. In many embodiments, the clinician, physician or technician may be able to add notations to the different parameter or setting groupings, or even to the individual test scores. Such notations may include commentary or other notes regarding the efficacy of the given parameter grouping or score, of side effects that occur, or any other notations the clinician, physician or technician deem necessary.

A variable window 25 may display on the unit as well that allows the user to input various conditions that have an effect on the test and test results. These variables are calculated into the test results and help to give a more accurate calculated symptom score.

Other methods of displaying data corresponding to test therapy settings or parameters and results may also be envisioned and are considered for use with the present invention.

Figure 6:
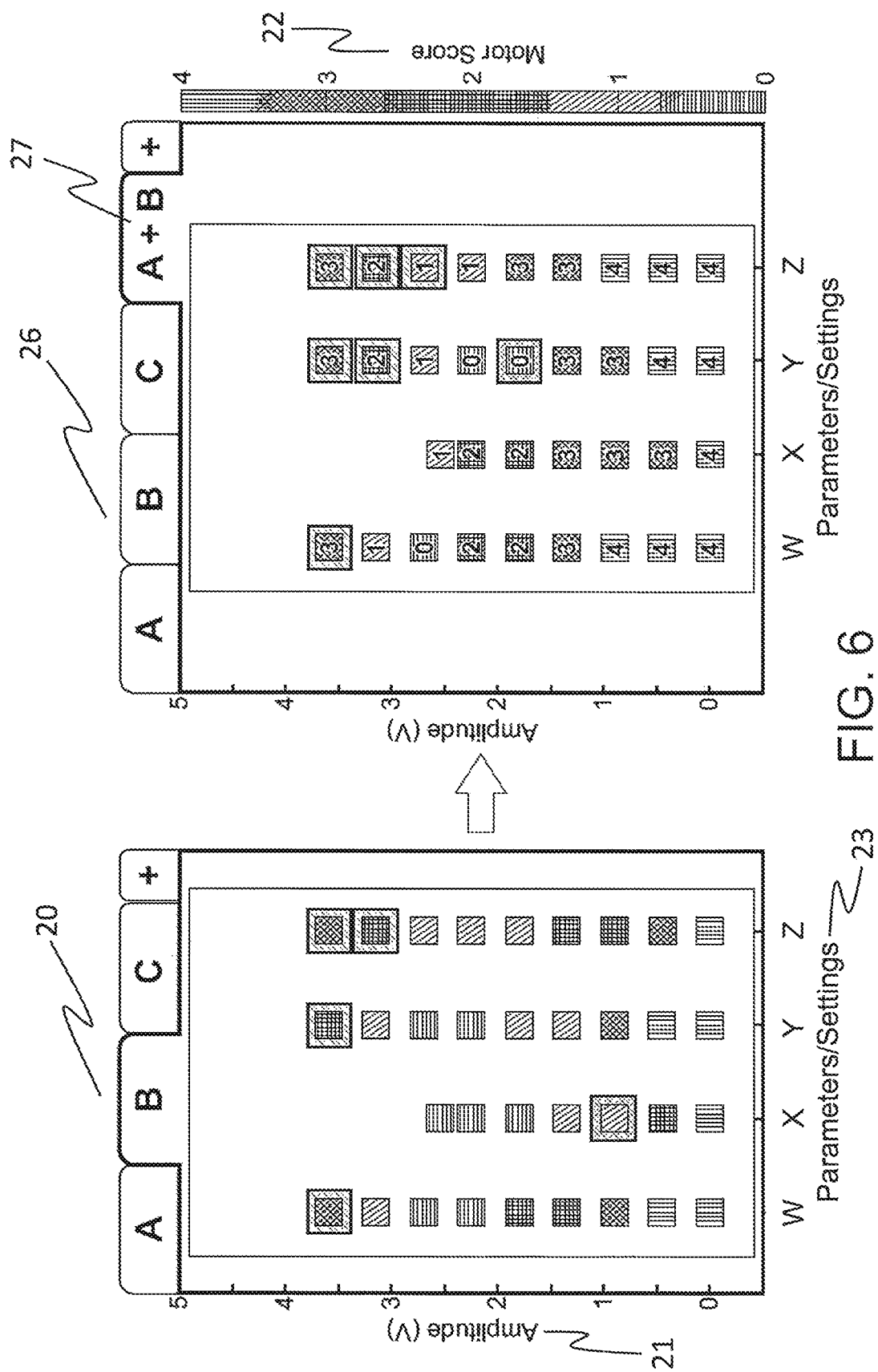
FIG. 6. Graphic depiction of one embodiment of tuning maps used to display test results and symptom severity objectively measured by the system and displayed as a scatter plot of symptom severity scores.

FIG. 6 portrays one example of the optional or periodic review tuning maps 20 or other visual display tool or method for a particular embodiment with amplitude 21 on the vertical axis and groupings of parameters or settings 23 on the horizontal axis, in greater detail. Each task performed, symptom or side effect is represented again by a separate tab with its own tuning map 20. Though the tabs are labeled as A, B, C and A+B in the figure, in many preferred embodiments the tab may be labeled with a number, the name of the task, symptom or side effect it represents, an abbreviation thereof, or some other label indicating to the clinician, physician or technician what information is represented in the given tab. The amplitude 21 of the voltage at which the test was performed is tracked along one vertical axis of the map 20 for each grouping of parameters or settings 23 on the DBS lead (for this particular depicted embodiment), while the severity of the symptom detected or measured is displayed as a score 22 and correlated to an indicator (e.g., cross-hatching pattern, color, or the like) of each individual test result box 24. Again, in many preferred embodiments, rather than the labeling the groupings of parameters or settings 23 used to provide stimulation with letters (e.g., W, X, Y, Z in the figure), they may instead be labeled by a grouping number, grouping name, or any other labeling scheme or plan, which indicates to the clinician, physician, or technician which grouping of settings or parameters is represented. Preferably, the groupings are cross-referenced within the software and/or GUI such that a user, clinician, physician or technician may readily and easily be able to see what parameters or settings correspond to the chosen grouping label. The right side 26 of FIG. 6 portrays a new tab 27, which represents the combination of tabs A and B. This combination tab 27 represents the combination of the tuning maps for tasks A and B, and the combination can be of any mathematical variety such as averaging, weighted averaging, or the like.

The combination 27 is a result of the user selecting those two tuning maps to be combined together and optimized in some mathematical way (e.g., averaging) in order to show the results of how the scores for each task combine in order to optimize the DBS level for treating the subject. In other words, the goal is to minimize the voltage at which the DBS is to be supplied while simultaneously minimizing the severity of the subject's symptoms and/or side effects. Combining the tuning maps for each task allows the user to see a resulting score and select the DBS test parameters, which are as close to optimal as possible. In a preferred embodiment, the system would be designed to be a closed-loop system, (i.e., for an implanted home-diagnostic and therapeutic device), which would not require extensive, or any, user input, but would perform the optimization automatically.

Figure 7:
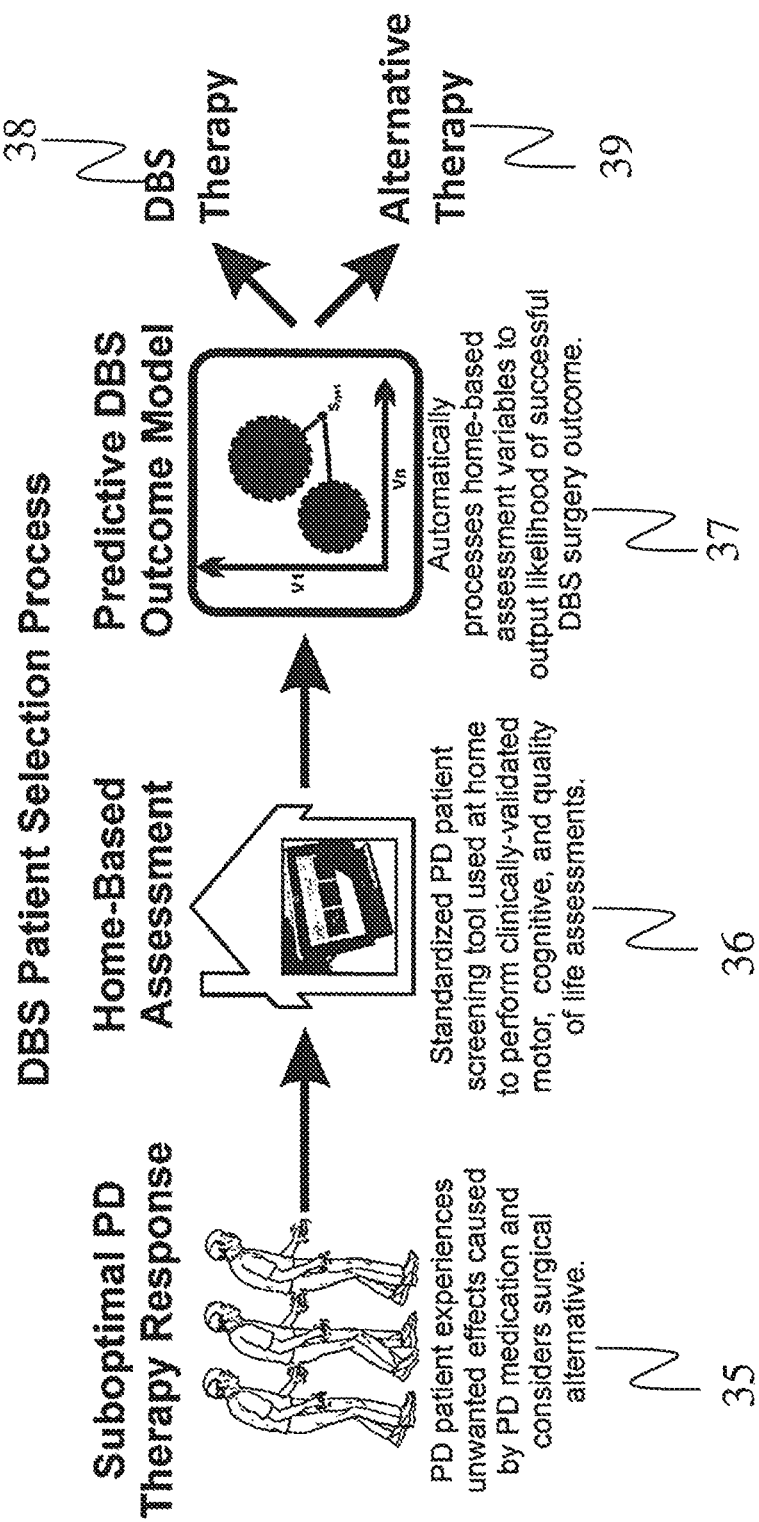
FIG. 7. Illustration of the subject screening process to determine if DBS is a viable option for a particular subject.

FIG. 7 depicts the screening process for determining whether a subject is a good and viable candidate for DBS therapy. When a subject begins to experience side effects 35 from medication he or she is taking to treat the symptoms of a movement disorder, the subject or his or her clinician may begin to consider new treatment methods other than simply relying on medication. The clinician may then have the patient undergo a home screening assessment 36 to perform monitoring and recording of the subject's symptoms and test results (motor and cognitive tests) with a system for monitoring and recording those results. Next, preferably the system utilizes predictive tuning algorithms 37 to analyze the many variables and test results in order to make a determination as to whether the subject would benefit from DBS therapy 38. If the determination is that the subject would benefit, then the clinician and subject may decide to undergo DBS surgery and therapy 38. However, if DBS is not a viable option for the subject, then alternative therapies 39 should be considered.

Figure 8:
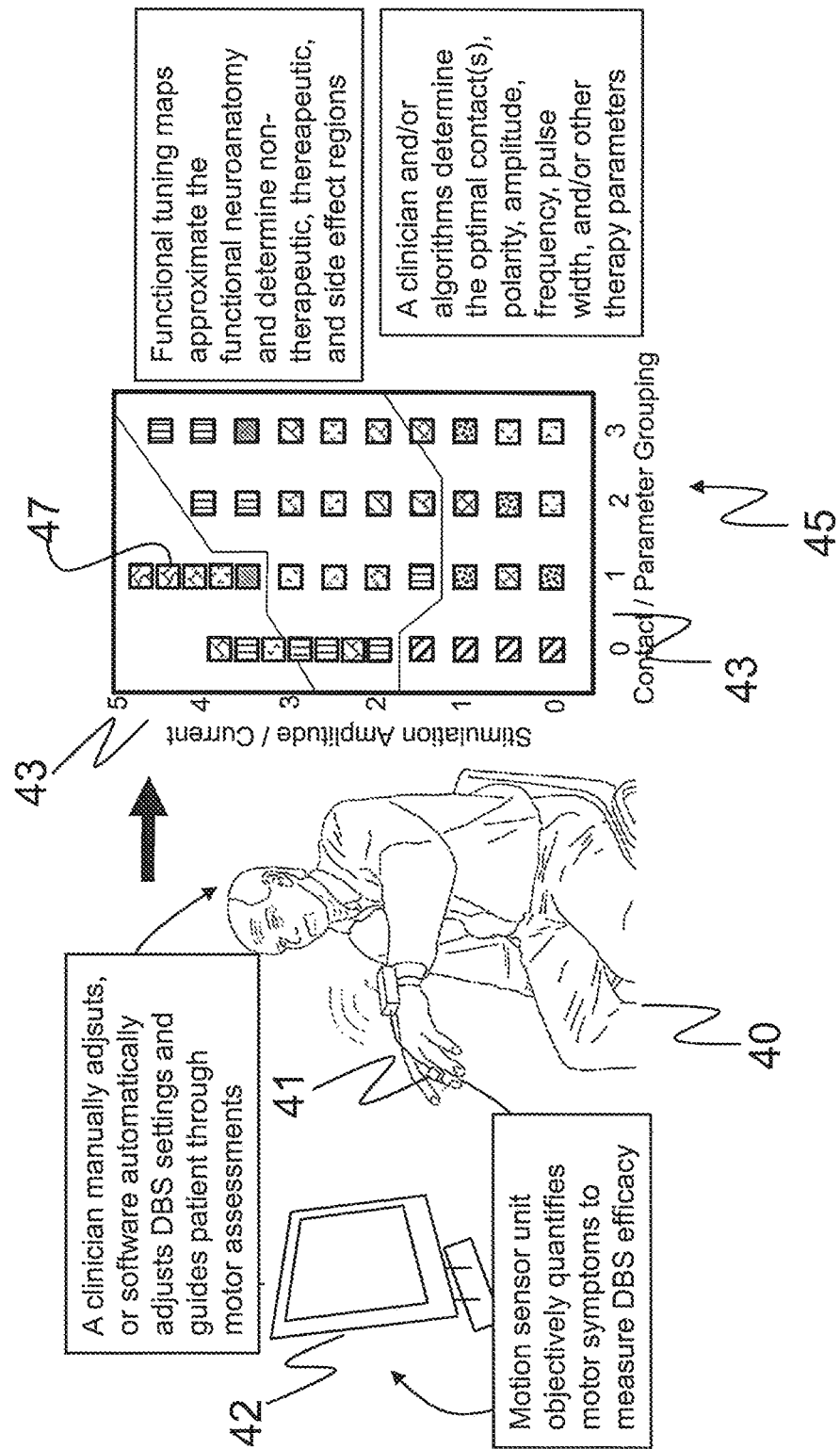
FIG. 8. Illustration of various embodiments of the DBS parameter programming/tuning process.

FIG. 8 depicts a method of the present invention utilizing an automated integrated, and possibly intelligent DBS (or other therapy) training system. As the subject 40 performs motor and cognitive tests, as instructed via a display 42 (automated), while wearing the movement disorder diagnostic device 41, the system records and analyzes the results of those tests in light of the many variables. The system or a clinician, technician or physician then populates a tuning map 45 to show the subject's response to the tested DBS (or other therapy) parameters for each symptom. As noted herein, the axes 43 of the tuning map 45 may represent a single test variable, or may represent a grouping of therapy settings or parameters that are used while the subject 40 conducts a movement disorder test(s). The tuning map 45 is populated by scores 47 representing the severity of the subject's 40 symptom or side effect, or some other metric being measured. The tuning map 45 also helps to map the side effect regions, as well as therapeutic and non-therapeutic regions. A clinician, technician or physician then determines, based on the test results, a set of therapy settings or parameters that are then entered into the subject's therapy (e.g., DBS) device. Alternatively, the system may utilize the tuning map 45 to suggest DBS parameters that will activate the necessary therapeutic regions, avoid the side effect regions, and optimize the life of the device (i.e., battery life, etc.). Whether the parameter determination is manual by a clinician, or automated by an algorithm, the parameters are then entered into the subject's therapy device (not shown) for further testing or for delivering treatment and therapy to the subject.

FIG. 9 illustrates the difference between (a) monopolar and (b) bipolar DBS lead configurations and the ability to activate desired brain areas while avoiding others by shaping the electrical stimulation field. While only mono- and bipolar configurations are depicted, other configurations are envisioned for use with the present invention as well. A monopolar (a) configuration provides electrical stimulation in all directions from the given contact, and that stimulation dissipates as it radiates out from the contact. Bipolar (b) configurations simultaneously provide electrical stimulation from 2 contacts, and depending on the parameters used, can thus alter the shape of the electrical stimulation field. FIG. 9(*a*) shows a monopolar configuration, which provides electrical stimulation in all directions. Thus, with a monopolar configuration, the stimulation provided activates the desired portion 56, which corresponds to the area of the subject's brain which causes occurrence of a movement disorder symptom, but also activates a side effect region 55, which causes a side effect to occur. However, with a bipolar configuration, as in FIG. 9(*b*), the electrical field may be shaped in such a manner so as to activate the desired region 56 corresponding to a symptom and thus treat that symptom, while avoiding the side effect region 55 and thus avoid causing the side effect to occur.

Figure 10:
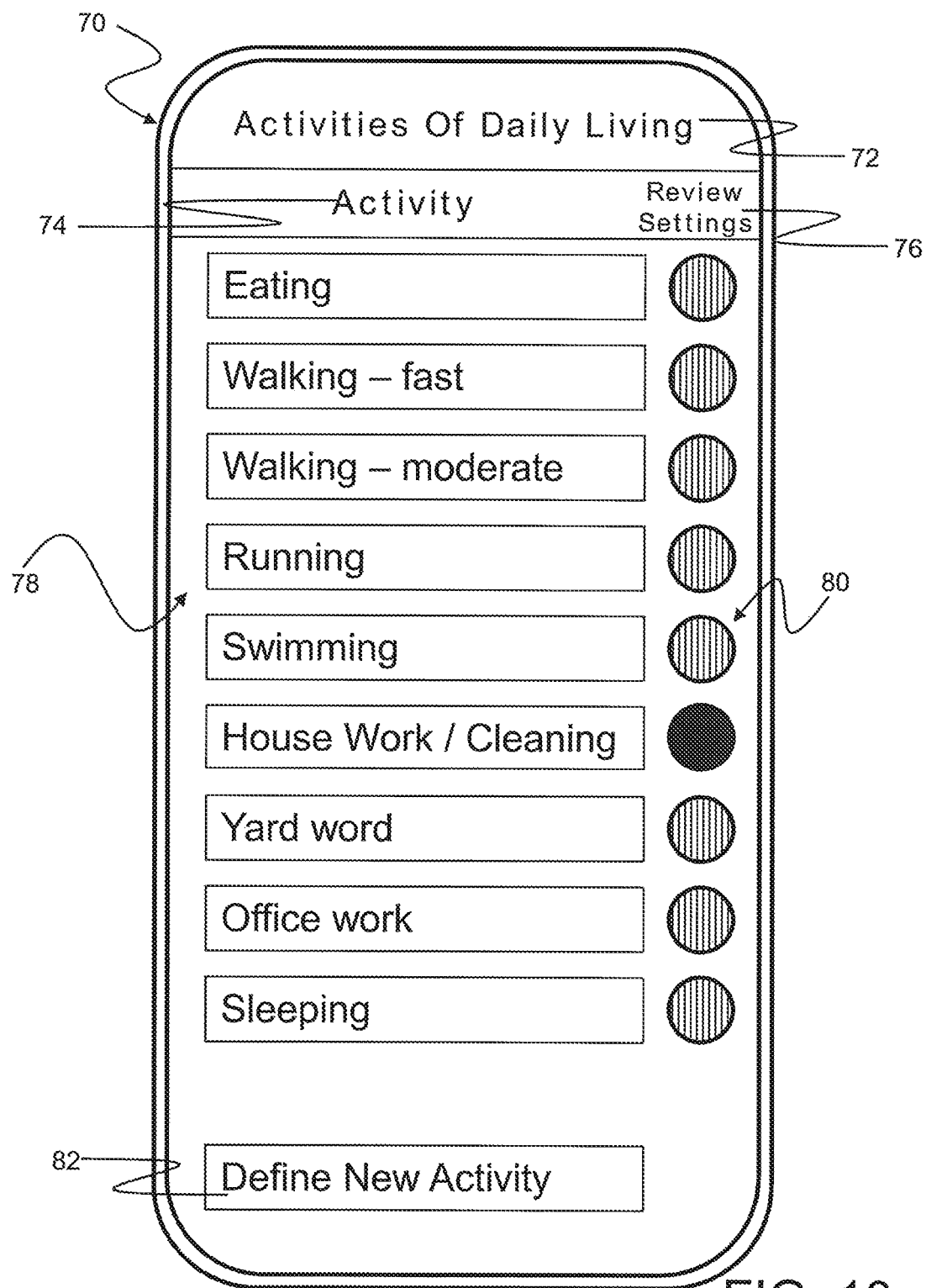
FIG. 10. One embodiment of an interface device allowing a user to select an activity to perform, and which can change the subject's therapy parameters or settings based on the selected activity.

FIG. 10 depicts an exemplary embodiment of a device that can be carried, attached to, or otherwise readily used by the subject. The device 70 can be any variety of interface devices, such as a cellular or smart telephone, PDA, tablet, or the like. In the particular embodiment depicted, the subject can view the device 70 and view, determine and select the type of activity, action or task 78 he or she is about to perform or is performing. The activity list 78 depicts any number of activities, actions or tasks 78, such as activities of daily living that the subject may perform at various points in his or her day. When, for example, the subject knows he or she is going to go for a walk, the subject can merely select the walking activity, and the device 70 would then communicate a set of predetermined therapy settings or parameters to program the subject's therapy device (such as an implanted DBS device). The therapy device would then operate under the newly programmed therapy settings or parameters. The predetermined settings or parameters may be determined and programmed into the device by a clinician, physician or technician before the device is provided to the subject. The initial and subsequent parameters or settings may also be determined by a clinician, physician or technician and transmitted or communicated remotely to the subject's DBS or therapy device. Also alternatively, the system may automatedly and intelligently determine preferred settings or parameters based on the activity, action or task being performed, and the measurements acquired while performing said activity, action or task 78. This automated setting or parameter determination may initially be based on past performances of the elected activity, action or task 78, but real-time measurements during each performance of the activity, action or task 78 may allow for real-time setting or parameter needs to be determined and communicated from the device 70 to the therapy device. Thus, whenever the subject selects a desired activity, action or task 78, the device would automatically reprogram the subject's therapy device to provide the appropriate settings or parameters to most effectively allow the subject to perform the elected activity, action or task 78.

The subject may be given the option to define a new activity, action or task 82. Such capability would most preferably be available in intelligent, automated parameter or setting determination embodiments, though could be available in manual or semi-automated embodiment requiring clinician, physician or technician approval as well. Such capability would allow the subject to perform a new activity, action or task that he or she has not done before, or to create a new level of a previously defined activity, action or task (such as creating a different activity, action or task 78 in the activity list 74 for mowing the lawn and gardening, as opposed to just yard work, as depicted by way of example in the figure). It may be preferable, for some subjects, to only allow a clinician, physician or technician to define new activities, actions or tasks in which case this feature would either be disabled or removed from the interface or device 70. In any event, the automated, intelligent programming systems would allow the device 70 to take real-time measurements of the subject's movements, analyze the movement data, and determine the best therapy parameters or settings for maximizing the subject's ability to perform the activity, action or task. This maximization of the subject's ability to perform the activity, action or task may correspond to a minimization of symptoms, a minimization of side effects, a combination thereof, or any other combination of possible desired results or outcomes described herein as they pertain to the particularly elected activity, action or task.

Optionally, the device 70 may provide the ability to view and review the settings for an elected activity, action or task 76. The subject or a clinician, physician or technician may simply select a button 80 corresponding to the settings for a particular activity, action or task, and the therapy parameters or settings would be displayed for review. Depending on the embodiment or the person reviewing the settings, this option may also provide the ability to manually edit the prescribed settings for a particular activity, action or task. Preferably, the ability to edit the parameters or settings is available only to a clinician, physician or technician. The subject may be able to view the settings in order to take notes or to discuss the settings with the clinician, physician or technician while at a remote location such as at home. In light of the various features of the device that upload and store the parameters and settings in a database, either in real-time or on-demand, the activity settings are similarly reported and stored for remote (in time, location, or both) access.

Figure 11:
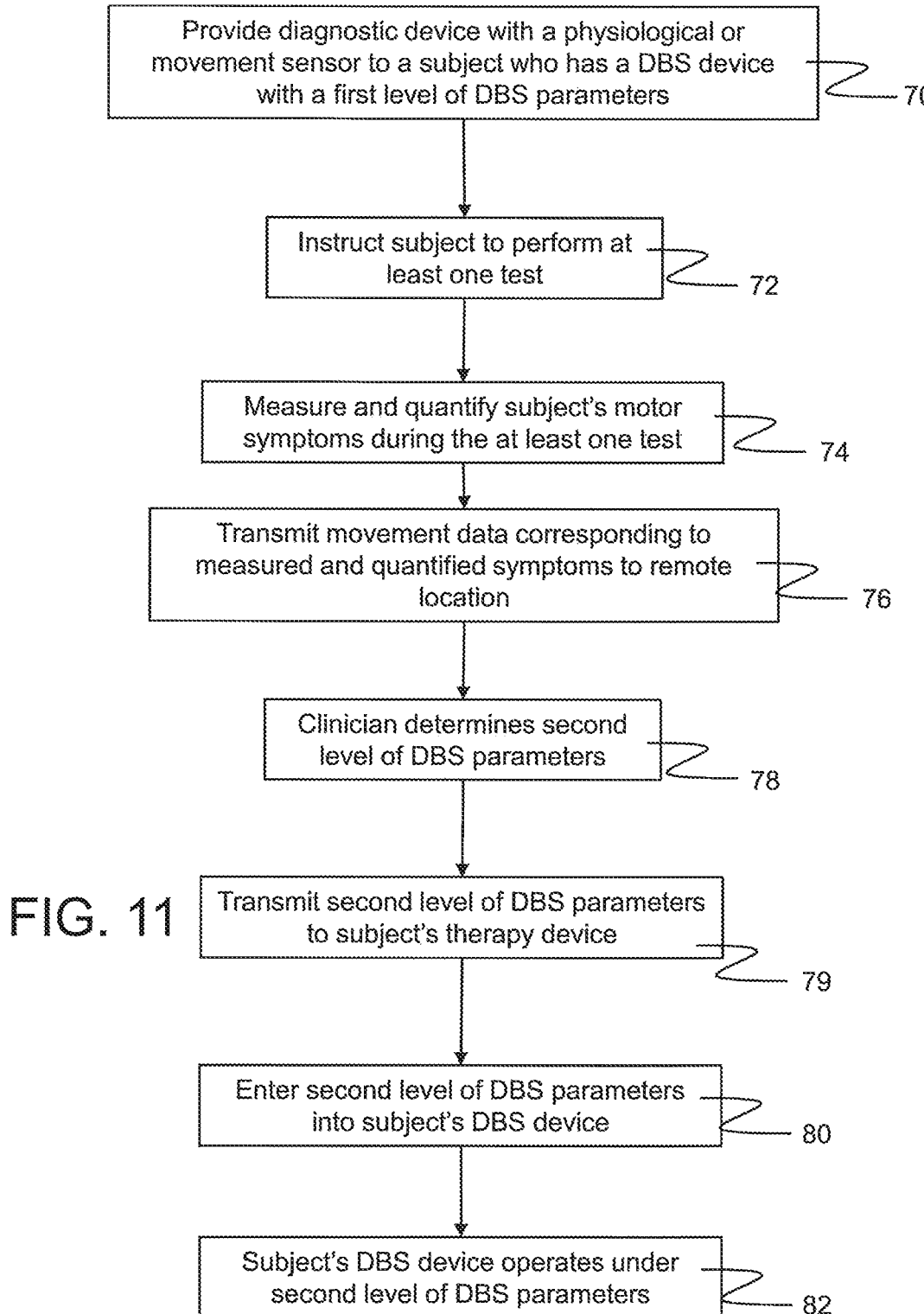
FIG. 11. Flow chart describing one embodiment of the present invention wherein a subject's therapy device is remotely programmed with updated parameters or settings, and where the updated parameters or settings are determined by clinician located remotely from the subject, and the determination is made based on measured and quantified motor symptom data, and the updated parameters or settings are remotely programmed into the subject's therapy device.

FIG. 11 depicts a flow chart representing a method embodiment of the present invention for tuning the movement disorder diagnostic device with new therapy parameters or settings. First, a movement disorder diagnostic device is provided to a subject 70 who has a therapy device, such as a DBS therapy device. The movement disorder diagnostic device is as described herein, but preferably comprises at least one physiological or movement sensor for measuring the subject's external body motion, or some other physiological signal of the subject, where the sensor(s) has a signal related to the subject's motion or other physiological signal. Preferably, the movement disorder diagnostic device is a single unit, though may be multiple units (e.g., separate sensor unit and command/transceiver module), and is adapted to be worn or attached to a portion of the subject's body such that the sensor(s) of the movement disorder diagnostic device are able to measure the movement of that particular portion of the subject's body.

Once the movement disorder diagnostic device has been provided 70 to the subject, and the subject has donned or attached the device, the next step is to instruct the subject 72 to perform at least one movement disorder test(s) while the subject is undergoing therapy from the therapy (e.g., DBS) device, or is under the effects of recently administered therapy therefrom. These instructions may include a list of which test(s) the subject is to perform, directions on how to perform the test, or a combination of both. The instructions to perform a test or tests may be given 72 in person (if in a clinical setting) by a clinician, physician or technician, or more preferably may be provided in an automated or electronic fashion. For example, the instruction to perform the test(s) may be provided automatedly to the subject via a video display, or a notification or alert message provided via such a display or perhaps the subject's smart phone, on a display device via tele- or videoconference with a clinician, physician or technician, or the like. The instructions are provided 72, either audibly, visually, or a combination thereof. The subject's performance of the tasks is thus affected by the therapy being provided, or recently provided by the therapy device.

While the subject is performing the at least one movement disorder test(s) as instructed 72, the step of measuring and quantifying motor symptoms 74 of the subject based at least in part on the signal of the at least one sensor(s) is performed. The movement disorder diagnostic device uses the signal of the at least one sensor(s) to provide an objective measurement and quantification of the severity of the subject's motor symptoms while the subject performs the at least one movement disorder test. The measured and quantified motor symptoms may include specific movement disorder symptoms, side effects from medication and/or therapy, or combinations thereof. The trained scoring algorithms of the movement disorder diagnostic device perform various measurements and calculations to provide this objective quantification of the subject's motor symptoms.

Once the subject's motor symptoms have been measured and quantified 74, data corresponding to these measured and quantified motor symptoms is transmitted to a remote location 76. Typically, the data corresponding to the measured and quantified motor symptoms is an object score, as described herein, but may be represented in numerous ways and means. Preferably, the data is transmitted 76 directly from the subject's movement disorder diagnostic device using at least on electrical component for sending or transmitting signals. Preferably, such transmission is performed wirelessly as described herein, though it may be performed by use of a tethered or docking station system where the diagnostic device is placed in contact with the tethered communications system or docking station which then transmits the data. As described herein, the data is preferably transmitted directly to a remote location where a clinician, physician or technician can access the data immediately or at will for analysis and review. Additionally or alternatively, the data may be transmitted to a form of data storage such as a centralized server, cloud-based server, or other storage database. The clinician, physician or technician can then either access the data directly from a computer device to which the data is transmitted 76 or from the storage system in order to review and analyze the data. Using this data, the clinician, physician or technician then determines a second level of therapy (e.g., DBS) parameters or settings 78 based on the data and with the goal of improving the subject's movement in a manner as described herein. This second level of parameters or settings preferably corresponds to a mode of therapy or treatment that addresses the subject's needs as determined based on the measured and quantified motor symptom data, as well as other data, goals, or objectives. In other words, if the clinician or system determines that the subject is experiencing a very strong tremor, such determination being made as a result of the measurement of the subject's movement and quantifying the severity of the tremor, the second level of parameters or settings 78 would aim to reduce or minimize the tremor the subject is experiencing. As noted, the determination of a second level of parameters or settings may be based on any number of constraints or desired results for the subject, not solely the immediate symptom or side effect the subject is experiencing. For example, if the subject's main concern is reducing or minimizing symptom occurrence and or severity, the clinician, physician or technician, or algorithm will take this desired goal into account when determining the second level of parameters or settings. Similarly, the determination of settings or parameters may be based on a desired reduction or minimization of side effects from medication or the therapy. Also, the determination may be made to balance multiple desired results, such as if a slightly higher rate of occurrence of symptoms is acceptable to the subject in exchange for a minimization of side effects. Other examples of desired results that may be used to determine the second level of therapy parameters or settings for all embodiments include, but are not limited to, a therapeutic window (in terms of time or some other factor) in which the subject most positively responds to therapy, battery life, and other such constraints that might be considered in terms of optimizing the therapy parameters or settings. In any determination, the subject and the clinician, physician or technician decide what the initial desired result is, and these desired results, goals, or constraints are programmed into the algorithm for the decision making process. In some embodiments, the desired result, goal or constraints may be edited or changed in order to allow the second level of parameters to provide optimal treatment for the subject.

Once the second level of therapy parameters or settings has been determined or decided upon, this second level of parameters or settings is then transmitted to the subject's therapy device 79 (e.g., DBS device). The therapy device preferably comprises at least one electronic component for receiving such signals, and uses this at least one component to receive a signal(s) comprising the second level of therapy parameters or settings. The parameters or settings are preferably transmitted 79 via wireless communication, as described herein, between the remote location and the subject's therapy device. Once the therapy device receives the transmitted second level of therapy parameters or settings, the second level of parameters or settings is then entered in to the subject's therapy device 80 for the device to provide therapy according to those parameters or settings 82. As such, the new, second level of parameters or settings is programmed into the subject's therapy device, and the device then operates according to those new parameters or settings 82 and provides that newly determined course of therapy or treatment to the subject. Thus, the system measures and quantifies the subject's symptoms 74, allows a remotely located clinician to determine a second level of therapy parameters or settings that would address those symptoms 78, the second level of parameters or settings is transmitted 79 and programmed into the subject's therapy device 80, and the therapy device implements the second level of parameters or setting to in fact address the subject's symptoms 82.

Figure 12:
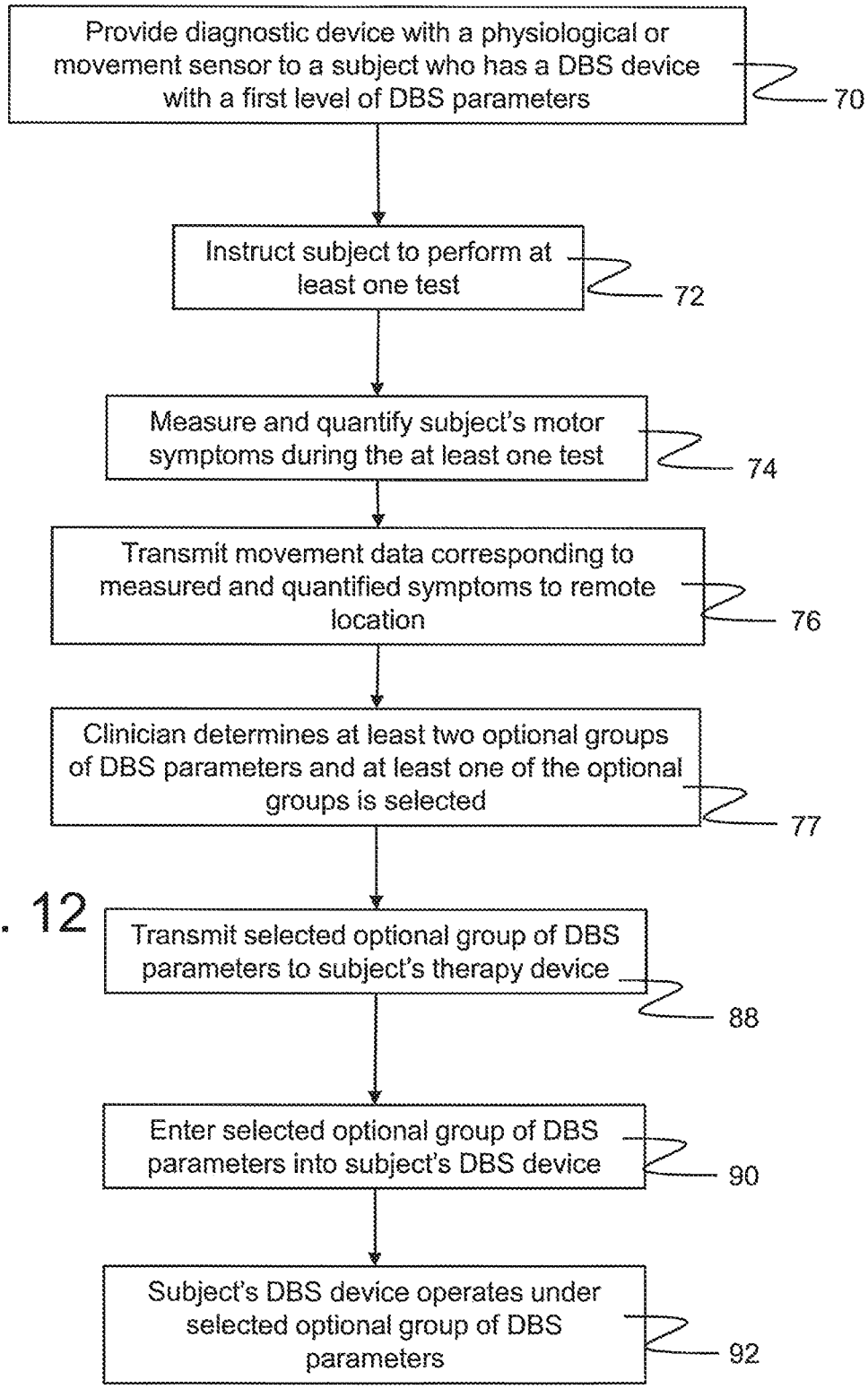
FIG. 12. Flow chart describing one embodiment of the present invention wherein a subject's therapy device is remotely programmed with updated parameters or settings, where a clinician located remotely from the subject provides at least two optional sets of parameters or settings and one of the groups is selected and remotely programmed into the subject's therapy device.

FIG. 12 depicts a flow chart representing a method embodiment of the present invention for tuning the movement disorder diagnostic device with new therapy parameters or settings. First, a movement disorder diagnostic device is provided to a subject 70 who has a therapy device, such as a DBS therapy device. The movement disorder diagnostic device is as described herein, but preferably comprises at least one physiological or movement sensor for measuring the subject's external body motion, or some other physiological signal of the subject, where the sensor(s) has a signal related to the subject's motion or other physiological signal. Preferably, the movement disorder diagnostic device is a single unit, though may be multiple units (e.g., separate sensor unit and command/transceiver module), and is adapted to be worn or attached to a portion of the subject's body such that the sensor(s) of the movement disorder diagnostic device are able to measure the movement of that particular portion of the subject's body.

Once the movement disorder diagnostic device has been provided 70 to the subject, and the subject has donned or attached the device, the next step is to instruct the subject 72 to perform at least one movement disorder test(s) while the subject is undergoing therapy from the therapy (e.g., DBS) device, or is under the effects of recently administered therapy therefrom. These instructions may include a list of which test(s) the subject is to perform, directions on how to perform the test, or a combination of both. The instructions to perform a test or tests may be given 72 in person (if in a clinical setting) by a clinician, physician or technician, or more preferably may be provided in an automated or electronic fashion, such as tele- or videoconference with a clinician, physician or technician. For example, the instruction to perform the test(s) may be provided automatedly to the subject via a video display, or a notification or alert message provided via such a display or perhaps the subject's smart phone, or the like. The instructions are provided 72, either audibly, visually, or a combination thereof. The subject's performance of the tasks is thus affected by the therapy being provided, or recently provided by the therapy device.

While the subject is performing the at least one movement disorder test(s) as instructed 72, the step of measuring and quantifying motor symptoms 74 of the subject based at least in part on the signal of the at least one sensor(s) is performed. The movement disorder diagnostic device uses the signal of the at least one sensor(s) to provide an objective measurement and quantification of the severity of the subject's motor symptoms while the subject performs the at least one movement disorder test. The measured and quantified motor symptoms may include specific movement disorder symptoms, side effects from medication and/or therapy, or combinations thereof. The trained scoring algorithms of the movement disorder diagnostic device perform various measurements and calculations to provide this objective quantification of the subject's motor symptoms.

Once the subject's motor symptoms have been measured and quantified 74, data corresponding to these measured and quantified motor symptoms is transmitted to a remote location 76. Typically, the data corresponding to the measured and quantified motor symptoms is an object score, as described herein, but may be represented in numerous ways and means. Preferably, the data is transmitted 76 directly from the subject's movement disorder diagnostic device using at least on electrical component for sending or transmitting signals. Preferably, such transmission is performed wirelessly as described herein, though it may be performed by use of a tethered or docking station system where the diagnostic device is placed in contact with the tethered communications system or docking station which then transmits the data. As described herein, the data is preferably transmitted directly to a remote location where a clinician, physician or technician can access the data immediately or at will for analysis and review. Additionally or alternatively, the data may be transmitted to a form of data storage such as a centralized server, cloud-based server, or other storage database. The clinician, physician or technician can then either access the data directly from a computer device to which the data is transmitted 76 or from the storage system in order to review and analyze the data. Using this data, the clinician, physician or technician then determines at least two optional groups of therapy (e.g., DBS) parameters or settings 73 based on the data and with the goal of improving the subject's movement in a manner as described herein. The at least two optional groups of parameters or settings preferably each correspond to a different mode of therapy or treatment that addresses the subject's needs as determined based on the measured and quantified motor symptom data, as well as other data, goals, or objectives. In other words, if the system determines that the subject is experiencing a very strong tremor and gait disturbances, such determination being made as a result of the measurement of the subject's movement and quantifying the severity of the tremor and gait disturbance, one of the at least two optional groups of parameters or settings 78 would aim to reduce or minimize the tremor and the other would aim to reduce or minimize the gait disturbances the subject is experiencing. As noted, the determination of at least two optional groups of parameters or settings may be based on any number of constraints or desired results for the subject, not solely the immediate symptom or side effect the subject is experiencing. For example, if the subject's main concern is reducing or minimizing symptom occurrence and or severity, the clinician, physician or technician, or algorithm will take this desired goal into account when determining the at least two optional groups of parameters or settings. Similarly, the determination of settings or parameters may be based on a desired reduction or minimization of side effects from medication or the therapy. Also, the determination may be made to balance multiple desired results, such as if a slightly higher rate of occurrence of symptoms is acceptable to the subject in exchange for a minimization of side effects. Other examples of desired results that may be used to determine the second level of therapy parameters or settings for all embodiments include, but are not limited to, a therapeutic window (in terms of time or some other factor) in which the subject most positively responds to therapy, battery life, and other such constraints that might be considered in terms of optimizing the therapy parameters or settings. In any determination, the subject and the clinician, physician or technician decide what the initial desired result is, and these desired results, goals, or constraints are programmed into the algorithm for the decision making process. In some embodiments, the desired result, goal or constraints may be edited or changed in order to allow the second level of parameters to provide optimal treatment for the subject.

Once the at least two optional groups of therapy parameters or settings has been determined or decided upon, at least one of the optional groups is selected for use 77. Then, the at least one selected optional group of parameters or settings is then transmitted to the subject's therapy device 88 (e.g., DBS device). The therapy device preferably comprises at least one electronic component for receiving such signals, and uses this at least one component to receive a signal(s) comprising the second level of therapy parameters or settings. The at least one selected optional group of parameters or settings are preferably transmitted 88 via wireless communication, as described herein, between the remote location and the subject's therapy device. Once the therapy device receives the transmitted second level of therapy parameters or settings, the selected optional group of parameters or settings is then entered in to the subject's therapy device 90 for the device to provide therapy according to those parameters or settings 92. As such, the new, selected optional group of parameters or settings is programmed into the subject's therapy device, and the device then operates according to those new parameters or settings 92 and provides that newly determined course of therapy or treatment to the subject. Thus, the system measures and quantifies the subject's symptoms 74, allows a remotely located clinician to determine at least two optional groups of therapy parameters or settings that would address those symptoms 77, at least one of the optional groups of parameters or settings is then selected 77, the selected optional group(s) of parameters or settings is transmitted 88 and programmed into the subject's therapy device 90, and the therapy device implements the at least one selected optional group of parameters or setting to in fact address the subject's symptoms 92.

Figure 13:
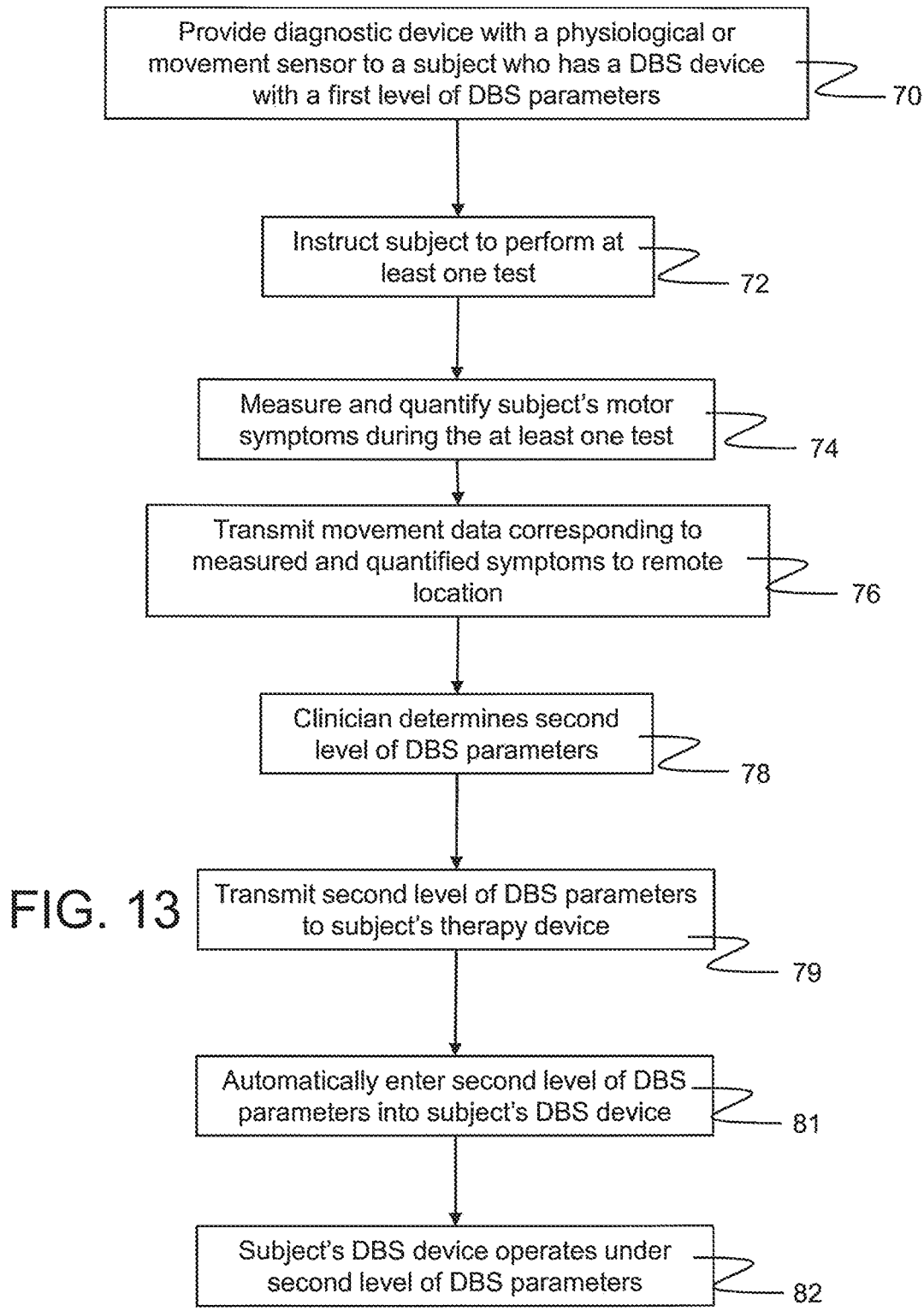
FIG. 13. Flow chart describing one embodiment of the present invention wherein a subject's therapy device is remotely programmed with updated parameters or settings, where a clinician determines a second level of parameters or settings that is transmitted and automatically entered into the subject's therapy device.

FIG. 13 depicts a flow chart representing a method embodiment of the present invention for tuning the movement disorder diagnostic device with new therapy parameters or settings. First, a movement disorder diagnostic device is provided to a subject 70 who has a therapy device, such as a DBS therapy device. The movement disorder diagnostic device is as described herein, but preferably comprises at least one physiological or movement sensor for measuring the subject's external body motion, or some other physiological signal of the subject, where the sensor(s) has a signal related to the subject's motion or other physiological signal. Preferably, the movement disorder diagnostic device is a single unit, though may be multiple units (e.g., separate sensor unit and command/transceiver module), and is adapted to be worn or attached to a portion of the subject's body such that the sensor(s) of the movement disorder diagnostic device are able to measure the movement of that particular portion of the subject's body.

Once the movement disorder diagnostic device has been provided 70 to the subject, and the subject has donned or attached the device, the next step is to instruct the subject 72 to perform at least one movement disorder test(s) while the subject is undergoing therapy from the therapy (e.g., DBS) device, or is under the effects of recently administered therapy therefrom. These instructions may include a list of which test(s) the subject is to perform, directions on how to perform the test, or a combination of both. The instructions to perform a test or tests may be given 72 in person (if in a clinical setting) by a clinician, physician or technician, or more preferably may be provided in an automated or electronic fashion. For example, the instruction to perform the test(s) may be provided automatedly to the subject via a video display, or a notification or alert message provided via such a display or perhaps the subject's smart phone, on a display device via tele- or videoconference with a clinician, physician or technician, or the like. The instructions are provided 72, either audibly, visually, or a combination thereof. The subject's performance of the tasks is thus affected by the therapy being provided, or recently provided by the therapy device.

While the subject is performing the at least one movement disorder test(s) as instructed 72, the step of measuring and quantifying motor symptoms 74 of the subject based at least in part on the signal of the at least one sensor(s) is performed. The movement disorder diagnostic device uses the signal of the at least one sensor(s) to provide an objective measurement and quantification of the severity of the subject's motor symptoms while the subject performs the at least one movement disorder test. The measured and quantified motor symptoms may include specific movement disorder symptoms, side effects from medication and/or therapy, or combinations thereof. The trained scoring algorithms of the movement disorder diagnostic device perform various measurements and calculations to provide this objective quantification of the subject's motor symptoms.

Once the subject's motor symptoms have been measured and quantified 74, data corresponding to these measured and quantified motor symptoms is transmitted to a remote location 76. Typically, the data corresponding to the measured and quantified motor symptoms is an object score, as described herein, but may be represented in numerous ways and means. Preferably, the data is transmitted 76 directly from the subject's movement disorder diagnostic device using at least on electrical component for sending or transmitting signals. Preferably, such transmission is performed wirelessly as described herein, though it may be performed by use of a tethered or docking station system where the diagnostic device is placed in contact with the tethered communications system or docking station which then transmits the data. As described herein, the data is preferably transmitted directly to a remote location where a clinician, physician or technician can access the data immediately or at will for analysis and review. Additionally or alternatively, the data may be transmitted to a form of data storage such as a centralized server, cloud-based server, or other storage database. The clinician, physician or technician can then either access the data directly from a computer device to which the data is transmitted 76 or from the storage system in order to review and analyze the data. Using this data, the clinician, physician or technician then determines a second level of therapy (e.g., DBS) parameters or settings 78 based on the data and with the goal of improving the subject's movement in a manner as described herein. This second level of parameters or settings preferably corresponds to a mode of therapy or treatment that addresses the subject's needs as determined based on the measured and quantified motor symptom data, as well as other data, goals, or objectives. In other words, if the clinician or system determines that the subject is experiencing a very strong tremor, such determination being made as a result of the measurement of the subject's movement and quantifying the severity of the tremor, the second level of parameters or settings 78 would aim to reduce or minimize the tremor the subject is experiencing. As noted, the determination of a second level of parameters or settings may be based on any number of constraints or desired results for the subject, not solely the immediate symptom or side effect the subject is experiencing. For example, if the subject's main concern is reducing or minimizing symptom occurrence and or severity, the clinician, physician or technician, or algorithm will take this desired goal into account when determining the second level of parameters or settings. Similarly, the determination of settings or parameters may be based on a desired reduction or minimization of side effects from medication or the therapy. Also, the determination may be made to balance multiple desired results, such as if a slightly higher rate of occurrence of symptoms is acceptable to the subject in exchange for a minimization of side effects. Other examples of desired results that may be used to determine the second level of therapy parameters or settings for all embodiments include, but are not limited to, a therapeutic window (in terms of time or some other factor) in which the subject most positively responds to therapy, battery life, and other such constraints that might be considered in terms of optimizing the therapy parameters or settings. In any determination, the subject and the clinician, physician or technician decide what the initial desired result is, and these desired results, goals, or constraints are programmed into the algorithm for the decision making process. In some embodiments, the desired result, goal or constraints may be edited or changed in order to allow the second level of parameters to provide optimal treatment for the subject.

Once the second level of therapy parameters or settings has been determined or decided upon, this second level of parameters or settings is then transmitted to the subject's therapy device 79 (e.g., DBS device). The therapy device preferably comprises at least one electronic component for receiving such signals, and uses this at least one component to receive a signal(s) comprising the second level of therapy parameters or settings. The parameters or settings are preferably transmitted 79 via wireless communication, as described herein, between the remote location and the subject's therapy device. Preferably, the clinician, physician or technician updates the settings or parameters in the software package and these parameters or settings are transmitted and automatically entered 81 into the subject's device requiring no direct interaction between the clinician, physician or technician and the subject's therapy device. Thus, once the therapy device receives the transmitted second level of therapy parameters or settings, the second level of parameters or settings is then automatically entered in to the subject's therapy device 81 for the device to provide therapy according to those parameters or settings 82. As such, the new, second level of parameters or settings is programmed into the subject's therapy device, and the device then operates according to those new parameters or settings 82 and provides that newly determined course of therapy or treatment to the subject. Thus, the system measures and quantifies the subject's symptoms 74, allows a remotely located clinician to determine a second level of therapy parameters or settings that would address those symptoms 78, the second level of parameters or settings is transmitted 79 and automatically programmed 81 into the subject's therapy device 80, and the therapy device implements the second level of parameters or setting to in fact address the subject's symptoms 82.

Figure 14:
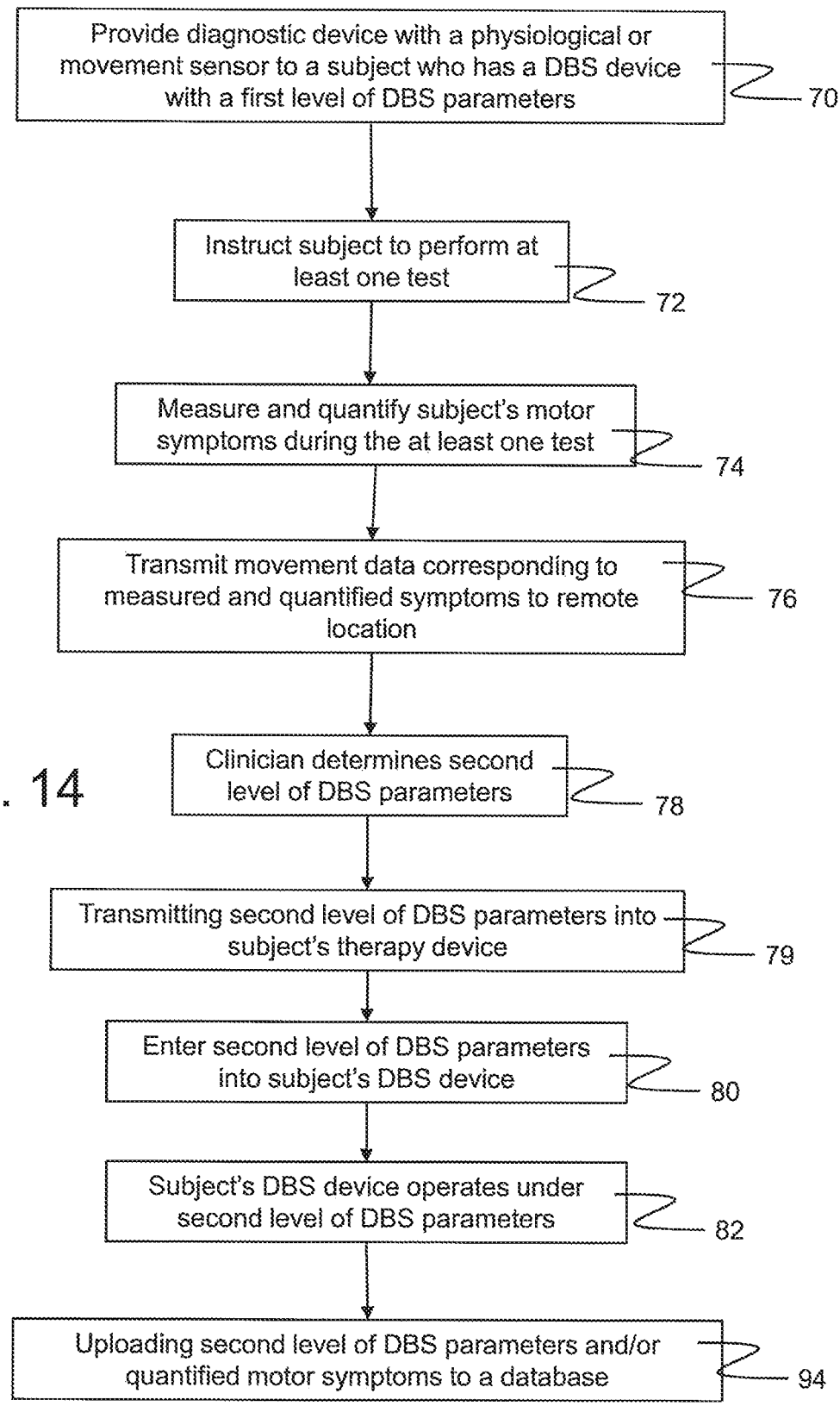
FIG. 14. Flow chart describing one embodiment of the present invention wherein a subject's therapy device is remotely programmed with updated parameters or settings, and where the updated parameters or settings are determined by clinician located remotely from the subject, and the determination is made based on measured and quantified motor symptom data, and the updated parameters or settings are remotely programmed into the subject's therapy device while also uploading the parameters and/or movement data to a database for storage.

FIG. 14 depicts a flow chart representing a method embodiment of the present invention for tuning the movement disorder diagnostic device with new therapy parameters or settings. First, a movement disorder diagnostic device is provided to a subject 70 who has a therapy device, such as a DBS therapy device. The movement disorder diagnostic device is as described herein, but preferably comprises at least one physiological or movement sensor for measuring the subject's external body motion, or some other physiological signal of the subject, where the sensor(s) has a signal related to the subject's motion or other physiological signal. Preferably, the movement disorder diagnostic device is a single unit, though may be multiple units (e.g., separate sensor unit and command/transceiver module), and is adapted to be worn or attached to a portion of the subject's body such that the sensor(s) of the movement disorder diagnostic device are able to measure the movement of that particular portion of the subject's body.

Once the movement disorder diagnostic device has been provided 70 to the subject, and the subject has donned or attached the device, the next step is to instruct the subject 72 to perform at least one movement disorder test(s) while the subject is undergoing therapy from the therapy (e.g., DBS) device, or is under the effects of recently administered therapy therefrom. These instructions may include a list of which test(s) the subject is to perform, directions on how to perform the test, or a combination of both. The instructions to perform a test or tests may be given 72 in person (if in a clinical setting) by a clinician, physician or technician, or more preferably may be provided in an automated or electronic fashion. For example, the instruction to perform the test(s) may be provided automatedly to the subject via a video display, or a notification or alert message provided via such a display or perhaps the subject's smart phone, on a display device via tele- or videoconference with a clinician, physician or technician, or the like. The instructions are provided 72, either audibly, visually, or a combination thereof. The subject's performance of the tasks is thus affected by the therapy being provided, or recently provided by the therapy device.

While the subject is performing the at least one movement disorder test(s) as instructed 72, the step of measuring and quantifying motor symptoms 74 of the subject based at least in part on the signal of the at least one sensor(s) is performed. The movement disorder diagnostic device uses the signal of the at least one sensor(s) to provide an objective measurement and quantification of the severity of the subject's motor symptoms while the subject performs the at least one movement disorder test. The measured and quantified motor symptoms may include specific movement disorder symptoms, side effects from medication and/or therapy, or combinations thereof. The trained scoring algorithms of the movement disorder diagnostic device perform various measurements and calculations to provide this objective quantification of the subject's motor symptoms.

Once the subject's motor symptoms have been measured and quantified 74, data corresponding to these measured and quantified motor symptoms is transmitted to a remote location 76. Typically, the data corresponding to the measured and quantified motor symptoms is an object score, as described herein, but may be represented in numerous ways and means. Preferably, the data is transmitted 76 directly from the subject's movement disorder diagnostic device using at least on electrical component for sending or transmitting signals. Preferably, such transmission is performed wirelessly as described herein, though it may be performed by use of a tethered or docking station system where the diagnostic device is placed in contact with the tethered communications system or docking station which then transmits the data. As described herein, the data is preferably transmitted directly to a remote location where a clinician, physician or technician can access the data immediately or at will for analysis and review. Additionally or alternatively, the data may be transmitted to a form of data storage such as a centralized server, cloud-based server, or other storage database. The clinician, physician or technician can then either access the data directly from a computer device to which the data is transmitted 76 or from the storage system in order to review and analyze the data. Using this data, the clinician, physician or technician then determines a second level of therapy (e.g., DBS) parameters or settings 78 based on the data and with the goal of improving the subject's movement in a manner as described herein. This second level of parameters or settings preferably corresponds to a mode of therapy or treatment that addresses the subject's needs as determined based on the measured and quantified motor symptom data, as well as other data, goals, or objectives. In other words, if the clinician or system determines that the subject is experiencing a very strong tremor, such determination being made as a result of the measurement of the subject's movement and quantifying the severity of the tremor, the second level of parameters or settings 78 would aim to reduce or minimize the tremor the subject is experiencing. As noted, the determination of a second level of parameters or settings may be based on any number of constraints or desired results for the subject, not solely the immediate symptom or side effect the subject is experiencing. For example, if the subject's main concern is reducing or minimizing symptom occurrence and or severity, the clinician, physician or technician, or algorithm will take this desired goal into account when determining the second level of parameters or settings. Similarly, the determination of settings or parameters may be based on a desired reduction or minimization of side effects from medication or the therapy. Also, the determination may be made to balance multiple desired results, such as if a slightly higher rate of occurrence of symptoms is acceptable to the subject in exchange for a minimization of side effects. Other examples of desired results that may be used to determine the second level of therapy parameters or settings for all embodiments include, but are not limited to, a therapeutic window (in terms of time or some other factor) in which the subject most positively responds to therapy, battery life, and other such constraints that might be considered in terms of optimizing the therapy parameters or settings. In any determination, the subject and the clinician, physician or technician decide what the initial desired result is, and these desired results, goals, or constraints are programmed into the algorithm for the decision making process. In some embodiments, the desired result, goal or constraints may be edited or changed in order to allow the second level of parameters to provide optimal treatment for the subject.

Once the second level of therapy parameters or settings has been determined or decided upon, this second level of parameters or settings is then transmitted to the subject's therapy device 79 (e.g., DBS device). The therapy device preferably comprises at least one electronic component for receiving such signals, and uses this at least one component to receive a signal(s) comprising the second level of therapy parameters or settings. The parameters or settings are preferably transmitted 79 via wireless communication, as described herein, between the remote location and the subject's therapy device. Once the therapy device receives the transmitted second level of therapy parameters or settings, the second level of parameters or settings is then entered in to the subject's therapy device 80 for the device to provide therapy according to those parameters or settings 82. As such, the new, second level of parameters or settings is programmed into the subject's therapy device, and the device then operates according to those new parameters or settings 82 and provides that newly determined course of therapy or treatment to the subject. In this particular embodiment, the system additionally uploads or transmits 94 the second level of DB S parameters or setting and/or the quantified motor symptom data to a remote location such as a database or server for storage and or access by the clinician at a later time. The uploading or transmission of the parameters or settings and/or data is preferably done substantially simultaneously with transmitting the parameters or settings to the subject's therapy device, however it can be done at a later time. Thus, the system measures and quantifies the subject's symptoms 74, allows a remotely located clinician to determine a second level of therapy parameters or settings that would address those symptoms 78, the second level of parameters or settings is transmitted 79 and programmed into the subject's therapy device 80, and the therapy device implements the second level of parameters or setting to in fact address the subject's symptoms 82, and additionally the parameters or settings and/or the quantified movement data is transmitted to a database or other storage medium 94 for later access and/or storage of the data.

Figure 15:
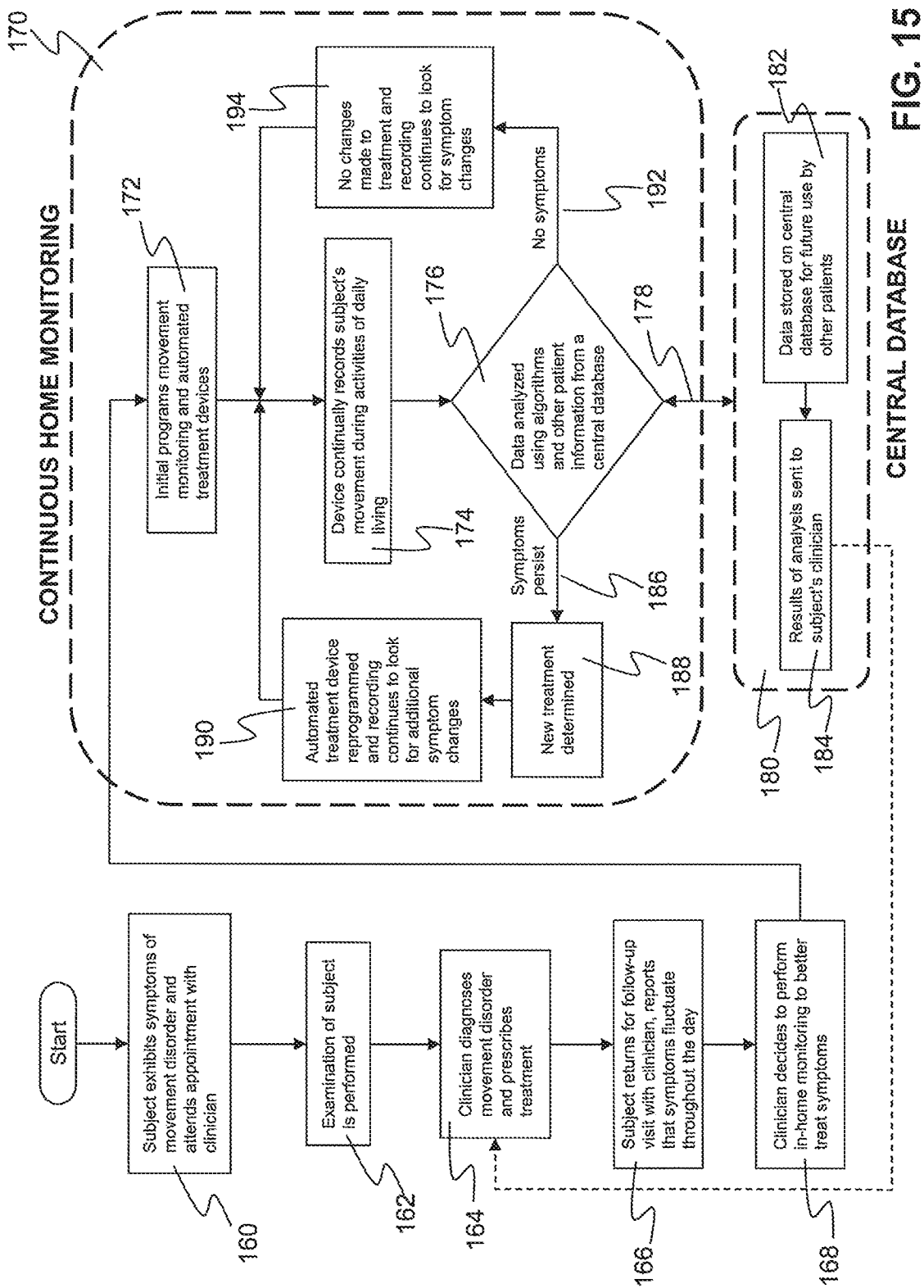
FIG. 15. Flow chart depicting a start-to-finish description of the process from the subject exhibiting movement disorder symptoms through treatment and therapy of those movement disorder symptoms, and where the subject's therapy device is programmed newly determined therapy parameters or settings.

FIG. 15 depicts an operating embodiment of the present invention beginning with the initial occurrence of movement disorder symptoms and ending with continuing monitoring and treatment or therapy. The depicted embodiment describes a system involving continuous home monitoring such that the device operates virtually full-time, monitoring, measuring and analyzing the subject's movement data continually; however, alternative embodiments exist that operate similarly, but with part-time or on-demand monitoring, measuring and analysis. In either embodiment, the subject initially exhibits symptoms of a movement disorder and attends an appointment with a clinician 160. At the appointment, the clinician examines the subject 162, and upon analysis, diagnoses the subject as having a movement disorder, and subsequently orders a course of treatment or therapy 164. At a follow-up visit, the subject may report that symptoms fluctuate greatly throughout the day 166, even while on the prescribed treatment or therapy plan. The clinician then decides to perform in-home continual testing 168 to better determine the severity of the subject's symptoms. Continuous home monitoring 170 begins with the initial programming 172 of any movement monitoring devices or automated treatment delivery devices for the subject, or instructing the subject how to do so. This initial programming may be performed in-clinic or remotely, and may be performed manually or integrated with the review of a clinician, physician or technician, or may be performed intelligently in an automated or semi-automated process utilizing trained tuning algorithms. The device, containing at least one sensor, preferably an accelerometer and/or gyroscope of at least three axes, but optionally another sensor capable of measuring motion, such as an EMG, continually records the subject's movement during activities of daily living 174. In addition, the device can include two or more types of sensors, preferably accelerometers and gyroscopes. Activities of daily living may include folding laundry, handwriting, eating, dressing, self-care, walking, running, and the like. Optionally, the clinician may order the subject to perform clinical tasks such as finger tapping, nose touching, or the like, as defined by standardized scales such as the UPDRS, TRS, and the like, at regularly scheduled periods. Such movement data would also be continually recorded.

A trained tuning algorithm, preferably incorporated by at least one computer processor, analyzes the recorded movement data 176. This data analysis may be performed at a scheduled time where the data is uploaded to the algorithm and analyzed, or, more preferably, may be performed in real time. The algorithm and processor function to distinguish voluntary motion of activities of daily living or clinician ordered tasks from movement disorder symptoms and quantify their severity. Preferably the trained algorithms and computer processor are also in two-way communication 178 with a central database 180 or multiple databases made up of previous patient movement data, disorder histories, treatment histories, and the like. Preferably two or more databases are used for reading. Such a database 180 would preferably retain information from the current subject for use with future subjects 182 (maintaining subject privacy and confidentiality at all times) and work with the trained algorithms and processor to determine a recommended treatment for the current subject based on the previous patient data. This database 180 could optionally be used as a real-time gateway for providing updates to the subject's clinician 184 regarding the subject's status.

If the trained algorithms and processor determine 176 that the patient still suffers from movement disorder symptoms 186, a new course of treatment or therapy is determined 188 either based solely on the subject's measured and quantified symptoms, in conjunction with the central database 180 as previously described, or a combination of the two. If the subject has an automated treatment delivery device, it is preferably reprogramed according to the new treatment protocol 190. Preferably, this reprogramming of the subject's device is performed remotely, and in an automated, intelligent fashion requiring little, or more preferably no interaction from a clinician, physician or technician. The movement measuring device then continues to record new movement data and the process repeats. If the trained algorithms and processor determine 176 movement disorder symptoms no longer persist 192 then no new treatment is needed, no changes are made 194, and the device continues recording movement data.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A method of tuning a movement disorder therapy system comprising steps of:
    providing a movement disorder diagnostic (MD2) device to a subject with an implanted deep brain stimulation (DBS) device having a battery, and further being operable according to adjustable DBS parameters, the MD2 device comprising at least one physiological or movement sensor capable of generating a signal and at least one electronic component comprising at least a transmitter, and the DBS parameters include one or more of electrode polarity, frequency, amplitude, current, pulse width/wavelength, waveform type, and contact configuration;
    identifying and measuring symptomatic movement with the MD2 device both while the subject is performing activities of daily living and undergoing DBS therapy or is under the effects of DBS therapy, the identified symptomatic movement data corresponding to a set of first level DBS parameters of the DBS therapy, the identified and measured symptomatic movement data of the subject based at least in part on the generated signal from the at least one physiological or movement sensor during the activities of daily living;
    transmitting, with the at least one electronic component, the measured symptomatic movement data to a processor;
    extracting, with the processor, at least one kinematic feature from the measured symptomatic movement data;
    processing, with the processor, the at least one kinematic feature with a quantification algorithm to obtain at least one score corresponding to a quantified severity of the subject's movement disorder or at least one symptom of such movement disorder;
    displaying, on a display, the subject's measured symptomatic movement data and/or the at least one score to a clinician, physician or technician;
    determining, by the clinician, physician or technician, based at least in part on the subject's measured symptomatic movement data and/or the at least one score, a set of second level DBS parameters to reduce the severity of motor symptoms of the subject's movement disorder and/or increase battery life of the DBS;
    entering, either automatically with the processor or manually by the clinician, physician or technician, the second level DBS parameters into a programmer device in communication with the subject's DBS device such that the subject's DBS device operates under the second level DBS parameters; and
    supplying, by the DBS device, a stimulation current to the subject's brain under the second level DBS parameters to provide altered DBS therapy to the subject.

2. The method of claim 1, wherein the subject's measured symptomatic movement data and/or the at least one score are displayed or provided remotely to the clinician, physician or technician who determines the second level of DBS parameters, which are further entered remotely by the clinician, physician or technician, either manually or automatically, or through communication with the subject who enters the DBS parameters.

3. The method of claim 1, wherein the second level of DBS parameters corresponds to a quantifiable decrease in the severity and/or occurrence of at least one side effect.

4. The method of claim 1, wherein the quantification algorithm comprises one or more of a simple or multiple linear regression, an artificial neural network, a Bayesian network, or a genetic algorithm; and
    wherein the at least one kinematic feature is a feature selected from the list comprising peak power angular velocity, peak power angle, RMS angular velocity, frequency, maximum amplitude, maximum peak-to-peak amplitude, mean angular velocity, wavelet parameters, and the covariance or standard deviation over time of any of peak power angular velocity, peak power angle, RMS angular velocity, frequency, maximum amplitude, maximum peak-to-peak amplitude, mean angular velocity, or wavelet parameters.

5. The method of claim 1, further comprising the step of uploading the first and second level DBS parameters, the measured symptomatic movement data and/or the at least one score to a remote database for storage and later access by a clinician, physician or technician, for creating a subject report, for research or for training a MD2 device and/or DBS device.

6. The method of claim 1, wherein the data corresponding to the subject's measured symptomatic movement data, the DBS parameters and/or the at least one score is displayed visually for review by the clinician, physician or technician in the form of a tuning map comprising a two-dimensional representation of a three-dimensional graph relating motor symptom severity and/or therapeutic side-effect severity to DBS parameter settings.

7. The method of claim 1, wherein the processor is part of a smart phone or portable computer.

8. A method of tuning a movement disorder therapy system comprising steps of:

providing a movement disorder diagnostic device (MD3) to a subject with an implanted deep brain stimulation (DBS) device having a battery, and further being operable according to adjustable DBS parameters or an integrated drug delivery pump operable according to a dosing command, the MD2 device comprising at least one physiological or movement sensor capable of generating a signal and at least one electronic component comprising at least a transmitter, the DBS parameters include one or more of electrode polarity, frequency, amplitude, current, pulse width/wavelength, waveform type, and contact configuration, or the dosing command including one or more of dose timing and dose volume;

identifying and measuring symptomatic movement with the MD2 device both while the subject is performing activities of daily living and undergoing DBS therapy, is under the effects of DBS therapy, is receiving drug therapy, or us under the effects of drug therapy, the identified symptomatic movement data corresponding to a set of first level DBS parameters of the DBS therapy or a first dosing command, the identified and measured symptomatic movement data of the subject based at least in part on the generated signal from the at least one physiological or movement sensor during the activities of daily living;

transmitting, with the at least one electronic component, the measured symptomatic movement data to a processor;

extracting, with the processor, at least one kinematic feature from the measured symptomatic movement data;

processing, with the processor, the at least one kinematic feature with a quantification algorithm to obtain at least one score corresponding to a quantified severity of the subject's movement disorder or at least one symptom of such movement disorder;

determining, automatically with the processor, based at least in part on the subject's measured symptomatic movement data and/or the at least one score, a set of second level DBS parameters or a second dosing command to reduce the severity of the subject's identified symptomatic movement and/or increase battery life of the DBS or integrated drug delivery pump;

displaying, on a display, the set of second level DBS parameters or second dosing command, and the subject's measured symptomatic movement data and/or the at least one score to a clinician, physician or technician;

entering, either with the processor or manually by the clinician, physician or technician, the second level DBS parameters or second dosing command into a programmer device in communication with the subject's DBS device or integrated drug delivery pump such that the subject's DBS device operates under the second level DBS parameters or the subject's integrated drug delivery pump operates according to the second dosing command; and supplying, by the DBS device, a stimulation current to the subject's brain under the second level DBS parameters to provide altered DBS therapy to the subject or, by the integrated drug delivery pump, a drug dose according to the second dosing command to provide altered drug therapy to the subject.

9. The method of claim 8, wherein the subject's the second level of DBS parameters, second dosing command, measured symptomatic movement data and/or the at least one score are displayed or provided remotely to the clinician, physician or technician who approves the second level of DBS parameters or second dosing command, which are further entered remotely by the clinician, physician or technician, either manually or automatically by approval, or through communication with the subject who enters or approves the change in DBS parameters or dosing command.

10. The method of claim 8, wherein the second level of DBS parameters consists of at least two optional groups of DBS parameters, or the second dosing command consists of at least two different dose options, at least one optional group of DBS parameters or dose options is provided that correspond to a motor symptom, and at least one group of DBS parameters or dose options corresponds to a side effect, and the selected group for the second level of DBS parameters or dose options corresponds to a quantifiable decrease in the severity and/or occurrence of the selected motor symptom or side effect.

11. The method of claim 8, wherein the quantification algorithm comprises one or more of a simple or multiple linear regression, an artificial neural network, a Bayesian network, or a genetic algorithm; and wherein the at least one kinematic feature is a feature selected from the list comprising peak power angular velocity, peak power angle, RMS angular velocity, frequency, maximum amplitude, maximum peak-to-peak amplitude, mean angular velocity, wavelet parameters, and the covariance or standard deviation over time of any of peak power angular velocity, peak power angle, RMS angular velocity, frequency, maximum amplitude, maximum peak-to-peak amplitude, mean angular velocity, or wavelet parameters.

12. The method of claim 8, wherein the processor is part of a smart phone or portable computer.

13. The method of claim 8, further comprising the step of uploading the first and second level DBS parameters, the first and second dosing commands, the measured symptomatic movement data and/or the at least one score to a remote database for storage and later access by a clinician, physician or technician, for creating a subject report, for research or for training a MD2 device, DBS device, and/or drug delivery device.

14. The method of claim 8, wherein the data corresponding to the subject's measured symptomatic movement data, the DBS parameters, dosing commands, and/or the at least one score is displayed visually for review by the clinician, physician or technician in the form of a tuning map comprising a two-dimensional representation of a three-dimensional graph relating motor symptom severity and/or therapeutic side-effect severity to DBS parameter settings or dosing command.

15. A method of tuning a movement disorder therapy system comprising steps of:

providing a movement disorder diagnostic (MD2) device to a subject with an implanted deep brain stimulation (DBS) device having a battery operable, and further according to adjustable DBS parameters, the MD2 device comprising at least one physiological or movement sensor capable of generating a signal and at least one electronic component comprising at least a transmitter, and the DBS parameters include one or more of electrode polarity, frequency, amplitude, current, pulse width/wavelength, waveform type, and contact configuration;

identifying and measuring symptomatic movement with the MD2 device both while the subject is performing activities of daily living and undergoing DBS therapy or is under the effects of DBS therapy, the identified symptomatic movement data corresponding to a set of first level DBS parameters of the DBS therapy, the identified and measured symptomatic movement data of the subject based at least in part on the generated signal from the at least one physiological or movement sensor during the activities of daily living;

transmitting, with the at least one electronic component, the measured symptomatic movement data to a processor;

extracting, with the processor, at least one kinematic feature from the measured symptomatic movement data;

processing, with the processor, the at least one kinematic feature with a quantification algorithm to obtain at least one score corresponding to a quantified severity of the subject's movement disorder or at least one symptom of such movement disorder;

determining, automatically with the processor, based at least in part on the subject's measured symptomatic movement data and/or the at least one score, a set of second level DBS parameters to reduce the severity of the subject's identified symptomatic movement and/or increase battery life of the DBS;

entering, automatically with the processor, the second level DBS parameters into a programmer device in communication with the subject's DBS device such that the subject's DBS device operates under the second level DBS parameters; and supplying, by the DBS device, a stimulation current to the subject's brain under the second level DBS parameters to provide altered DBS therapy to the subject.

16. The method of claim 15, wherein the processor is part of a smart phone or portable computer.

17. The method of claim 15, wherein the second level DBS parameters corresponds to a quantifiable decrease in the severity and/or occurrence of at least one side effect or at least one motor symptom.

18. The method of claim 15, wherein the quantification algorithm comprises one or more of a simple or multiple linear regression, an artificial neural network, a Bayesian network, or a genetic algorithm; and wherein the at least one kinematic feature is a feature selected from the list comprising peak power angular velocity, peak power angle, RMS angular velocity, frequency, maximum amplitude, maximum peak-to-peak amplitude, mean angular velocity, wavelet parameters, and the covariance or standard deviation over time of any of peak power angular velocity, peak power angle, RMS angular velocity, frequency, maximum amplitude, maximum peak-to-peak amplitude, mean angular velocity, or wavelet parameters.

19. The method of claim 15, wherein the data corresponding to the subject's measured symptomatic movement data, the DBS parameters and/or the at least one score is displayed visually for review by the clinician, physician or technician in the form of a tuning map comprising a two-dimensional representation of a three-dimensional graph relating motor symptom severity and/or therapeutic side-effect severity to DBS parameter settings.

20. The method of claim 15, further comprising the step of uploading the first and second level DBS parameters, the measured symptomatic movement data and/or the at least one score to a remote database for storage and later access by a clinician, physician or technician, for creating a subject report, for research or for training a MD2 device and/or DBS device.

* * * * *